(12) United States Patent
Maeda et al.

(10) Patent No.: US 8,017,738 B2
(45) Date of Patent: Sep. 13, 2011

(54) HEMOPOIETIN RECEPTOR PROTEIN, NR10

(75) Inventors: Masatsugu Maeda, Ibaraki (JP); Noriko Yaguchi, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 829 days.

(21) Appl. No.: 11/980,135

(22) Filed: Oct. 30, 2007

(65) Prior Publication Data

US 2010/0240145 A1 Sep. 23, 2010

Related U.S. Application Data

(60) Division of application No. 10/006,265, filed on Dec. 3, 2001, now Pat. No. 7,482,440, which is a continuation-in-part of application No. PCT/JP00/03556, filed on Jun. 1, 2000.

(30) Foreign Application Priority Data

Jun. 2, 1999 (JP) .................................... 11/155797
Jul. 30, 1999 (JP) .................................... 11/217797

(51) Int. Cl.
C07K 16/00 (2006.01)
C07K 16/18 (2006.01)
C07K 16/28 (2006.01)
C12P 21/08 (2006.01)

(52) U.S. Cl. ............... 530/387.9; 530/387.1; 530/387.3; 530/388.1; 530/388.22

(58) Field of Classification Search .............. 530/387.9, 530/387.1, 387.3, 388.1, 388.22
See application file for complete search history.

(56) References Cited

U.S. PATENT DOCUMENTS

| | | | |
|---|---|---|---|
| 6,642,360 B2 | 11/2003 | Filvaroff et al. |
| 6,747,137 B1 | 6/2004 | Weinstock et al. |
| 6,756,481 B2 | 6/2004 | Chirica et al. |
| 7,045,595 B2 | 5/2006 | Maeda et al. |
| 7,250,168 B2 | 7/2007 | Light et al. |
| 7,411,041 B2 | 8/2008 | Chirica et al. |
| 7,482,440 B2 | 1/2009 | Maeda et al. |
| 2003/0082734 A1 | 5/2003 | Dowling et al. |
| 2003/0125520 A1 | 7/2003 | Maeda et al. |
| 2003/0215838 A1 | 11/2003 | Sprecher et al. |
| 2006/0106201 A1 | 5/2006 | Maeda et al. |
| 2006/0166284 A1 | 7/2006 | Light et al. |
| 2006/0182743 A1 | 8/2006 | Bilsborough |
| 2007/0203328 A1 | 8/2007 | Maeda et al. |
| 2008/0019985 A1 | 1/2008 | Light et al. |
| 2008/0020965 A1 | 1/2008 | Light et al. |
| 2009/0023660 A1 | 1/2009 | Maeda et al. |
| 2009/0029484 A1 | 1/2009 | Maeda et al. |
| 2009/0105457 A1 | 4/2009 | Maeda et al. |
| 2009/0105458 A1 | 4/2009 | Maeda et al. |
| 2009/0105459 A1 | 4/2009 | Maeda et al. |
| 2009/0111972 A1 | 4/2009 | Maeda et al. |
| 2010/0016552 A1 | 1/2010 | Maeda et al. |
| 2010/0055092 A1 | 3/2010 | Hasegawa et al. |
| 2010/0240096 A1 | 9/2010 | Maeda et al. |

FOREIGN PATENT DOCUMENTS

| | | |
|---|---|---|
| EP | 0411946 | 2/1991 |
| EP | 0931646 | 7/1999 |
| EP | 1088831 | 4/2001 |
| EP | 1188830 | 3/2002 |
| JP | 2005-532045 | 10/2005 |
| WO | WO 95/33059 | 12/1995 |
| WO | WO 97/15663 | 1/1997 |
| WO | WO 97/07215 | 2/1997 |
| WO | WO 97/12037 | 3/1997 |
| WO | WO 00/73451 | 12/2000 |
| WO | WO 00/75314 | 12/2000 |
| WO | WO 01/23556 | 4/2001 |
| WO | WO 01/85790 | 11/2001 |
| WO | WO 02/00721 | 1/2002 |
| WO | WO 02/29060 | 4/2002 |
| WO | WO 02/077230 | 10/2002 |
| WO | WO 03/060090 | 7/2003 |
| WO | WO 03/072740 | 9/2003 |
| WO | WO 2004/003140 | 1/2004 |
| WO | WO 2006/063864 | 6/2006 |
| WO | WO 2006/081573 | 8/2006 |
| WO | WO 2006/088855 | 8/2006 |
| WO | WO 2006/088955 | 8/2006 |
| WO | WO 2006/088956 | 8/2006 |
| WO | WO 2006/122079 | 11/2006 |
| WO | 2007133816 A2 | 11/2007 |

OTHER PUBLICATIONS

Bazan, "Structural design and molecular evolution of a cytokine receptor superfamily," Proc. Natl. Acad. Sci. U.S.A., 87:6934-6938 (1990).
USPTO Notice of Allowance in U.S. Appl. No. 11/980,117, mailed Dec. 6, 2010, 8 pages.
Opposition filed on behalf of Mr. Martin MacLean against EP-B-1188830 in the name of Chugai Seiyaku Kabushiki Kaisha, dated Oct. 20, 2010, 17 pages.
Vaughan et al., "Human antibodies by design," Nature Biotechnology, 16(6):535-539 (1998). Fish & Richardson P.C Amendment in Reply to Action dated Jun. 4, 2009 in U.S. Appl. 11/595,320, filed Dec. 3, 2009, 13 pages.
USPTO Non-Final Office Action U.S. Appl. No. 12/205,799, mailed Feb. 8, 2010, 27 pages.
USPTO Non-Final Office Action in U.S. Appl. No. 12/325,556, mailed Jan. 28, 2010, 20 pages.
USPTO Non-Final Office Action in U.S. Appl. No. 12/325,591, mailed Dec. 7, 2009, 19 pages.

(Continued)

Primary Examiner — Anne Marie S Wehbe
(74) Attorney, Agent, or Firm — Fish & Richardson P.C.

(57) ABSTRACT

The inventors succeeded in isolating a novel hemopoietin receptor gene (NR10) using a sequence predicted from the extracted motif conserved in the amino acid sequences of known hemopoietin receptors. It was expected that two forms of NR10 exists, a transmembrane type and soluble form. Expression of the former type was detected in tissues containing hematopoietic cells. Thus, NR10 is a novel hemopoietin receptor molecule implicated in the regulation of the immune system and hematopoiesis in vivo. These novel receptors are useful in screening for novel hematopoietic factors capable of functionally binding to the receptor, or developing medicines to treat diseases related with the immune system or hematopoietic system.

21 Claims, 14 Drawing Sheets

OTHER PUBLICATIONS

USPTO Non-Final Office Action in U.S. Appl. No. 12/325,617, mailed Dec. 7, 2009, 19 pages.
USPTO Non-Final Office Action in U.S. Appl. No. 12/325,631, mailed Dec. 24, 2009, 21 pages.
Castellani et al., Interleukin-31: A New Cytokine Involved in Inflammation of the Skin, Int. J. of Immunopathol. and Pharmacol., 19(1):1-4 (2006).
Diveau et al., "Predominant expression of the long isoform of the GP130-like (GPL) receptor is required for interleukin-31 signaling," Eur. Cytokine Netw., 15(4):291-302 (2004).
USPTO Final Office Action in U.S. Appl. No. 11/595,320, mailed Mar. 19, 2010, 26 pages.
USPTO Non-Final Office Action in U.S. Appl. No. 12/205,753, mailed Mar. 5, 2010, 24 pages.
European Search Report for App. Ser. No. EP 07 74 4945, dated Oct. 29, 2009, 4 pages.
Fish & Richardson P.C. Reply to Office Action dated Dec. 7, 2009 in U.S. Appl. No. 12/325,591, filed Jun. 4, 2010, 9 pages.
Fish & Richardson P.C. Reply to Office Action dated Dec. 7, 2009 in U.S. Appl. No. 12/325,617, filed Jun. 4, 2010, 8 pages.
U.S. Appl. No. 11/980,117, filed Oct. 30, 2007, Maeda et al.
U.S. Appl. No. 12/253,506, filed Oct. 17, 2008, Maeda et al.
U.S. Appl. No. 12/303,684, filed Dec. 5, 2008, Hasegawa et al.
Bilsborough et al., "IL-31 is associated with cutaneous lymphocyte antigen-positive skin homing T cells in patients with atopic dermatitis," J. Allergy Clin. Immunol., 117(2):418-425 (2006).
Dillon et al., "Transgenic Mice Overexpressing a Novel Cytokine (IL-31) Develop a Severe Pruritic Skin Phenotype Resembling Atopic Dermatitis," Eur. Cytokine Netw., 14(suppl. 3):81 (#223) (2003).
Higa et al., "Administration of anti-interleukin 18 antibody fails to inhibit development of dermatitis in atopic dermatitis-model mice NC/Nga," Br. J. Dermatol., 149:39-45 (2003).
Irnaten et al., "Prediction of epitopes and production of monoclonal antibodies against gastric H,K-ATPase," Protein Engineering, 11(10):949-955 (1998).
Meinkoth and Wahl, "Hybridization of Nucleic Acids Immobilized on Solid Supports," Analytical Biochemistry, 138:267-284 (1984).
Nagata et al., "Novel IL-31 cytokine," Rheumatology, 35(3):282-286 (2006).
Sonkoly et al., "IL-31: a new link between T cells and pruritus in atopic skin inflammation," J. Allergy Clin. Immunol., 117(2):411-417 (2006).
Wells, "Additivity of Mutational Effects in Proteins," Biochem., 29:8509-8517 (1990).
USPTO Restriction Requirement in U.S. Appl. No. 10/105,930, mailed May 22, 2003, 6 pages.
Fish & Richardson P.C. Response to Restriction Requirement dated May 22, 2003 in U.S. Appl. No. 10/105,930, filed Jun. 17, 2003, 1 page.
USPTO Non-Final Office Action in U.S. Appl. No. 10/105,930, mailed Sep. 29, 2003, 19 pages.
Fish & Richardson P.C Amendment in Reply to Action dated Sep. 29, 2003 in U.S. Appl. No. 10/105,930, filed Mar. 26, 2004, 31 pages.
USPTO Final Office Action in U.S. Appl. No. 10/105,930, mailed Jun. 28, 2004, 16 pages.
Fish & Richardson P.C Amendment in Reply to Action dated Jun. 28, 2004 in U.S. Appl. No. 10/105,930, filed Nov. 23, 2004, 34 pages.
USPTO Advisory Action in U.S. Appl. No. 10/105,930, mailed Feb. 4, 2005, 4 pages.
Fish & Richardson P.C Appeal Brief in U.S. Appl. No. 10/105,930, filed Jun. 20, 2005, 27 pages.
USPTO Notice of Allowance in U.S. Appl. No. 10/105,930, mailed Sep. 14, 2005, 6 pages.
Japanese Patent Office, International Search Report for App. Ser. No. PCT/JP00/06654, mailed Dec. 26, 2000, 4 pages.
USPTO Non-Final Office Action in U.S. Appl. No. 11/274,375, mailed May 12, 2006, 17 pages.
USPTO Non-Final Office Action in U.S. Appl. No. 11/595,320, mailed Aug. 14, 2007, 14 pages.
Fish & Richardson P.C Amendment in Reply to Action dated Aug. 14, 2007 in U.S. Appl. No. 11/595,320, filed Feb. 14, 2008, 23 pages.
USPTO Non-Final Office Action in U.S. Appl. No. 11/595,320, mailed May 28, 2008, 13 pages.
Fish & Richardson P.C Amendment in Reply to Action dated May 28, 2008 in U.S. Appl. No. 11/595,320, filed Nov. 26, 2008, 6 pages.
USPTO Final Office Action in U.S. Appl. No. 11/595,320, mailed Feb. 26, 2009, 10 pages.
Fish & Richardson P.C Amendment in Reply to Action dated Feb. 26, 2009 in U.S. Appl. No. 11/595,320, filed Apr. 24, 2009, 3 pages.
USPTO Non-Final Office Action in U.S. Appl. No. 11/595,320, mailed Jun. 4, 2009, 10 pages.
USPTO Restriction Requirement in U.S. Appl. No. 10/006,265, mailed Dec. 13, 2004, 10 pages.
Fish & Richardson P.C. Response to Restriction Requirement dated Dec. 13, 2004 in U.S. Appl. No. 10/006,265, filed Jan. 10, 2005, 1 page.
USPTO Non-Final Office Action in U.S. Appl. No. 10/006,265, mailed Mar. 14, 2005, 8 pages.
Fish & Richardson P.C. Amendment in Reply to Action dated Mar. 14, 2005 in U.S. Appl. No. 10/006,265, filed Sep. 14, 2005, 33 pages.
USPTO Final Office Action in U.S. Appl. No. 10/006,265, mailed Dec. 21, 2005, 12 pages.
USPTO Non-Final Office Action in U.S. Appl. No. 10/006,265, mailed Jul. 26, 2006, 13 pages.
Fish & Richardson P.C. Amendment in Reply to Action dated Jul. 26, 2006 in U.S. Appl. No. 10/006,265, filed Jan. 5, 2007, 22 pages.
USPTO Final Office Action in U.S. Appl. No. 10/006,265, mailed Mar. 22, 2007, 9 pages.
Fish & Richardson P.C. Amendment in Reply to Action dated Mar. 22, 2007 in U.S. Appl. No. 10/006,265, filed Jun. 22, 2007, 7 pages.
USPTO Advisory Action in U.S. Appl. No. 10/006,265, mailed Jul. 30, 2007, 7 pages.
USPTO Non-Final Action in U.S. Appl. No. 10/006,265, mailed Oct. 30, 2007, 8 pages.
Fish & Richardson P.C. Amendment in Reply to Action dated Oct. 30, 2007 in U.S. Appl. No. 10/006,265, filed Jan. 30, 2008, 6 pages.
USPTO Notice of Allowance in U.S. Appl. No. 10/006,265, mailed Apr. 11, 2008, 15 pages.
Fish & Richardson P.C. Response to Notice of Allowance dated Apr. 11, 2008 in U.S. Appl. No. 10/006,265, filed Jul. 10, 2008, 6 pages.
Japanese Patent Office, International Search Report for App. Ser. No. PCT/JP2007/061625, mailed Sep. 18, 2007, 2 pages.
International Bureau of WIPO, International Preliminary Report on Patentability for App. Ser. No. PCT/JP2007/061625, dated Jan. 13, 2009, 11 pages.
USPTO Restriction Requirement in U.S. Appl. No. 12/325,591, mailed Aug. 25, 2009, 7 pages.
USPTO Restriction Requirement in U.S. Appl. No. 12/325,631, mailed Aug. 25, 2009, 7 pages.
USPTO Restriction Requirement in U.S. Appl. No. 12/325,556, mailed Aug. 25, 2009, 7 pages.
USPTO Restriction Requirement in U.S. Appl. No. 12/325,617, mailed Aug. 26, 2009, 7 pages.
Fish & Richardson P.C. Amendment in Reply to Action dated Feb. 8, 2010 in U.S. Appl. No. 12/205,799, filed Aug. 5, 2010, 6 pages.
Fish & Richardson P.C. Amendment in Reply to Action dated Jan. 28, 2010 in U.S. Appl. No. 12/325,556, filed Jul. 27, 2010, 4 pages.
Fish & Richardson P.C. Amendment in Reply to Action dated Dec. 24, 2009 in U.S. Appl. No. 12/325,631, filed Jun. 23, 2010, 10 pages.
USPTO Non-Final Office Action in U.S. Appl. No. 12/325,631, mailed Sep. 1, 2010, 9 pages.
USPTO Restriction Requirement in U.S. Appl. No. 12/303,684, mailed Aug. 23, 2010, 7 pages.
Fish & Richardson P.C. Amendment and Response to Restriction Requirement dated Aug. 23, 2010 in U.S. Appl. No. 12/303,684, filed Sep. 15, 2010, 3 pages.
Phillips, "The challenge of gene therapy and DNA delivery," J. Pharm. Pharmacol., 53(9):1169-1174 (2001).
Pirollo et al., "Targeted delivery of small interfering RNA: approaching effective cancer therapies," Cancer Res., 68(5):1247-1250 (2008).
Vidal et al., "Making sense of antisense," Eur. J. Cancer, 41(18):2812-2818 (2005).

Fish & Richardson P.C Amendment in Reply to Action dated Mar. 19, 2010 in U.S. Appl. No. 11/595,320, filed Sep. 17, 2010, 5 pages.
USPTO Notice of Allowance in U.S. Appl. No. 11/595,320, mailed Oct. 8, 2010, 4 pages.
USPTO Non-Final Office Action in U.S. Appl. No. 12/325,556, mailed Oct. 15, 2010, 8 pages.
USPTO Non-Final Office Action in U.S. Appl. No. 12/325,591, mailed Oct. 15, 2010, 8 pages.
USPTO Non-Final Office Action in U.S. Appl. No. 12/325,617, mailed Oct. 15, 2010, 8 pages.
USPTO Non-Final Office Action in U.S. Appl. No. 12/303,684, mailed Oct. 14, 2010, 18 pages.
USPTO Restriction Requirement in U.S. Appl. No. 12/205,799, mailed Oct. 9, 2009, 7 pages.
USPTO Restriction Requirement in U.S. Appl. No. 12/205,753, mailed Oct. 9, 2009, 7 pages.
Fish & Richardson P.C. Reply to Restriction Requirement dated Aug. 25, 2009 in U.S. Appl. No. 12/325,556, filed Sep. 21, 2009, 1 page.
Fish & Richardson P.C. Reply to Restriction Requirement dated Aug. 25, 2009 in U.S. Appl. No. 12/325,591, filed Sep. 21, 2009, 1 page.
Fish & Richardson P.C. Reply to Restriction Requirement dated Aug. 26, 2009 in U.S. Appl. No. 12/325,617, filed Sep. 21, 2009, 1 page.
Fish & Richardson P.C. Reply to Restriction Requirement dated Aug. 25, 2009 in U.S. Appl. No. 12/325,631, filed Sep. 21, 2009, 1 page.
Fish & Richardson P.C. Reply to Restriction Requirement dated Oct. 9, 2009 in U.S. Appl. No. 12/205,799, filed Nov. 4, 2009, 1 page.
Fish & Richardson P.C. Reply to Restriction Requirement dated Oct. 9, 2009 in U.S. Appl. No. 12/205,753, filed Nov. 4, 2009, 1 page.
Abbas et al., Cellular and Molecular Immunology, Second edition, W.B. Saunders Co., Philadelphia, pp. 47-48, 1994.
Alexander et al., "Suckling defect in mice lacking the soluble haemopoietin receptor NR6", Current Biology 9(11):605-608, 1999.
Baumgartner et al., "The role of the WSXWS equivalent motif in growth hormone receptor function", Journal of Biological Chemistry 269(46):29094-29101, 1994.
Bepler et al., A 1.4-Mb high-resolution physical map and contig of chromosome segment 11p15.5 and genes in LOH11A metastasis suppressor region, Genomics 55(2):164-175, 1991.
Bork et al., "Go hunting in sequence databases but watch out for the traps", Trends in Genetics 12:425-427, 1996.
Bork, "Powers and Pitfalls in Sequence Analysis: The 70% Hurdle", Genome Research 10:398-400, 2000.
Cioffi et al., "Novel B219/OB receptor isoforms: Possible role of leptin in hematopoiesis and reproduction", Nature Medicine 2(5):585-589, 1996.
Cosman, "A new cytokine receptor superfamily", Trends Biochem. Sci. 15:265-270, 1990.
Cosman, "The Hematopoietin Receptor Superfamily", Cytokine 5:95-106, 1993.
Dillon et al., "Interleukin 31, a cytokine produced by activated T cells, induces dermatitis in mice", Nature Immunology 5(7):752-760, 2004.
Diveu et al., "GPL, a novel cytokine receptor related to gp130 and leukemia inhibitory factor receptor", J. Biol. Chem. 278(50):49850-49859, 2003.
Donaldson et al. "The murine IL-13 receptor α2: Molecular cloning, characterization, and comparison with murine IL-13 receptor α2". The Journal of Immunology 161:2317-2324, 1998.
EMBL Accession No. AI123586 dated Sep. 8, 1998.
EMBL Accession No. W16834 dated May 4, 1996.
Gainsford et al., "Leptin can induce proliferation, differentiation, and functional activation of hemopoietic cells", Proc. Natl. Acad. Sci. USA 93:14564-14568, 1996.
Genbank Accession No. AAM44229 (hIL-23R), Oct. 19, 2004.
GenBank Accession No. AF102051, Jan. 28, 1999.
Genbank Accession No. AY499342, Jul. 10, 2004.
Genbank Accession No. NM_139017, Aug. 3, 2005.
Genbank Accession No. AQ022781, Jun. 16, 1998.
Ghilardi et al., "A novel type I cytokine receptor is expressed on monocytes, signals proliferation, and activates STAT-3 and STAT-5", J. Biol. Chem. 27(19):16831-16836, 2002.

Hibi et al., "Molecular cloning and expression of an IL-6 signal transducer, gp130", Cell 63:1149-1157, 1990.
Hilton et al., "Cloning and characterization of a binding subunit of the interleukin 13 receptor that is also a component of the interleukin 4 receptor", Proc. Natl. Acad. Sci. USA 93:497-501, 1996.
Hilton et al., "Cloning of a murine IL-11 receptor α-chain; requirement for gp 130 for high affinity binding and signal transduction", The EMBO Journal 13(20):4765-4775, 1994.
Jabbour et al. "Expression of functional prolactin receptors in non-pregnant human endometrium: janus kinase-2, signal transducer...". J. Clin. Endocrinol. Metab. 83(7):2545-2553, 1998.
Kernebeck et al., "The signal transducer gp 130: solution structure of the carboxy-terminal domain of the cytokine receptor homology region", Protein Science 8(1):5-12, 1999.
Mahairas et al., "Sequence-tagged connectors: A sequence approach to mapping and scanning the human genome", Proc. Natl. Acad. Sci. USA 96(17):9730-9744, 1999.
Matsuno et al., "Treatment of rheumatoid synovitis with anti-reshaping human interleukin-6 receptor monoclonal antibody", Arthritis & Rheumatism 41(11):2014-2021, 1998.
Matthews et al., "A receptor tyrosine kinase specific to hematopoietic stem and progenitor cell-enriched populations", Cell 65:1143-1152, 1991.
Miyajima et al., "Cytokine receptors and signal transduction", Annu. Rev. Immunol. 10:295-331, 1992.
Miyazaki et al., "The integrity of the conserved 'WS motif' common to IL-2 and other cytokine receptors is essential for ligand binding and signal transduction", EMBO J. 10(11):3191-3197, 1991.
Murakami et al., "Critical cytoplasmic region of the interleukin 6 signal transducer gp130 is conserved in the cytokine receptor family", Proc. Natl. Acad. Sci. 88:11349-11353, 1991.
Nishimoto et al., "Improvement in Castleman's disease by humanized anti-interleukin-6 receptor antibody therapy", Blood 95(1):56-61, 2001.
Nishimoto et al., "Toxicity, pharmacokinetics, and dose-finding study of repetitive treatment with the humanized anti-interleukin 6 receptor antibody MRA in rheumatoid arthritis. Phase I/II clinical study", J. Rheumatology 30(7):1426-1435, 2003.
Oppmann et al., "Novel p19 protein engages IL-12p40 to form a cytokine, IL-23, with biological activities similar as well as distinct from IL-12", Immunity 13:715-725, 2000.
Ozaki et al., "Cytokine receptor pleiotropy and redundancy", J. Biol. Chem 277:29355-29356, 2002.
Parham, et al., "A receptor for the heterodimeric cytokine IL-23 is composed of IL-12Rβ1 and a novel cytokine receptor subunit, IL-23R", The Journal of Immunology 168:5699-5708, 2002.
Robb et al., "Structural analysis of the gene encoding the murine interleukin-11 receptor α-chain and a related locus", J. Biol. Chem. 271(23):13754-13761, 1996.
Saito et al., "Molecular closing of a murine IL-6 receptor-associated signal transducer, gp130, and its regulated expression in vivo", J. Immunology 148(12):4066-4071, 1992.
Sato et al., "Reshaping a human antibody to inhibit the interleukin 6-dependent tumor cell growth", Cancer Research 53:851-856, 1993.
Simard et al., "Ontogeny of Growth hormone receptors in human tissues: an immunohistochemical study", Journal of Clinical Endocrinology and Metabolism 81(8):3097-3102, 1996.
Wells et al., "Hematopoietic receptor complexes", Annu. Rev. Biochem. 65:609-634, 1996.
Waters, "Degradation of Mutant Proteins, Underlying 'Loss of Function' Phenotypes, Plays a Major Role in Genetic Disease," *Curr. Issues Mol. Biol.*, 3(3):57-65 (2001).
Zhukov et al., "Conservative mutation Met8 →Leu affects the folding process and structural stability of squash trypsin inhibitor CMTI-I," *Protein Sci.*, 9:273-279 (2000).
USPTO Notice of Allowance in U.S. Appl. No. 11/980,117, mailed Feb. 2, 2011, 7 pages.
USPTO Non-Final Office Action in U.S. Appl. No. 12/253,506, mailed Mar. 14, 2011, 18 pages.
European Patent Office, Extended European Search Report including the International Search Report and Search Opinion that was issued in European Patent Appl. No. 10180785.7 (mail date of: Apr. 27, 2011), 8 pages.

Figure 1

```
  1    ttggtggttcatggtgatgttctatatctgtgtaagtaccaattgttcccaggcacatat
 61    ggaagtctgttaataaaaatgatatattttaaaatttgatttagagtgttactagttcta
121    aaaatgtaaaagtacactaggtagtgaagaggaaaatgggaggataacgtgtggtctcca
181    tttcagtttacgattgtctctgtcttgtagatggaagtcaacttcgctaagaaccgtaag
                                        MetGluValAsnPheAlaLysAsnArgLys 241    gataaaaaccaaacgtacaacctcacggggctgcaacctt[n]tacagaatatgtcatagct
       AspLysAsnGlnThrTyrAsnLeuThrGlyLeuGlnProXxxThrGlu[TyrValIleAla]

301    ctgcgatgtgcggtcaaggagtcaaagttctggagtgactggagccaagaaaaaatggga
       [LeuArg]CysAlaValLysGluSerLysPhe[TrpSerAspTrpSer]GlnGluLysMetGly 361    atgactgaggaagaa[n]gcaagctacttcctgcgattcccgtcctgtctgctctggtgtan
       MetThrGluGluGluXxxLysLeuLeuProAlaIlePro 421    ggctgctctgcgctaaacttggtggtgtctgcaccaccg
```

Figure 2

```
                 *              *****
hNR10   TYNLTGLQPFTEYVIALRCAVKESK-FWSDWSQEKMGMTEEE
gp130   SFTVQDLKPFTEYVFRIRCMKEDGKGYWSDWSEEASGITYED

*              *****
hNR10   LTGLQPFTEYVIALRCAVKESKFWSDWSQEKMGMTEE
hLIFR   LDKLNPYTLYTFRIRCSTETFWKWSKWSNKKQHLTTE

*               *****
hNR10   NQTYNLTGLQPFTEYVIALRCAVKESKF--WSDWSQEKMGMTEE
OSMRB   NGEYFLSELEPATEYMARVRCA-DASHFWKWSEWSGQNFT-TLE

*                *****
hNR10   AKNRKDKNQTYNLTGLQPFTEYVIALRCAVKESK-FWSDWSQEKMGMTEEE
IL12R   AKGRHD------LLDLKPFTEYEFQISSKLHLYKGSWSDWSESLRAQTPEE

*                 *****
hNR10   NQTY-NLTGLQPFTEYVIALRC------AVKESKFWSDWSQEKMGMTEEEG
hNR 6   NQTSCRLAGLKPGTVYFVQVRCNPFGIYGSKKAGIWSEWSHPTAASTPRSG
```

Figure 3

```
   1  CGCTTATAAATGAATGTGTGCTTAGGAACACCAGACAGCACTCCAGCACTCTGCTTGGGG
  61  GGCATTCGAAACAGCAAAATCACTCATAAAAGGCAAAAAATTGCAAAAAAAATAGTAATA
 121  ACCAGCATGGTACTAAATAGACCATGAAAAGACATGTGTGTGCAGTATGAAAATTGAGAC
 181  AGGAAGGCAGAGTGTCAGCTTGTTCCACCTCAGCTGGGAATGTGCATCAGGCAACTCAAG
 241  TTTTTCACCACGGCATGTGTCTGTGAATGTCCGCAAAACATTTTAACAATAATGCAATCC
 301  ATTTCCCAGCATAAGTGGGTAAGTGCCACTTTGACTTGGGCTGGGCTTAAAAGCACAAGA
 361  AAAGCTCGCAGACAATCAGAGTGGAAACACTCCCACATCTTAGTGTGGATAAATTAAAGT
 421  CCAGATTGTTCTTCCTGTCCTGACTTGTGCTGTGGGAGGTGGAGTTGCCTTTGATGCAAA
 481  TCCTTTGAGCCAGCAGAACATCTGTGGAACATCCCCTGATACATGAAGCTCTCTCCCCAG
                                                    MetLysLeuSerProGln
 541  CCTTCATGTGTTAACCTGGGGATGATGTGGACCTGGGCACTGTGGATGCTCCCCTCACTC
         ProSerCysValAsnLeuGlyMetMetTrpThrTrpAlaLeuTrpMetLeuProSerLeu
 601  TGCAAATTCAGCCTGGCAGCTCTGCCAGCTAAGCCTGAGAACATTTCCTGTGTCTACTAC
         CysLysPheSerLeuAlaAlaLeuProAlaLysProGluAsnIleSer[Cys]ValTyrTyr
 661  TATAGGAAAAATTTAACCTGCACTTGGAGTCCAGGAAAGGAAACCAGTTATACCCAGTAC
         TyrArgLysAsnLeuThr[Cys]ThrTrpSerProGlyLysGluThrSerTyrThrGlnTyr
 721  ACAGTTAAGAGAACTTACGCTTTCGGAGAAAAACATGATAATTGTACAACCAATAGTTCT
         ThrValLysArgThrTyrAlaPheGlyGluLysHisAspAsn[Cys]ThrThrAsnSerSer
 781  ACAAGTGAAAATCGTGCTTCGTGCTCTTTTTTCCTTCCAAGAATAACGATCCCAGATAAT
         ThrSerGluAsnArgAlaSer[Cys]SerPhePheLeuProArgIleThrIleProAspAsn
 841  TATACCATTGAGGTGGAAGCTGAAAATGGAGATGGTGTAATTAAATCTCATATGACATAC
         TyrThrIleGluValGluAlaGluAsnGlyAspGlyValIleLysSerHisMetThrTyr
 901  TGGAGATTAGAGAACATAGCGAAAACTGAACCACCTAAGATTTTCCGTGTGAAACCAGTT
         TrpArgLeuGluAsnIleAlaLysThrGluProProLysIlePheArgValLysProVal
 961  TTGGGCATCAAACGAATGATTCAAATTGAATGGATAAAGCCTGAGTTGGCGCCTGTTTCA
         LeuGlyIleLysArgMetIleGlnIleGluTrpIleLysProGluLeuAlaProValSer
1021  TCTGATTTAAAATACACACTTCGATTCAGGACAGTCAACAGTACCAGCTGGATGGAAGTC
         SerAspLeuLysTyrThrLeuArgPheArgThrValAsnSerThrSerTrpMetGluVal
1081  AACTTCGCTAAGAACCGTAAGGATAAAAACCAAACGTACAACCTCACGGGGCTGCAGCCT
         AsnPheAlaLysAsnArgLysAspLysAsnGlnThrTyrAsnLeuThrGlyLeuGlnPro
1141  TTTACAGAATATGTCATAGCTCTGCGATGTGCGGTCAAGGAGTCAAAGTTCTGGAGTGAC
         PheThrGluTyrValIleAlaLeuArgCysAlaValLysGluSerLysPhe[TrpSerAsp]
```

Figure 4

```
1201  TGGAGCCAAGAAAAAATGGGAATGACTGAGGAAGAAGCTCCATGTGGCCTGGAACTGTGG
      TrpSerGlnGluLysMetGlyMetThrGluGluGluAlaProCysGlyLeuGluLeuTrp
1261  AGAGTCCTGAAACCAGCTGAGGCGGATGGAAGAAGGCCAGTGCGGTTGTTATGGAAGAAG
      ArgValLeuLysProAlaGluAlaAspGlyArgArgProValArgLeuLeuTrpLysLys
1321  GCAAGAGGAGCCCCAGTCCTAGAGAAAACACTTGGCTACAACATATGGTACTATCCAGAA
      AlaArgGlyAlaProValLeuGluLysThrLeuGlyTyrAsnIleTrpTyrTyrProGlu
1381  AGCAACACTAACCTCACAGAAACAATGAACACTACTAACCAGCAGCTTGAACTGCATCTG
      SerAsnThrAsnLeuThrGluThrMetAsnThrThrAsnGlnGlnLeuGluLeuHisLeu
1441  GGAGGCGAGAGCTTTTGGGTGTCTATGATTTCTTATAATTCTCTTGGAAGTCTCCAGTG
      GlyGlyGluSerPheTrpValSerMetIleSerTyrAsnSerLeuGlyLysSerProVal
1501  GCCACCCTGAGGATTCCAGCTATTCAAGAAAAATCATTTCAGTGCATTGAGGTCATGCAG
      AlaThrLeuArgIleProAlaIleGlnGluLysSerPheGlnCysIleGluValMetGln
1561  GCCTGCGTTGCTGAGGACCAGCTAGTGGTGAAGTGGCAAAGCTCTGCTCTAGACGTGAAC
      AlaCysValAlaGluAspGlnLeuValValLysTrpGlnSerSerAlaLeuAspValAsn
1621  ACTTGGATGATTGAATGGTTTCCGGATGTGGACTCAGAGCCCACCACCCTTTCCTGGGAA
      ThrTrpMetIleGluTrpPheProAspValAspSerGluProThrThrLeuSerTrpGlu
1681  TCTGTGTCTCAGGCCACGAACTGGACGATCCAGCAAGATAAATTAAAACCTTTCTGGTGC
      SerValSerGlnAlaThrAsnTrpThrIleGlnGlnAspLysLeuLysProPheTrpCys
1741  TATAACATCTCTGTGTATCCAATGTTGCATGACAAAGTTGGCGAGCCATATTCCATCCAG
      TyrAsnIleSerValTyrProMetLeuHisAspLysValGlyGluProTyrSerIleGln
1801  GCTTATGCCAAAGAAGGCGTTCCATCAGAAGGTCCTGAGACCAAGGTGGAGAACATTGGC
      AlaTyrAlaLysGluGlyValProSerGluGlyProGluThrLysValGluAsnIleGly
1861  GTGAAGACGGTCACGATCACATGGAAAGAGATTCCCAAGAGTGAGAGAAAGGGTATCATC
      ValLysThrValThrIleThrTrpLysGluIleProLysSerGluArgLysGlyIleIle
1921  TGCAACTACACCATCTTTTACCAAGCTGAAGGTGGAAAAGGATTCTCCAAGACAGTCAAT
      CysAsnTyrThrIlePheTyrGlnAlaGluGlyGlyLysGlyPheSerLysThrValAsn
1981  TCCAGCATCTTGCAGTACGGCCTGGAGTCCCTGAAACGAAAGACCTCTTACATTGTTCAG
      SerSerIleLeuGlnTyrGlyLeuGluSerLeuLysArgLysThrSerTyrIleValGln
2041  GTCATGGCCAACACCAGTGCTGGGGGAACCAACGGGACCAGCATAAATTTCAAGACATTG
      ValMetAlaAsnThrSerAlaGlyGlyThrAsnGlyThrSerIleAsnPheLysThrLeu
2101  TCATTCAGTGTCTTTGAGATTATCCTCATAACTTCTCTGATTGGTGGAGGCCTTCTTATT
      SerPheSerValPheGluIleIleLeuIleThrSerLeuIleGlyGlyGlyLeuLeuIle
```

Figure 5

```
2161 CTCATTATCCTGACAGTGGCATATGGTCTCAAAAAACCCAACAAATTGACTCATCTGTGT
     LeuIleIleLeuThrValAlaTyrGlyLeuLysLysProAsnLysLeuThrHisLeuCys
2221 TGGCCCACCGTTCCCAACCCTGCTGAAAGTAGTATAGCCACATGGCATGGAGATGATTTC
     TrpProThrValProAsnProAlaGluSerSerIleAlaThrTrpHisGlyAspAspPhe
2281 AAGGATAAGCTAAACCTGAAGGAGTCTGATGACTCTGTGAACACAGAAGACAGGATCTTA
     LysAspLysLeuAsnLeuLysGluSerAspAspSerValAsnThrGluAspArgIleLeu
2341 AAACCATGTTCCACCCCCAGTGACAAGTTGGTGATTGACAAGTTGGTGGTGAACTTTGGG
     LysProCysSerThrProSerAspLysLeuValIleAspLysLeuValValAsnPheGly
2401 AATGTTCTGCAAGAAATTTTCACAGATGAAGCCAGAACGGGTCAGGAAAAACAATTTAGG
     AsnValLeuGlnGluIlePheThrAspGluAlaArgThrGlyGlnGluLysGlnPheArg
2461 AGGGGAAAAGAATGGGACTAGAATTCTGTCTTCCTGCCCAACTTCAATATAAGTGTGGAC
     ArgGlyLysGluTrpAsp***
2521 TAAAATGCGAGAAAGGTGTCCTGTGGTCTATGCAAATTAGAAAGGACATGCAGAGTTTTC
2581 CAACTAGGAAGACTGAATCTGTGGCCCCAAGAGAACCATCTCCGAAGACTGGGTATGTGG
2641 TCTTTTCCACACATGGACCACCTACGGATGCAATCTGTAATGCATGTGCATGAGAAGTCT
2701 GTTATTAAGTAGAGTGTGAAAACATGGTTATGGTAATAGGAACAGCTTTTAAAATGCTTT
2761 TGTATTTGGGCCTTTCACACAAAAAAGCCATAATACCATTTTCATGTAATGCTATACTTC
2821 TATACTATTTTCATGTAATACTATACTTCTATACTATTTTCATGTAATACTATACTTCTA
2881 TACTATTTTCATGTAATACTATACTTCTATATTAAAGTTTTACCCACTCCAAAAAAGAA
2941 AAAAAAAAAAAAAAAAAAAAAAAAAA
```

Figure 6

```
   1  CGCTTATAAATGAATGTGTGCTTAGGAACACCAGACAGCACTCCAGCACTCTGCTTGGGG
  61  GGCATTCGAAACAGCAAAATCACTCATAAAAGGCAAAAAATTGCAAAAAAAATAGTAATA
 121  ACCAGCATGGTACTAAATAGACCATGAAAAGACATGTGTGTGCAGTATGAAAATTGAGAC
 181  AGGAAGGCAGAGTGTCAGCTTGTTCCACCTCAGCTGGGAATGTGCATCAGGCAACTCAAG
 241  TTTTTCACCACGGCATGTGTCTGTGAATGTCCGCAAAACATTTTAACAATAATGCAATCC
 301  ATTTCCCAGCATAAGTGGGTAAGTGCCACTTTGACTTGGGCTGGGCTTAAAAGCACAAGA
 361  AAAGCTCGCAGACAATCAGAGTGGAAACACTCCCACATCTTAGTGTGGATAAATTAAAGT
 421  CCAGATTGTTCTTCCTGTCCTGACTTGTGCTGTGGGAGGTGGAGTTGCCTTTGATGCAAA
 481  TCCTTTGAGCCAGCAGAACATCTGTGGAACATCCCCTGATACATGAAGCTCTCTCCCCAG
                                                    MetLysLeuSerProGln
 541  CCTTCATGTGTTAACCTGGGGATGATGTGGACCTGGGCACTGTGGATGCTCCCCTCACTC
      ProSerCysValAsnLeuGlyMetMetTrpThrTrpAlaLeuTrpMetLeuProSerLeu
 601  TGCAAATTCAGCCTGGCAGCTCTGCCAGCTAAGCCTGAGAACATTTCCTGTGTCTACTAC
      CysLysPheSerLeuAlaAlaLeuProAlaLysProGluAsnIleSer Cys ValTyrTyr
 661  TATAGGAAAAATTTAACCTGCACTTGGAGTCCAGGAAAGGAAACCAGTTATACCCAGTAC
      TyrArgLysAsnLeuThr Cys ThrTrpSerProGlyLysGluThrSerTyrThrGlnTyr
 721  ACAGTTAAGAGAACTTACGCTTTCGGAGAAAAACATGATAATTGTACAACCAATAGTTCT
      ThrValLysArgThrTyrAlaPheGlyGluLysHisAspAsn Cys ThrThrAsnSerSer
 781  ACAAGTGAAAATCGTGCTTCGTGCTCTTTTTTCCTTCCAAGAATAACGATCCCAGATAAT
      ThrSerGluAsnArgAlaSer Cys SerPhePheLeuProArgIleThrIleProAspAsn
 841  TATACCATTGAGGTGGAAGCTGAAAATGGAGATGGTGTAATTAAATCTCATATGACATAC
      TyrThrIleGluValGluAlaGluAsnGlyAspGlyValIleLysSerHisMetThrTyr
 901  TGGAGATTAGAGAACATAGCGAAAACTGAACCACCTAAGATTTTCCGTGTGAAACCAGTT
      TrpArgLeuGluAsnIleAlaLysThrGluProProLysIlePheArgValLysProVal
 961  TTGGGCATCAAACGAATGATTCAAATTGAATGGATAAAGCCTGAGTTGGCGCCTGTTTCA
      LeuGlyIleLysArgMetIleGlnIleGluTrpIleLysProGluLeuAlaProValSer
1021  TCTGATTTAAAATACACACTTCGATTCAGGACAGTCAACAGTACCAGCTGGATGGAAGTC
      SerAspLeuLysTyrThrLeuArgPheArgThrValAsnSerThrSerTrpMetGluVal
1081  AACTTCGCTAAGAACCGTAAGGATAAAAACCAAACGTACAACCTCACGGGGCTGCAGCCT
      AsnPheAlaLysAsnArgLysAspLysAsnGlnThrTyrAsnLeuThrGlyLeuGlnPro
1141  TTTACAGAATATGTCATAGCTCTGCGATGTGCGGTCAAGGAGTCAAAGTTCTGGAGTGAC
      PheThrGluTyrValIleAlaLeuArgCysAlaValLysGluSerLysPhe TrpSerAsp
```

Figure 7

```
1201  TGGAGCCAAGAAAAAATGGGAATGACTGAGGAAGAAGGCAAGCTACTCCCTGCGATTCCC
          TrpSer GlnGluLysMetGlyMetThrGluGluGluGlyLysLeuLeuProAlaIlePro
1261  GTCCTGTCTACTCTGGTGTAGGGCTGCTTTGGGCTAGACTTGGTGGGGTTTGTCACCACC
          ValLeuSerThrLeuVal***
1321  TGGTTGGGAATCATGGAATCTCATGACCCCAGGGGCCCCCTGTACCATCGAGAGTGAGCC
1381  TGCACAACTTTGTGCCCCAAAGGCAAAGGATCACATTTTAATACTCATGAGGTTCTTATA
1441  CTATACATGAAAGGGTATCATATCATTTGTTTTGTTTTGTTTTGTTTTTGAGATGGAGTC
1501  TTACTCTGTCACCCAGGATGGAGTGCAGTGATGTGATCTCGGCTCACTGCCACCACCACC
1561  TCCCGAGTTCAAGCAATTCTTGTGCCTCAGCCTCCCAAGTAGCTGGGATTACAGGGGCCC
1621  ACGACCATGCCCGGTTGATTTTTGTATTTTTAGTAGAGAAGGGATATCACCATGTTGGCT
1681  AGGCTAGTCTTGAACTCCTGACCTCAGGTAATCTGCCCACCTTGACCTCCCAAAGTGTTG
1741  GGATTACAGGCGTGAGCCACTGTGCCCCGCCAGTATCATATCATCTGAAGGTATCCTGTG
1801  ATAAATTAAAGATACATATTGTGAATCCTGGAGCTACTACTCAAAAAATAAATAAAGGTG
1861  TAACTAATACAATTTAAAAAATCACATTTTTAATGACAGTGAGGAAAGGAAAGAGGCATG
1921  GATTGCAGGTTGATGGAGTGCTTACTAAGTGTCAGTATGGTCATTAAGAGCAACGCTTCC
1981  AGTCAGTGGCCTTGGCTTAAATCCCAAGCCAGGTGTCTTTGGGCAAGATACCTAAACTCT
2041  CAGTTCATTCTCAGCAGTTTCCTCGCATTTATTCCCCTTTTCTATATTGAAATAGAATAT
2101  GTAAGTTGAGTTTATAGTAGTACCTATTTTTAGTATTATTTTAAAGATTAAATGAAATA
2161  ATGTGTTTAGCCCATAGTAGATATTCACTAACTGCTAGACTTCCTATTCTTATTATTTAT
2221  CCTCCTACTATTATTTTTAATCCTCCTTAAAGCACTATAAAATATGTAGAGTCACTCCCA
2281  TTTTGGAAATGAGGAAACTGAGTTTCAGAGATGCTAATAAACAGCTCAGGGTCACTCAGC
2341  ATGTGTTACTTTTCTCAAGAGCCTTGCCCAGAGTCTGACCCTCAGTGGACGATCAATAAA
2401  TGTGTGATGAATGGAAAAAAAAAAAAAAAAAAAAAAAAA
```

Fetal Thymus
Fetal Spleen
Fetal Skeletal Muscle
Fetal Lung
Fetal Liver
Fetal Kidney
Fetal Heart
Fetal Brain
Colon
Small Intestine
Ovary
Testis
Prostate
Pancreas
Kidney
Skeletal Muscle
Liver
Lung
Placenta
Brain
Heart
Tonsil
Fetal Liver
Bone Marrow
PBL
Thymus
Lymphnode
Spleen Fetal Thymus
Fetal Spleen
Fetal Skeletal Muscle
Fetal Lung
Fetal Liver
Fetal Kidney
Fetal Heart
Fetal Brain
Colon
Small Intestine
Ovary
Testis
Prostate
Pancreas
Kidney
Skeletal Muscle
Liver
Lung
Placenta
Brain
Heart
Tonsil
Fetal Liver
Bone Marrow
PBL
Thymus
Lymphnode
Spleen Fetal Thymus
Fetal Spleen
Fetal Skeletal Muscle
Fetal Lung
Fetal Liver
Fetal Kidney
Fetal Heart
Fetal Brain
Colon
Small Intestine
Ovary
Testis
Prostate
Pancreas
Kidney
Skeletal Muscle
Liver
Lung
Placenta
Brain
Heart
Tonsil
Fetal Liver
Bone Marrow
PBL
Thymus
Lymphnode
Spleen Figure 12
pEF-NR10/TPO-R
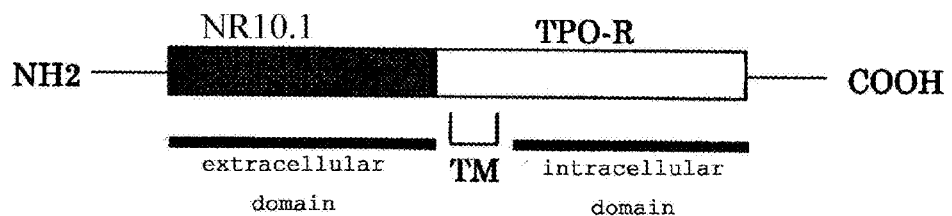
pET-NR10/IgG-Fc
pEF-BOS/NR10.2FLAG
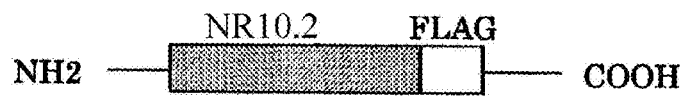

Figure 13

```
   1 CCCCTGATACATGAAGCTCTCTCCCCAGCCTTCATGTGTTAACCTGGGGATGATGTGGAC
                     MetLysSerProGlnProSerCysValAsnLeuGlyMetMetTrpThr
  61 CTGGGCACTGTGGATGCTCCCCTCACTCTGCAAATTCAGCCTGGCAGCTCTGCCAGCTAA
        TrpAlaLeuTrpMetLeuProSerLeuCysLysPheSerLeuAlaAlaLeuProAlaLys
 121 GCCTGAGAACATTTCCTGTGTCTACTACTATAGGAAAAATTTAACCTGCACTTGGAGTCC
        ProGluAsnIleSer[Cys]ValTyrTyrTyrArgLysAsnLeuThr[Cys]ThrTrpSerPro
 181 AGGAAAGGAAACCAGTTATACCCAGTACACAGTTAAGAGAACTTACGCTTTTGGAGAAAA
        GlyLysGluThrSerTyrThrGlnTyrThrValLysArgThrTyrAlaPheGlyGluLys
 241 ACATGATAATTGTACAACCAATAGTTCTACAAGTGAAATCGTGCTTCGTGCTCTTTTTT
        HisAspAsn[Cys]ThrThrAsnSerSerThrSerGluAsnArgAlaSer[Cys]SerPhePhe
 301 CCTTCCAAGAATAACGATCCCAGATAATTATACCATTGAGGTGGAAGCTGAAAATGGAGA
        LeuProArgIleThrIleProAspAsnTyrThrIleGluValGluAlaGluAsnGlyAsp
 361 TGGTGTAATTAAATCTCATATGACATACTGGAGATTAGAGAACATAGCGAAACTGAACC
        GlyValIleLysSerHisMetThrTyrTrpArgLeuGluAsnIleAlaLysThrGluPro
 421 ACCTAAGATTTTCCGTGTGAAACCAGTTTTGGGCATCAAACGAATGATTCAAATTGAATG
        ProLysIlePheArgValLysProValLeuGlyIleLysArgMetIleGlnIleGluTrp
 481 GATAAAGCCTGAGTTGGCGCCTGTTTCATCTGATTTAAAATACACACTTCGATTCAGGAC
        IleLysProGluLeuAlaProValSerSerAspLeuLysTyrThrLeuArgPheArgThr
 541 AGTCAACAGTACCAGCTGGATGGAAGTCAACTTCGCTAAGAACCGTAAGGATAAAAACCA
        ValAsnSerThrSerTrpMetGluValAsnPheAlaLysAsnArgLysAspLysAsnGln
 601 AACGTACAACCTCACGGGGCTGCAGCCTTTTACAGAATATGTCATAGCTCTGCGATGTGC
        ThrTyrAsnLeuThrGlyLeuGlnProPheThrGluTyrValIleAlaLeuArgCysAla
 661 GGTCAAGGAGTCAAAGTTCTGGAGTGACTGGAGCCAAGAAAAATGGGAATGACTGAGGA
        ValLysGluSerLysPhe[TrpSerAspTrpSer]GlnGluLysMetGlyMetThrGluGlu
 721 AGAAGCTCCATGTGGCCTGGAACTGTGGAGAGTCCTGAAACCAGCTGAGGCGGATGGAAG
        GluAlaProCysGlyLeuGluLeuTrpArgValLeuLysProAlaGluAlaAspGlyArg
 781 AAGGCCAGTGCGGTTGTTATGGAAGAAGGCAAGAGGAGCCCCAGTCCTAGAGAAAACACT
        ArgProValArgLeuLeuTrpLysLysAlaArgGlyAlaProValLeuGluLysThrLeu
 841 TGGCTACAACATATGGTACTATCCAGAAAGCAACACTAACCTCACAGAAACAATGAACAC
        GlyTyrAsnIleTrpTyrTyrProGluSerAsnThrAsnLeuThrGluThrMetAsnThr
 901 TACTAACCAGCAGCTTGAACTGCATCTGGGAGGCGAGAGCTTTTGGGTGTCTATGATTTC
        ThrAsnGlnGlnLeuGluLeuHisLeuGlyGlyGluSerPheTrpValSerMetIleSer
 961 TTATAATTCTCTTGGGAAGTCTCCAGTGGCCACCCTGAGGATTCCAGCTATTCAAGAAAA
        TyrAsnSerLeuGlyLysSerProValAlaThrLeuArgIleProAlaIleGlnGluLys
1021 ATCATTTCAGTGCATTGAGGTCATGCAGGCCTGCGTTGCTGAGGACCAGCTAGTGGTGAA
```

Figure 14

```
       SerPheGlnCysIleGluValMetGlnAlaCysValAlaGluAspGlnLeuValValLys
1081   GTGGCAAAGCTCTGCTCTAGACGTGAACACTTGGATGATTGAATGGTTTCCGGATGTGGA
       TrpGlnSerSerAlaLeuAspValAsnThrTrpMetIleGluTrpPheProAspValAsp
1141   CTCAGAGCCCACCACCCTTTCCTGGGAATCTGTGTCTCAGGCCACGAACTGGACGATCCA
       SerGluProThrThrLeuSerTrpGluSerValSerGlnAlaThrAsnTrpThrIleGln
1201   GCAAGATAAATTAAAACCTTTCTGGTGCTATAACATCTCTGTGTATCCAATGTTGCATGA
       GlnAspLysLeuLysProPheTrpCysTyrAsnIleSerValTyrProMetLeuHisAsp
1261   CAAAGTTGGCGAGCCATATTCCATCCAGGCTTATGCCAAAGAAGGCGTTCCATCAGAAGG
       LysValGlyGluProTyrSerIleGlnAlaTyrAlaLysGluGlyValProSerGluGly
1321   TCCTGAGACCAAGGTGGAGAACATTGGCGTGAAGACGGTCACGATCACATGGAAAGAGAT
       ProGluThrLysValGluAsnIleGlyValLysThrValThrIleThrTrpLysGluIle
1381   TCCCAAGAGTGAGAGAAAGGGTATCATCTGCAACTACACCATCTTTTACCAAGCTGAAGG
       ProLysSerGluArgLysGlyIleIleCysAsnTyrThrIlePheTyrGlnAlaGluGly
1441   TGGAAAAGGATTCTCCAAGACAGTCAATTCCAGCATCTTGCAGTACGGCCTGGAGTCCCT
       GlyLysGlyPheSerLysThrValAsnSerSerIleLeuGlnTyrGlyLeuGluSerLeu
1501   GAAACGAAAGACCTCTTACATTGTTCAGGTCATGGCCAGCACCAGTGCTGGGGGAACCAA
       LysArgLysThrSerTyrIleValGlnValMetAlaSerThrSerAlaGlyGlyThrAsn
1561   CGGGACCAGCATAAATTTCAAGACATTGTCATTCAGTGTCTTTGAGATTATCCTCATAAC
       GlyThrSerIleAsnPheLysThrLeuSerPheSerValPheGluIleIleLeuIleThr
1621   TTCTCTGATTGGTGGAGGCCTTCTTATTCTCATTATCCTGACAGTGGCATATGGTCTCAA
       SerLeuIleGlyGlyGlyLeuLeuIleLeuIleLeuThrValAlaTyrGlyLeuLys
1681   AAAACCCAACAAATTGACTCATCTGTGTTGGCCCACCGTTCCCAACCCTGCTGAAAGTAG
       LysProAsnLysLeuThrHisLeuCysTrpProThrValProAsnProAlaGluSerSer
1741   TATAGCCACATGGCATGGAGATGATTTCAAGGATAAGCTAAACCTGAAGGAGTCTGATGA
       IleAlaThrTrpHisGlyAspAspPheLysAspLysLeuAsnLeuLysGluSerAspAsp
1801   CTCTGTGAACACAGAAGACAGGATCTTAAAACCATGTTCCACCCCCAGTGACAAGTTGGT
       SerValAsnThrGluAspArgIleLeuLysProCysSerThrProSerAspLysLeuVal
1861   GATTGACAAGTTGGTGGTGAACTTTGGGAATGTTCTGCAAGAAATTTTCACAGATGAAGC
       IleAspLysLeuValValAsnPheGlyAsnValLeuGlnGluIlePheThrAspGluAla
1921   CAGAACGGGTCAGGAAAACAATTTAGGAGGGGAAAAGAATGGGACTAGAATTCTGTCTTC
       ArgThrGlyGlnGluAsnAsnLeuGlyGlyGluLysAsnGlyThrArgIleLeuSerSer
1981   CTGCCCAACTTCAATATAAGTGTGGACTAAAATGCGAGAAAGGTGTCCTGTGGTCTATGC
       CysProThrSerIle***
2041   AAATTAGAAAGGACATGCAGAGTTTTCCAACTAGGAAGACTGAATCTGTGGCCCCAAGAG

2101   AACCATCTCCGAAGACTGG
```

HEMOPOIETIN RECEPTOR PROTEIN, NR10

This application is a divisional of U.S. application Ser. No. 10/006,265, filed Dec. 3, 2001 now U.S. Pat. No. 7,482,440, which is a continuation-in-part of PCT/JP00/03556, filed Jun. 1, 2000, which claims priority to Japanese patent application Ser. No. 11/155,797, filed Jun. 2, 1999 and Japanese patent application Ser. No. 11/217,797, filed Jul. 30, 1999. Each of the prior applications is herein incorporated by reference.

TECHNICAL FIELD

The present invention relates to novel hemopoietin receptor proteins, and genes encoding them, as well as methods for producing and using the same.

BACKGROUND

A large number of cytokines are known as humoral factors that are involved in the proliferation/differentiation of various cells and the activation of functions of differentiated mature cells as well as cell death. There are specific receptors for these cytokines, which are categorized into several families based on their structural similarities (Hilton D. J., in "Guidebook to Cytokines and Their Receptors" edited by Nicola N. A. (A Sambrook & Tooze Publication at Oxford University Press), p 8-16, 1994).

On the other hand, as compared to the similarities of their receptors, the homology of the primary-structure among cytokines is quite low. No significant amino acid homology has been observed, even among cytokine members that belong to the same receptor family. This explains the functional specificity of respective cytokines, as well as the similarities among cellular reactions induced by each cytokine.

Representative examples of the above-mentioned receptor families are the tyrosine kinase receptor family, the hemopoietin receptor family, the tumor necrosis factor (TNF) receptor family, and the transforming growth factor β (TGF β) receptor family. Different signal transduction pathways have been reported to be involved in each of these families. Among these receptor families, many receptors of the hemopoietin receptor family in particular are expressed in blood cells or immunocytes, and their ligands, cytokines, are often termed as hemopoietic factors or interleukins. Some of these hemopoietic factors or interleukins exist within blood and are thought to be involved in systemic humoral regulation of hemopoietic or immune functions.

This contrasts with the belief that cytokines belonging to other families are often involved in only topical regulations. Some of these hemopoietins can be taken as hormone-like factors, and representative peptide hormones, such as the growth hormone, prolactin, or leptin receptors, also belong to the hemopoietin receptor family. Because of these hormone-like systemic regulatory features, it is anticipated that administration of these hemopoietins can be applied to the treatment of various diseases.

Among the large number of cytokines, those that are presently being clinically applied include erythropoietin, G-CSF, GM-CSF, and IL-2. Combined with IL-11, LIF, and IL-12 that are currently under consideration for clinical trials, and the above-mentioned peptide hormones, such as growth hormone and prolactin, it can be envisaged that by searching novel cytokines that bind to hemopoietin receptors among the above-mentioned various receptor families, it is possible to find a cytokine that can be clinically applied with a higher efficiency.

As mentioned above, cytokine receptors share structural similarities among the family members. Using these similarities, many investigations are aimed at finding novel receptors. In particular, many receptors of the tyrosine kinase receptor family have already been cloned, using its highly conserved sequence at the catalytic site (Matthews et al., Cell, 65:1143-52, 1991). In comparison, hemopoietin receptors do not have a tyrosine kinase-like enzyme activity domain in their cytoplasmic regions, and their signal transductions are known to be mediated through associations with other tyrosine kinase proteins existing freely in the cytoplasm.

Though the sites on receptors binding with these cytoplasmic tyrosine kinases (JAK kinases) are conserved among family members, the homology is not very high (Murakami et al., Proc. Natl. Acad. Sci. USA, 88:11349-11353, 1991). Actually, the sequence that best characterizes these hemopoietin receptors exists in the extracellular region. In particular, a five amino acid motif, Trp-Ser-Xaa-Trp-Ser (SEQ ID NO:22), (wherein "Xaa" is an arbitrary amino acid), is conserved in almost all of the hemopoietin receptors. Therefore, novel receptors may be obtained by searching for novel family members using this sequence. In fact, these approaches have already led to the identification of the IL-11 receptor (Robb et al., J. Biol. Chem., 271:13754-13761, 1996), the leptin receptor (Gainsford et al., Proc. Natl. Acad. Sci. USA, 93:14564-8, 1996), and the IL-13 receptor (Hilton et al., Proc. Natl. Acad. Sci. USA, 93:497-501, 1996).

SUMMARY

The present invention provides novel hemopoietin receptor proteins, and DNA encoding these proteins. The present invention also provides a vector into which the DNA has been inserted, a transformant harboring the DNA, and a method for producing recombinant proteins using the transformant. The present invention also provides methods of screening for compounds that bind to the protein.

Initially, the inventors attempted to find a novel receptor using oligonucleotides encoding the Trp-Ser-Xaa-Trp-Ser (SEQ ID NO:22) motif (WS motif), as the probe by plaque hybridization, RT-PCR method, and so on. However, it was extremely difficult to strictly select only those to which all 15 nucleotides that encode the motif would completely hybridize under the usual hybridization conditions, because the oligonucleotide tggag(t/c)nnntggag(t/c) wherein "n" is an arbitrary nucleotide (SEQ ID NO:21) encoding the motif was short, having just 15 nucleotides, and had a high g/c content. Additionally, similar sequences are contained within cDNA encoding proteins other than hemopoietin receptors, starting with various collagens that are thought to be widely distributed and also have high expression amounts, which makes the screening by the above-mentioned plaque hybridization and RT-PCR extremely inefficient.

To solve these problems, the inventors searched for additional motifs, other than the site of the above-mentioned WS motif, that are conserved in the hemopoietin receptor family. As a result, a residue, either tyrosine or histidine, located 13 to 27 amino acids upstream of the WS motif in the extracellular domain was found to be highly conserved in the receptor family. Furthermore, additional search for consensus sequences that are frequently found in the 6 amino acids from the above Tyr/His toward the C-terminus led to the identification of the following consensus sequence: (Tyr/His)-Xaa-(Hydrophobic/Ala)-(Gln/Arg)-Hydrophobic-Arg (hereinafter, abbreviated as the YR motif). However, this YR motif is not exactly a perfect consensus sequence, and the combination of the nucleotide sequence that encodes the motif is very complicated. Therefore, it is practically impossible to synthesize and provide oligonucleotides that encode all of the amino acid sequences as probes for hybridization, which is a practical method for screening, or as primers aimed for RT-PCR.

Accordingly, the inventors looked for other approaches to practically search for novel members of the hemopoietin receptor family using the above two motifs as probes, and determined that it would be appropriate to perform a database search on the computer using partial amino acid sequences of known hemopoietin receptors, including both motifs as the query. The inventors repeated TBlastN searches on the gss and htgs database in GenBank, using partial amino acid sequences from multiple known hemopoietin receptors as the query. As a result, many false positive clones were obtained in all cases. However, by then comparing the amino acid sequence deduced from the nucleotide sequence proximal to the probe of the above clones with the sequence of known hemopoietin receptors, the inventors were able to select genes that encode members of the receptor family. From these results, the inventors identified a single clone containing a human genomic sequence which was suspected to encode a novel hemopoietin receptor and named it NR10.

The above nucleotide sequence was used to design specific oligonucleotide primers. The primers were used to perform 5'- and 3'-RACE using cDNA libraries from human fetal hepatocytes and human placenta as the template. As a result, a full-length cDNA, NR10.1, encoding a transmembrane receptor of 652 amino acids was isolated, and the whole nucleotide sequence was determined. At the same time, a cDNA clone, NR10.2, presumed to be a splice variant of NR10, was also successfully isolated from the 3'-RACE product. Based on the determined nucleotide sequence, NR10.2 was suggested to encode a soluble receptor-like protein of 252 amino acids. It was revealed that the cysteine residues, proline-rich motif, and WSXWS (SEQ ID NO:22) motif, in the extracellular domain that is conserved among the receptor family members, the box1 motif in the intracellular domain that is implicated in signal transduction, and so on were well conserved in the primary structure of NR10.1. Therefore, NR10.1 was considered to encode a typical hemopoietin receptor.

Subsequently, RT-PCR was performed using mRNA prepared from various human organs and primer sets specific to NR10.1 and NR10.2, respectively, to search for tissues expressing the respective genes and to examine their distribution and expression pattern in human tissues. The products of RT-PCR were subjected to Southern blotting using cDNA fragments specific to NR10.1 and NR10.2, respectively, in order to discard the possibility of non-specific amplification and to quantify the amount of the products. The results indicated that the NR10.2 gene is constitutively expressed in all tissues examined at a constant level. In contrast, the expression of NR10.1 was detected in restricted organs and tissues: in particular, strong expression was detected in adult heart, placenta, testis, thymus, and peripheral leukocytes, and weak expression was detected in spleen, bone marrow, prostate, ovary, pancreas, and lung.

The inventors also performed PCR cloning to isolate the full-length open reading frame (ORF) of NR10.1, and by chance, isolated another cDNA clone, dubbed NR10.3, containing a nucleotide sequence in which a single nucleotide is missing from the sequence of NR10.1 and encoding a transmembrane type receptor protein of 662 amino acids. NR10.3 was considered to possess similar functions as NR10.1 from the closely related structures.

Based on the above features, NR10 is presumed to be a novel hemopoietin receptor molecule related to the regulation of the immune system or hematopoiesis in vivo. The gene encoding NR10 will be extremely useful in screening for novel hematopoietic factors that can functionally bind to the receptor protein.

Consequently, this invention relates to novel hemopoietin receptors and genes encoding the receptors, as well as a method for producing and using the same. More specifically, the present invention provides the following:

(1) a DNA selected from the group consisting of:
  (a) a DNA encoding a protein consisting of the amino acid sequence of any of SEQ ID NOs:2, 4, and 17;
  (b) a DNA comprising the coding region of the nucleotide sequence of any of SEQ ID NOs:1, 3, and 16;
  (c) a DNA encoding a protein consisting of the amino acid sequence of any of SEQ ID NOs:2, 4, and 17, in which one or more amino acids are modified by deletion, addition and/or substitution by another amino acid, wherein said protein is functionally equivalent to the protein consisting of the amino acid sequence of any of SEQ ID NOs:2, 4, and 17; and
  (d) a DNA hybridizing under stringent conditions with a DNA consisting of the nucleotide sequence of any of SEQ ID NOs:1, 3, and 16, and encoding a protein that is functionally equivalent to the protein consisting of the amino acid sequence of any of SEQ ID NOs:2, 4, and 17;

(2) a DNA encoding a partial peptide of a protein consisting of the amino acid sequence of any of SEQ ID NOs:2, 4, and 17;

(3) a vector into which the DNA described in (1) or (2) is inserted;

(4) a transformant harboring the DNA described in (1) or (2) in an expressible manner;

(5) a protein or peptide that is encoded by the DNA described in (1) or (2);

(6) a method for producing the protein or peptide of (5), comprising the steps of: culturing the transformant of (4), and recovering the expressed protein from said transformant or the culture supernatant;

(7) a method of screening for a compound that binds to the protein of (5), comprising the steps of:
  (a) contacting a sample with the protein of (5) or partial peptide thereof;
  (b) detecting the binding activity of the sample with the protein of (5) or partial peptide thereof; and
  (c) selecting the compound that binds to the protein of (5) or partial peptide thereof;

(8) an antibody binding to the protein of (5);

(9) a method for detecting or measuring the protein of (5), comprising the steps of: exposing the antibody of (8) to a sample expected to contain the protein of (5), and detecting or measuring the production of the immune complex between said antibody and said protein; and

(10) a polynucleotide complementary to either a DNA that comprises the nucleotide sequence of any of SEQ ID NOs:1, 3, and 16 or its complementary strand, wherein the polynucleotide comprises at least 15 nucleotides.

This invention provides a novel hemopoietin receptor NR10. According to the result of the database search on GenBank, 5'- and 3'-RACE analysis, the inventors finally succeeded in the identification and isolation of a novel hemopoietin receptor gene NR10. It was found that at least two splice variants are transcribed from NR10. One of these variants, the cDNA clone NR10.1, encodes a transmembrane receptor protein, and the other, NR10.2, encodes a soluble receptor-like protein of 252 amino acids. Furthermore, the inventors performed PCR cloning in order to isolate the full length ORF of the NR10.1 cDNA, and by chance, succeeded in isolating another cDNA clone, named NR10.3, containing a full length ORF encoding a transmembrane type receptor protein of 662 amino acids.

The nucleotide sequence of the NR10.1 cDNA and the amino acid sequence of the protein encoded by the cDNA are shown in SEQ ID NOs:1 and 2, respectively. The nucleotide sequence of the NR10.2 cDNA and the amino acid sequence of the protein encoded by the cDNA are shown in SEQ ID NOs:3 and 4, respectively. The nucleotide sequence of the NR10.3 cDNA and the amino acid sequence of a protein encoded by the cDNA are shown in SEQ ID NOs:16 and 17, respectively.

The NR10.3 cDNA clone has a single nucleotide deletion in the adenine cluster, located proximally to the stop codon, as compared with the NR10.1 clone, which results in a frame shift from that position leading to a different open reading frame. Thus, the difference between the two clones is not caused because they are transcription products of splice variants. Except for the deletion of one nucleotide, NR10.1 and NR10.3 cDNA clones share an identical sequence. Meanwhile, their extracellular domains are encoded by a completely identical sequence and, thus, have an identical tertiary structure, and thereby, are considered to recognize the same specific ligand. Furthermore, their intracellular domains share the Box1 motif (Pro-Xaa-Pro sequence following several basic residues and multiple hydrophobic residues) located immediately after the transmembrane domain, and are presumed to bind to the JAK kinase. Therefore, it is predicted that the proteins encoded by the two clones are functionally equivalent.

RT-PCR analysis using mRNA from various human organs revealed that the NR10.2 gene is constitutively expressed in all examined tissues at a constant level. In contrast, expression of the NR10.1 gene was detected in restricted tissues and organs: in particular, strong expression in adult heart, placenta, testis, thymus, and peripheral leukocytes, and weak expression in spleen, bone marrow, prostate, ovary, pancreas, and lung. Thus, it was presumed that NR10.1 encodes a novel hematopoietic factor receptor.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2, 4 or 17. The invention also includes a polypeptide, or fragment thereof, that differs from the corresponding sequence shown as SEQ ID NO:2, 4 or 17. The differences are, preferably, differences or changes at a non-essential residue or a conservative substitution. In one embodiment, the polypeptide includes an amino acid sequence at least about 60% identical to a sequence shown as SEQ ID NO:2, 4 or 17, or a fragment thereof. Preferably, the polypeptide is at least 65%, 70%, 75%, 80%, 85%, 90%, 95%, 98%, 99% or more identical to SEQ ID NO:2, 4 or 17 and has at least one hemopoietin receptor function or activity described herein, e.g., the polypeptide binds to a hematopoietin factor. Preferred polypeptide fragments of the invention are at least 10%, preferably at least 20%, 30%, 40%, 50%, 60%, 70%, or more, of the length of the sequence shown as SEQ ID NO:2, 4 or 17 and have at least one hemopoietin receptor function or activity described herein. Or alternatively, the fragment can be merely an immunogenic fragment.

The above NR10 proteins may be useful for medical application. Since NR10.1 is expressed in thymus, peripheral leukocytes, and spleen, it could be a receptor for an unknown hematopoietic factor. Therefore, NR10 proteins are a useful tool in the identification of the unknown hematopoietic factor. They may also be used to screen a peptide library or synthetic chemical compounds in order to isolate or identify agonists or antagonists that can functionally bind to the NR10 molecule. Moreover, clinical application is expected of novel molecules binding to the NR10 molecule and specific antibodies that can limit the function of the NR10 molecule to regulate the immune response or hematopoiesis in vivo, by searching such molecules and antibodies.

NR10 is expected to be expressed in a restricted population of cells in the hematopoietic tissues, and thus, anti-NR10 antibodies are useful for the isolation of such cell populations. The isolated cell populations may be used in cell transplantation. Furthermore, it is expected that the anti-NR10 antibody may be used for the diagnosis or treatment of diseases, such as leukemia.

On the other hand, the soluble proteins comprising the extracellular domain of NR10 protein and the splice variant of NR10, NR10.2, may be used as a decoy-type receptor to inhibit the NR10 ligand. They may be useful for treatment of diseases in which NR10 is implicated, such as leukemia.

This invention includes proteins that are functionally equivalent to the NR10 protein. For instance, homologues of human NR10 protein in other species and mutants of human NR10 protein are included. Herein, the term "functionally equivalent" refers to proteins having an equivalent biological activity as compared to that of an NR10 protein. Such biological activity may include the protein activity as a membrane bound or soluble form hematopoietic factor receptor.

Methods of introducing mutations for preparing proteins that are functionally equivalent to another protein are well known to one skilled in the art. For example, one may use site-directed mutagenesis (Hashimoto-Goto et al., Gene, 152: 271-275, 1995; Zoller et al., Methods Enzymol., 100:468-500, 1983; Kramer et al., Nucl. Acids Res., 12:9441-9456, 1984; Kramer et al., Methods. Enzymol., 154:350-367, 1987; Kunkel, Proc. Natl. Acad. Sci. USA, 82:488-492, 1985; Kunkel, Methods Enzymol., 85:2763-2766, 1988) and such in order to introduce an appropriate mutation into the amino acid sequence of human NR10 protein and prepare a protein that is functionally equivalent to the protein. Mutations of amino acids may occur in nature as well. This invention includes proteins having the amino acid sequence of human NR10 protein in which one or more amino acid residues are mutated, and wherein the proteins are functionally equivalent to human NR10 protein.

As a protein functionally equivalent to the NR10 protein of the invention, the following can be specifically mentioned: one in which one or two or more, preferably, two to 30, more preferably, two to ten amino acids are deleted in any one of the amino acid sequences of SEQ ID NO:2, SEQ ID NO:4 or SEQ ID NO:17; one in which one or two or more, preferably, two to 30, more preferably, two to ten amino acids have been added into any one of the amino acid sequences of SEQ ID NO:2, SEQ ID NO:4 or SEQ ID NO:17; or one in which one or two or more, preferably, two to 30, more preferably, two to ten amino acids have been substituted with other amino acids in any one of the amino acid sequences of SEQ ID NO:2, SEQ ID NO:4 or SEQ ID NO:17.

As for the amino acid residue to be mutated, it is preferable that it be mutated into a different amino acid that allows the properties of the amino acid side-chain are conserved. Examples of properties of amino acid side chains are the following: hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base-containing side-chain (R, K, H); and an aromatic-containing side-chain (H, F, Y, W) (The parenthetic letters indicate the one-letter codes of amino acids).

It is known that a protein may have an amino acid sequence of which is modified by deletion, addition, and/or substitution by other amino acids of one or more amino acid residues, yet still retain its biological activity (Mark et al., Proc. Natl. Acad. Sci. USA, 81:5662-5666, 1984; Zoller et al., Nucl. Acids Res., 10:6487-6500, 1982; Wang et al., Science, 224:1431-1433; Dalbadie-McFarland et al., Proc. Natl. Acad. Sci. USA, 79:6409-6413, 1982).

A fusion protein containing human NR10 protein is an example of a protein in which one or more amino acid residues have been added to the amino acid sequence (SEQ ID NO:2, 4 or 17) of human NR10 protein. A fusion protein is made by fusing the human NR10 protein of the present invention with another peptide(s) or protein(s) and is included in the present invention. A fusion protein can be prepared by ligating a DNA encoding the human NR10 protein of the present invention with a DNA encoding another peptide(s) or protein(s) in frame, introducing the ligated DNA into an expression vector, and expressing the fusion gene in a host. Methods known by one skilled in the art can be used for preparing such a fusion gene. There is no restriction as to the other peptide(s) or protein(s) that is (are) fused to the protein of this invention.

Other peptide(s) to be fused with a protein of the present invention are known peptides, for example, FLAG (Hopp et al., Biotechnology, 6:1204-1210, 1988), 6×His constituting six histidine (His) residues, 10×His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and so on. Other examples of peptides to be fused with the protein of the present invention are the glutathione-S-transferase (GST), Influenza agglutinin (HA), immunoglobulin constant region, β-galactosidase, maltose-binding protein (MBP), etc.

Fusion proteins can be prepared by fusing commercially available DNA encoding these peptides or proteins with DNA encoding a protein of the present invention and expressing the fused DNA prepared.

The hybridization technique (Sambrook et al., Molecular Cloning 2nd ed. 9.47-9.58, Cold Spring Harbor Lab. press, 1989) is well known to one skilled in the art as an alternative method for preparing a protein functionally equivalent to a certain protein. More specifically, one skilled in the art can utilize the general procedure to obtain a protein functionally equivalent to a human NR10 protein by isolating DNA having a high homology with the whole or part of the DNA (SEQ ID NO:1, 3 or 16) encoding the human NR10 protein. Thus, the present invention includes such proteins, that are encoded by DNAs that hybridize with a DNA consisting of a DNA encoding human NR10 protein or part thereof and that are functionally equivalent to a human NR10 protein. For instance, homologues of human NR10 in other mammals (such as those of monkey, mouse, rabbit, and bovine) are included. In order to isolate a cDNA with high homology to a DNA encoding a human NR10 protein from animals, it is preferable to use tissues such as heart, placenta, and testis.

Stringent hybridization conditions for isolating DNA encoding functionally equivalent proteins of human NR10 protein can be suitably selected by one skilled in the art, and for example, low-stringent conditions can be given. Low-stringent conditions are, for example, 42° C., 2×SSC, and 0.1% SDS, and preferably, 50° C., 2×SSC, and 0.1% SDS. Highly stringent conditions are more preferable and include, for example, 65° C., 2×SSC, and 0.1% SDS. Under these conditions, the higher the temperature, the higher the homology of the obtained DNA will be. However, several factors other than temperature, such as salt concentration, can influence the stringency of hybridization and one skilled in the art can suitably select the factors to accomplish a similar stringency.

In place of hybridization, the gene amplification method, for example, the polymerase chain reaction (PCR) method can be utilized to isolate the object DNA using primers synthesized based on the sequence information of the DNA encoding the human NR10 protein (SEQ ID NO:1, 3 and 16).

Proteins that are functionally equivalent to human NR10 protein, encoded by DNA isolated through the above hybridization technique or by the gene amplification technique, normally have a high homology to the amino acid sequence of the human NR10 protein. The proteins of the present invention also include proteins that are functionally equivalent to the human NR10 protein, which also have a high homology with the protein comprising any one of the amino acid sequences of SEQ ID NO:2, 4, or 17. High homology is defined normally as a homology of 70% or higher, favorably 80% or higher, more favorably 90% or higher, and most favorably 95% or higher. The homology of a protein can be determined by the algorithm in "Wilbur, W. J. and Lipman, D. J. Proc. Natl. Acad. Sci. USA 80: 726-730 (1983)."

The amino acid sequence, molecular weight, isoelectric point, the presence or absence of the sugar chain, and the form of a protein of the present invention may differ according to the producing cells, host, or purification method described below. However, so long as the obtained protein has an equivalent function to a protein of the present invention (SEQ ID NO:2, 4 and 17), it is included in the present invention. For example, if a protein of the present invention is expressed in prokaryotic cells, such as *E. coli*, a methionine residue is added at the N-terminus of the amino acid sequence of the expressed protein. If a protein of the present invention is expressed in eukaryotic cells, such as mammalian cells, the N-terminal signal sequence is removed. Such proteins are also included in the proteins of the present invention.

For example, as the result of analysis of the protein of the invention based on the method in "Von Heijne, G., Nucl. Acids Res., 14: 4683-4690 (1986)", it was presumed that the signal sequence is from the 1st Met to the 32nd Ala in the amino acid sequence of SEQ ID NO:2, 4 and 17. Therefore, the present invention encompasses a protein comprising the sequence from the 33rd Ala to 652nd Asp in the amino acid sequence of SEQ ID NO:2. Similarly, the present invention encompasses a protein comprising the sequence from the 33rd Ala to 252nd Val in the amino acid sequence of SEQ ID NO:4. Similarly, the present invention encompasses a protein comprising the sequence from the 33rd Ala to 662nd Ile in the amino acid sequence of SEQ ID NO:17.

A protein of the present invention can be prepared by methods known to one skilled in the art, as a recombinant protein, and also as a natural protein. A recombinant protein can be prepared by inserting a DNA encoding a protein of the present invention (for example, the DNA comprising the nucleotide sequence of SEQ ID NO:1, 3 or 16) into a suitable expression vector, introducing the vector into a suitable host cell, and collecting the protein from the resulting transformant. After obtaining the extract, recombinant protein can be purified and prepared by subjecting to chromatography, such as ion exchange chromatography, reverse phase chromatography, gel filtration, and such, or affinity chromatography, to which antibodies against the protein of the invention are immobilized, or combining one or more of these columns.

Further, when a protein of the present invention is expressed within host cells (for example, animal cells and *E. coli*), as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin, factor-Xa, and such, as required.

A natural protein may be isolated by methods known to one skilled in the art. For instance, extracts of tissue or cells expressing a protein of the invention may be reacted with an affinity column described below, to which antibodies binding to the NR10 protein are attached, to isolate the natural protein. Polyclonal or monoclonal antibodies may be used.

This invention also includes partial peptides of the proteins of the invention. The peptide consisting of the amino acid sequence specific to a protein of the invention are composed of at least 7 amino acids, favorably more than 8 amino acids, and more favorably more than 9 amino acids. The partial peptides may be useful for preparing antibodies against a protein of the invention, or screening compounds binding to a protein of the present invention, or screening activators or inhibitors of a protein of the present invention. Alternatively, it may be used as an antagonist for the ligand of a protein of the invention. A partial peptide of the present invention is, for example, a partial peptide having the active center of the protein consisting of any one of the amino acid sequences of SEQ ID NO:2, 4, or 17. Additionally, the partial peptides may contain one or more regions of the hydrophilic regions or hydrophobic regions presumed by hydrophobicity plot analysis. These partial peptides may contain the whole or a part of a hydrophilic region, or may contain the whole or a part of a hydrophobic region. Moreover, for example, soluble proteins and proteins comprising extracellular regions of a protein of the invention are also encompassed in the present invention.

The partial peptides of the invention may be produced by genetic engineering techniques, well-known peptide synthesizing methods, or by excising a protein of the invention with a suitable peptidase. The solid-phase synthesizing method and the liquid-phase synthesizing method may be used as peptide synthesizing methods.

Another objective of this invention is to provide DNA encoding a protein of the invention. The DNA may be useful for producing the above proteins of the invention in vivo and in vitro. Furthermore, for example, it is also possible to use the DNA for application to gene therapy and such of diseases arising from abnormalities of the gene encoding the protein of the present invention. The DNA may be provided in any form as long as it encodes a protein of the invention. Thus, the DNA may be a cDNA synthesized from mRNA, genomic DNA, or chemically synthesized DNA. Furthermore, a DNA comprising any nucleotide sequence based on the degeneracy of genetic code may be included as long as it encodes a protein of the present invention.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1, 3 or 16. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1, 3 or 16. In the case of an isolated nucleic acid molecule which is longer than or equivalent in length to the reference sequence, e.g., SEQ ID NO:1, 3 or 16, the comparison is made with the full length of the reference sequence. Where the isolated nucleic acid molecule is shorter that the reference sequence, e.g., shorter than SEQ ID NO:1, 3 or 16, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (Proc. Natl. Acad. Sci. USA, 87:2264-2268, 1990), modified as in Karlin and Altschul, Proc. Natl. Acad. Sci. USA, 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al (Nucl. Acids Res., 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

The DNA of the invention can be prepared by any method known to one skilled in the art. For instance, the DNA may be prepared by constructing a cDNA library from cells expressing the protein, and performing hybridization using a partial sequence of the DNA of the invention (SEQ ID NO:1 or 3, for instance) as a probe. A cDNA library may be constructed according to the method described in the literature (Sambrook et al., Molecular Cloning, Cold Spring Harbor Laboratory Press, 1989), or a commercial DNA library may be used. Alternatively, the DNA may be prepared by obtaining RNA from a cell expressing a protein of the present invention, synthesizing oligo DNA based on the sequence of the present DNA (SEQ ID NO:1, 3 or 16, for instance), performing PCR using the synthesized DNA as the primer, and amplifying the cDNA encoding a protein of the present invention.

By determining the nucleotide sequence of the obtained cDNA, the translation region encoded by the cDNA can be determined, and the amino acid sequence of the protein of the present invention can be obtained. Furthermore, genomic DNA can be isolated by screening genomic DNA libraries using the obtained cDNA as a probe.

Specifically, this can be done as follows: First, mRNA is isolated from cells, tissues, and organs (for example, ovary, testis, placenta, etc.) expressing a protein of the invention. To isolate the mRNA, at first, whole RNA is prepared using well-known methods, for example, guanidine ultracentrifugation method (Chirgwin et al., Biochemistry, 18:5294-5299, 1979); the AGPC method (Chomczynski et al., Anal. Biochem., 162:156-159, 1987), and such, and mRNA from whole mRNA is purified using the mRNA Purification Kit (Pharmacia), etc. Alternatively, mRNA may be directly prepared using the QuickPrep mRNA Purification Kit (Pharmacia).

cDNA is synthesized using reverse transcriptase from the obtained mRNA. cDNA can be synthesized by using the AMV Reverse Transcriptase First-strand cDNA Synthesis Kit (SEIKAGAKU CORPORATION), etc. Additionally, cDNA synthesis and amplification may be also done by using the primer and such described herein following the 5'-RACE method (Frohman et al., Proc. Natl. Acad. Sci. USA, 85:8998-9002, 1988; Belyaysky et al., Nucl. Acids Res., 17:2919-2932, 1989) utilizing the polymerase chain reaction (PCR) and the 5'-Ampli FINDER RACE KIT (Clontech).

The objective DNA fragment is prepared from the obtained PCR product and ligated with the vector DNA. Thus, a recombination vector is created, introduced into E. coli, and such, and colonies are selected to prepare the desired recombination vector. The nucleotide sequence of the objective DNA can be verified by known methods, for example, the dideoxy nucleotide chain termination method.

With regards to the DNA of the invention, a sequence with higher expression efficiency can be designed by considering the codon usage frequency in the host used for the expression (Grantham et al., Nucl. Acids Res., 9:43-74, 1981). The DNA of the invention may also be modified using commercially available kits and known methods. Modifications are given as, for example, digestion by restriction enzymes, insertion of synthetic oligonucleotides and suitable DNA fragments, addition of linkers, insertion of a start codon (ATG) and/or stop codon (TAA, TGA, or TAG), and such.

Specifically, the DNA of the invention includes DNA consisting of the nucleotide sequence from the 523rd "A" to 2478th "C" of SEQ ID NO:1, 523rd "A" to 1278th "G" of SEQ ID NO:3, or 11th "A" to 1996th "A" of SEQ ID NO:16.

The DNA of the present invention includes DNA that hybridize under stringent conditions to the DNA consisting of any one of the nucleotides, wherein the DNA encodes a protein functionally equivalent to an above-mentioned protein of the present invention.

Stringent conditions can be suitably selected by one skilled in the art, and for example, low-stringent conditions can be given. Low-stringent conditions are, for example, 42° C., 2×SSC, and 0.1% SDS, and preferably 50° C., 2×SSC, and 0.1% SDS. More preferable are highly stringent conditions which are, for example, 65° C., 2×SSC, and 0.1% SDS. Under these conditions, the higher the temperature, the higher the homology of the obtained DNA will be. The above DNA hybridizing to the DNA with the sequences of SEQ ID NO:1, 3, and 16, is preferably a natural DNA such as cDNA and chromosomal DNA.

Moreover, the present invention provides a vector containing a DNA of the invention as an insert. The vector may be useful for maintaining the DNA in host cells or producing the protein of the invention.

If the host cell is E. coli (such as JM109, DH5α, HB101, and XL1Blue), any vector may be used as long as it contains the "ori" for amplification in E. coli that enables large-scale preparation, and a selection marker for transformants (for instance, a drug resistance gene that enables selection by a drug such as ampicillin, tetracycline, kanamycin, and chloramphenicol). For instance, series of the M13 vectors and pUC vectors, pBR322, pBluescript, pCR-Script, and so on may be used. For the purpose of subcloning or excision of a cDNA, pGEM-T, pDIRECT, pT7, and such may be used as well. For producing the protein of the invention, an expression vector is especially useful. For instance, if the protein is to be expressed in E. coli, the expression vector must have such characteristics as above to be amplified in E. coli, and a promoter for efficient expression, such as the lacZ promoter (Ward et al., Nature, 341:544-546, 1989; FASEB J., 6:2422-2427, 1992), araB promoter (Better et al., Science, 240:1041-1043, 1988), or T7 promoter. Such vector includes pGEX-5X-1 (Pharmacia), vectors in the QIAexpress system (QIAGEN), pEGFP, pET (BL21 expressing the T7 RNA polymerase is favorably used as the host), and so on except those mentioned above.

The vector may contain a signal sequence for polypeptide secretion. The pelB signal sequence (Lei et al., J. Bacteriol., 169:4379, 1987) may be used to produce the proteins in the periplasm of E. coli. Vectors may be introduced into host cells, for example, by the calcium chloride method or electroporation.

For example, the expression vector to prepare the protein of the invention may be a mammal-derived expression vector (e.g., pcDNA3 (Invitrogen), pEGF-BOS (Nucl. Acids. Res., 18:5322, 1990), pEF and pCDM8), an insect cell-derived expression vector (e.g., "Bac-to-BAC baculovirus expression system" (GIBCO BRL), pBacPAK8), a plant-derived expression vector (e.g., pMH1 and pMH2), an animal virus-derived expression vector (e.g., pHSV, pMV, and pAdexLcw), a retrovirus-derived expression vector (e.g., pZIpneo), an yeast-derived expression vector (e.g., "Pichia Expression Kit" (In vitrogen), pNV11 and SP-Q01), or a Bacillus subtilis-derived expression vector (e.g., pPL608 and pKTH50), other than E. coli.

For the expression in animal cells, such as CHO, COS, and NIH3T3 cells, the expression vector must have a promoter such as SV40 promoter (Mulligan et al., Nature, 277:108, 1979), MMLV-LTR promoter, EF1α promoter (Mizushima et al., Nucl. Acids Res., 18:5322, 1990), and CMV promoter. More favorably, the vector may contain a marker for the selection of transfected cells (for instance, a drug resistance gene for selection by a drug such as neomycin and G418). Such vectors include pMAM, pDR2, pBK-RSV, pBK-CMV, pOPRSV, pOP13, and so on.

Furthermore, in order to achieve stable gene expression and amplification of the copy number of genes in cell, CHO cells deficient in the metabolic pathway for nucleotide synthesis may be used. The CHO cell is transfected with an expression vector containing the DHFR gene that complements the deficiency (such as pCHOI), then the vector may be amplified by methotrexate (MTX) treatment. For transient gene expression, COS cells containing a gene expressing the SV40 T-antigen on its chromosome may be used to transform with a vector containing the SV40 replication origin (such as pCD). Examples of replication origins to be used in the present invention include those derived from polyomavirus, adenovirus, bovine papilomavirus (BPV), and such. Moreover, to amplify the gene copies in host cell lines, the expression vector may include an aminoglycoside transferase (APH) gene, thymidine kinase (TK) gene, E. coli xanthine guanine phosphoribosyl transferase (Ecogpt) gene, dihydrofolate reductase (dhfr) gene, and such as a selective marker.

In vivo expression of the DNA of the invention may be performed by constructing the DNA into an appropriate vector and transfecting the construct into the body using retrovirus, liposome, cationic liposome, adenovirus, and so on. It is possible to use such a construct to perform gene therapy for diseases that arise from mutations in the NR10 gene. Examples of vectors used for this purpose include an adenovirus vector (such as pAdexlcw) and a retrovirus vector (such as pZIPneo), but are not limited thereto. General manipulations, such as insertion of the DNA into the vector, may be performed by using standard methods (Molecular Cloning, 5.61-5.63). The vector may be administered to the patient through ex vivo or in vivo methods.

Another object of this invention is to provide a transformant that contains the DNA of the invention in a expressible manner. The host cell to insert the vector of the present invention is not limited in any way, and $E.$ $coli$, a variety of animal cells, and so on may be used. The transformant may be used as a producing system for preparing or expressing a protein of the invention. In vitro and in vivo production systems are known as production systems for producing proteins. Production systems using eukaryotic cells and prokaryotic cells may be used as the in vitro production systems.

When using eukaryotic cells, production systems using, for example, animal cells, plant cells, and fungal cells are available as hosts. Examples animal cells used include mammalian cells such as CHO (J. Exp. Med., 108:945, 1995), COS, 3T3, myeloma, baby hamster kidney (BHK), HeLa, Vero, amphibian cells such as $Xenopus$ $oocytes$ (Valle et al., Nature, 291: 338-340, 1981), insect cells such as sf9, sf21, or Tn5. As CHO cells, especially DHFR gene-deficient CHO cell, dhfr-CHO (Proc. Natl. Acad. Sci. USA, 77:4216-4220, 1980), and CHO K-1 (Proc. Natl. Acad. Sci. USA, 60:1275, 1968) can be suitably used. For large-scale preparation in animal cells, CHO cells may be favorably used. The vector may be transfected into host cells using a variety of methods, such as those using calcium phosphate, DEAE-dextran, or cationic liposome DOTAP (Boeringer Mannheim), as well as electroporation, lipofection, and so on.

$Nicotiana$ $tabacum$-derived cells are well known as protein production systems in plant cells, and these can be callus cultured. As fungal cells, yeasts such as the $Saccharomyces$ genus, for example, $Saccharomyces$ $cerevisiae$; filamentous bacteria, such as $Aspergillus$ genus, for example, $Aspergillus$ $niger$ are known.

Bacterial cells may be used as prokaryotic production systems. As bacterial cells, $E.$ $coli$, for example, JM109, DH5α, HB101, and such, as well as others like $Bacillus$ $subtilis$ are known.

Proteins can be obtained by transforming these cells with the objective DNA, and culturing the transformed cells in vitro according to known methods. For example, DMEM, MEM, RPMI1640, and IMDM can be used as culture media of animal cells. Occasionally, fetal calf serum (FCS) and such serum supplements may be added in the above media; alternatively, a serum-free culture medium may be used. The pH is preferably from about 6 to 8. The culturing is usually performed at about 30° C. to 40° C., for about 15 to 200 hr, and medium changes, aeration, and stirring is done as necessary.

On the other hand, for example, production systems using animals and plants may be given as in vivo protein production systems. The objective DNA is introduced into the plant or animal, and the protein is produced within the plant or animal, and then, the protein is recovered. The term "host" as used in the present invention encompasses such animals and plants as well.

When using animals, mammalian and insect production systems can be used. As mammals, goats, pigs, sheep, mice, and bovine may be used (Vicki Glaser, SPECTRUM Biotechnology Applications (1993)). Transgenic animals may also be used when using mammals.

For example, the objective DNA is prepared as a fusion gene with a gene encoding a protein intrinsically produced into milk, such as goat β casein. Next, the DNA fragment containing the fusion gene is injected into goat's embryo, and this embryo is implanted in female goat. The objective protein can be collected from the milk of the transgenic goats produced from the goat that received the embryo, and descendants thereof. To increase the amount of protein-containing milk produced from the transgenic goat, a suitable hormone/hormones may be given to the transgenic goats (Ebert et al., Bio/Technology, 12:699-702, 1994).

Silk worms may be used as insects. When using silk worms, they are infected with baculoviruses to which the DNA encoding objective protein has been inserted, and the desired protein can be obtained from the body fluids of the silk worm (Susumu et al., Nature, 315:592-594, 1985).

When using plants, for example, tobacco can be used. In the case of tobacco, the DNA encoding the objective protein is inserted into a plant expression vector, for example, pMON 530, and this vector is introduced into a bacterium such as $Agrobacterium$ $tumefaciens$. This bacterium is infected to tobacco, for example, $Nicotiana$ $tabacum$, and it is able to obtain the desired polypeptide from the tobacco leaves (Julian et al., Eur. J. Immunol., 24:131-138, 1994).

Thus-obtained protein of the invention is isolated from inside or outside (medium, etc.) the host cell, and may be purified as a substantially pure homogenous protein. The separation and purification of the protein can be done using conventional separation and purification methods used to purify proteins and are not limited to any specific method. For example, chromatography column, filtration, ultrafiltration, salting out, solvent precipitation, solvent extraction, distillation, immunoprecipitation, SDS-polyacrylamide gel electrophoresis, isoelectric focusing, dialysis, recrystallization, and such may be suitably selected, or combined to separate/purify the protein.

For example, affinity chromatography, ion exchange chromatography, hydrophobic chromatography, gel filtration, reversed-phase chromatography, adsorption chromatography, and such can be exemplified as chromatographies (Strategies for Protein Purification and Characterization: A Laboratory Course Manual. Ed Daniel R. Marshak et al., Cold Spring Harbor Laboratory Press, 1996). These chromatographies can be performed by liquid chromatography, such as HPLC, FPLC, and the like. The present invention encompasses proteins highly purified by using such purification methods.

Proteins can be arbitrarily modified, or peptides may be partially excised by treating the proteins with appropriate modification enzymes prior to or after the purification. Trypsin, chymotrypsin, lysyl endopeptidase, protein kinase, glucosidase, and such are used as protein modification enzymes.

The present invention also provides antibodies binding to the protein of the invention. There is no particular restriction as to the form of the antibody of the present invention and the present invention includes polyclonal antibodies, as well as monoclonal antibodies. The antiserum obtained by immunizing animals such as rabbits with a protein of the present invention, as well polyclonal and monoclonal antibodies of all classes, human antibodies, and humanized antibodies made by genetic engineering, are also included.

A protein of the invention that is used as a sensitizing antigen for obtaining antibodies is not restricted by the animal species from which it is derived, but is preferably a protein derived from mammals, for example, humans, mice, or rats, especially preferably from humans. Proteins of human origin can be obtained by using the nucleotide sequence or amino acid sequence disclosed herein.

Herein, an intact protein or its partial peptide may be used as the antigen for immunization. As partial peptides of the proteins, for example, the amino (N) terminal fragment of the protein, and the carboxy (C) terminal fragment can be given. "Antibody" as used herein means an antibody that specifically reacts with the full-length or fragments of the protein.

A gene encoding a protein of the invention or a fragment thereof is inserted into a well-known expression vector, and by transforming the host cells with the vector described herein, the objective protein or a fragment thereof is obtained from inside or outside the host cell using well-known methods, and this protein can be used as the sensitizing antigen. Also, cells expressing the protein, cell lysates, or chemically synthesized protein of the invention may be also used as a sensitizing antigen.

The mammals that are immunized by the sensitizing antigen are not restricted, but it is preferable to select animals by considering the adaptability with the parent cells used in cell fusion. Generally, animals belonging to the rodentia, lagomorpha, and Primate family are used.

Examples of animals belonging to rodentia that may be used include mice, rats, hamsters, and such. Examples of animals belonging to lagomorpha that may be used include, for example, rabbits. Examples of Primates that may be used include monkeys. Examples of monkeys to be used include the infraorder catarrhini (Old World Monkeys), for example, cynomolgus monkeys, rhesus monkeys, sacred baboons, chimpanzees, and such.

Well-known methods may be used to immunize animals with the sensitizing antigen. For example, the sensitizing antigen is generally injected intraperitoneally or subcutaneously into mammals. Specifically, the sensitizing antigen is suitably diluted and suspended in physiological saline or phosphate-buffered saline (PBS) and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing an animal with the sensitizing antigen. After the immunization, the elevation in the level of serum antibody is detected by usual methods.

Polyclonal antibodies against a protein of the invention can be obtained as follows. After verifying that a desired serum antibody level has been reached, blood is withdrawn from the mammal sensitized with the antigen. Serum is isolated from this blood using well-known methods. The serum containing the polyclonal antibody may be used as the polyclonal antibody, or according to needs, the polyclonal antibody-containing fraction may be further isolated from the serum. For instance, a fraction of antibodies that specifically recognize the protein of the invention may be prepared by using an affinity column to which the protein is coupled. Then, the fraction may be further purified by using a Protein A or Protein G column in order to prepare immunoglobulin G or immunoglobulin M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method of Milstein et al. (Methods Enzymol., 73:3-46, 1981).

The hybridoma obtained from cell fusion is selected by culturing the cells in a standard selective culture medium, for example, HAT culture medium (hypoxanthine, aminopterin, thymidine-containing culture medium). The culture in this HAT medium is continued for a period sufficient enough for cells (non-fusion cells) other than the objective hybridoma to perish, usually from a few days to a few weeks. Next, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro, fusing the sensitized lymphocytes with myeloma cells derived from human, for example U266, having a permanent cell division ability (Unexamined Published Japanese Patent Application (JP-A) No. Sho 63-17688).

The obtained monoclonal antibodies can be purified by, for example, ammonium sulfate precipitation, protein A or protein G column, DEAE ion exchange chromatography, an affinity column to which the protein of the present invention is coupled, and so on. The antibody may be useful for the purification or detection of a protein of the invention. It may also be a candidate for an agonist or antagonist of the protein. Furthermore, it is possible to use it for the antibody treatment of diseases in which the protein is implicated. For in vivo administration (in such antibody treatment), human antibodies or humanized antibodies may be favorably used because of their reduced antigenicity.

For example, a human antibody against a protein can be obtained using hybridomas made by fusing myeloma cells with antibody-producing cells obtained by immunizing a transgenic animal comprising a repertoire of human antibody genes with an antigen such as a protein, protein-expressing cells, or a cell lysate thereof (WO92/03918, WO93/2227, WO94/02602, WO94/25585, WO96/33735, and WO96/34096).

Other than producing antibodies by using hybridoma, antibody-producing immunocytes, such as sensitized lymphocytes that are immortalized by oncogenes, may also be used.

Such monoclonal antibodies can also be obtained as recombinant antibodies produced by using the genetic engineering technique (for example, Borrebaeck, C. A. K. and Larrick, J. W., "Therapeutic Monoclonal Antibodies", Published in the United Kingdom by MacMillan Publishers Ltd., 1990). Recombinant antibodies are produced by cloning the encoding DNA from immunocytes, such as hybridoma or antibody-producing sensitized lymphocytes, incorporating this into a suitable vector, and introducing this vector into a host to produce the antibody. The present invention encompasses such recombinant antibodies as well.

Moreover, the antibody of the present invention may be an antibody fragment or a modified-antibody, so long as it binds to a protein of the invention. For example, Fab, F(ab')$_2$, Fv, or single chain Fv in which the H chain Fv and the L chain Fv are suitably linked by a linker (scFv, Huston et al., Proc. Natl. Acad. Sci. USA, 85:5879-5883, 1988) can be given as antibody fragments. Specifically, antibody fragments are produced by treating antibodies with enzymes, for example, papain, pepsin, and such, or by constructing a gene encoding an antibody fragment, introducing this into an expression vector, and expressing this vector in suitable host cells (for example, Co et al., J. Immunol., 152:2968-2976, 1994; Better et al., Methods Enzymol., 178:476-496, 1989; Pluckthun et al., Methods Enzymol., 178:497-515, 1989; Lamoyi, Methods Enzymol., 121:652-663, 1986; Rousseaux et al., Methods Enzymol., 121:663-669, 1986; Bird et al., Trends Biotechnol., 9:132-137, 1991).

As modified antibodies, antibodies bound to various molecules such as polyethylene glycol (PEG) can be used. The antibody of the present invention encompasses such modified antibodies as well. To obtain such a modified antibody, chemical modifications are done to the obtained antibody. These methods are already established in the field.

The antibody of the invention may be obtained as a chimeric antibody, comprising non-human antibody-derived variable region and human antibody-derived constant region, or as a humanized antibody comprising non-human antibody-derived complementarity determining region (CDR), human antibody-derived framework region (FR), and human antibody-derived constant region by using conventional methods.

Antibodies thus obtained can be purified to uniformity. The separation and purification methods used in the present invention for separating and purifying the antibody may be any method usually used for proteins. For instance, column chromatography, such as affinity chromatography, filter, ultrafiltration, salt precipitation, dialysis, SDS-polyacrylamide gel electrophoresis, isoelectric point electrophoresis, and so on, may be appropriately selected and combined to isolate and purify the antibodies (Antibodies: a laboratory manual. Ed Harlow and David Lane, Cold Spring Harbor Laboratory, 1988), but is not limited thereto. Antibody concentration of the above mentioned antibody can be assayed by measuring the absorbance, or by the enzyme-linked immunosorbent assay (ELISA), etc.

Protein A or Protein G column can be used for the affinity chromatography. Protein A column may be, for example, Hyper D, POROS, Sepharose F. F. (Pharmacia), and so on.

Other chromatography may also be used, such as ion exchange chromatography, hydrophobic chromatography, gel filtration, reverse phase chromatography, and adsorption chromatography (Strategies for Protein Purification and Characterization: A laboratory Course Manual. Ed. by Marshak D. R. et al., Cold Spring Harbor Laboratory Press, 1996). These may be performed on liquid chromatography such as HPLC or FPLC.

Examples of methods that assay the antigen-binding activity of the antibodies of the invention include, for example, measurement of absorbance, enzyme-linked immunosorbent assay (ELISA), enzyme immunoassay (EIA), radio immunoassay (RIA), or fluorescent antibody method. For example, when using ELISA, a protein of the invention is added to a plate coated with the antibodies of the invention, and next, the objective antibody sample, for example, culture supernatants of antibody-producing cells, or purified antibodies are added. Then, secondary antibody recognizing the antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (Pharmacia) may be used.

By using these methods, the antibody of the invention and a sample presumed to contain a protein of the invention are contacted, and the protein of the invention is detected or assayed by detecting or assaying the immune complex of the above-mentioned antibody and protein.

A method of detecting or assaying a protein of the invention is useful in various experiments using proteins as it can specifically detect or assay the proteins.

Another object of this invention is to provide a polynucleotide of at least 15 nucleotides that is complimentary to the DNA encoding human NR10 protein (SEQ ID NO:1, 3, or 16) or its complimentary strand.

Herein, the term "complimentary strand" is defined as one strand of a double strand DNA composed of A:T and G:C base pairs to the other strand. Also, "complimentary" is defined as not only those completely matching within a continuous region of at least 15 nucleotides, but also having a homology of at least 70%, favorably 80% or higher, more favorably 90% or higher, and most favorably 95% or higher within that region. The homology may be determined using the algorithm described herein.

Probes or primers for detection or amplification of the DNA encoding a protein of the invention, or a nucleotide or nucleotide derivative for the suppression of the protein expression (such as antisense oligonucleotide and ribozyme) are included in these polynucleotides. Such polynucleotides may be also used for preparing DNA chips.

The antisense oligonucleotide that hybridizes with a portion of the nucleotide sequence of any of SEQ ID NO:1, 3, and 16 is also included in the antisense oligonucleotides of the present invention. This antisense oligonucleotide is preferably one against at least 15 continuous nucleotides in any one of the nucleotide sequences of SEQ ID NO:1, 3 and 16. More preferably, it is the antisense oligonucleotide against at least 15 continuous nucleotides containing a translation start codon.

Derivatives or modified products of antisense oligonucleotides can be used as antisense oligonucleotides. Examples of such modified products include, for example, lower alkyl phosphonate modifications such as methyl-phosphonate-type or ethyl-phosphonate-type; phosphorothioate; phosphoroamidate-modified products, and such.

The term "antisense oligonucleotide(s)" as used herein means, not only those in which the nucleotides corresponding to those constituting a specified region of a DNA or mRNA are entirely complementary, but also those having a mismatch of one or more nucleotides, so long as the DNA or mRNA and the oligonucleotide can selectively and stably hybridize with the nucleotide sequence of SEQ ID NO:1, 3 or 16.

The antisense oligonucleotide derivative of the present invention acts upon cells producing a protein of the invention by binding to the DNA or mRNA encoding the protein to inhibit its transcription or translation, and to promote the degradation of mRNA, and has an effect of suppressing the function of the protein of the invention by suppressing the expression of the protein.

The antisense oligonucleotide derivative of the present invention can be made into an external preparation such as a liniment and a poultice by mixing with a suitable base material, which is inactive against the derivatives.

Also, as needed, the derivatives can be formulated into tablets, powders, granules, capsules, liposome capsules, injections, solutions, nose-drops, and freeze-dried agents by adding excipients, isotonic agents, solubilizers, stabilizers, preservatives, pain-killers, etc. These can be prepared using conventional methods.

The antisense oligonucleotide derivative is given to the patient by directly applying onto the ailing site, by injecting into the blood vessel and such, so that it will reach the ailing site. An antisense-mounting material can also be used to increase durability and membrane-permeability. Examples are, liposome, poly-L lysine, lipid, cholesterol, lipofectin, or derivatives of them.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide derivative of the present invention is useful in inhibiting the expression of the protein of the invention, and therefore is useful in suppressing the biological activity of the protein of the invention. Also, expression-inhibitors comprising the antisense oligonucleotide derivative of the present invention are useful, because of their capability to suppress the biological activity of the protein of the invention.

Proteins of this invention are useful for screening compounds binding to the protein. That is, the proteins are used in the method of screening for compounds that bind to the proteins of this invention, in which the method comprises bringing proteins of this invention into contact with a test sample that is expected to contain a compound to bind to the proteins and selecting a compound with the activity to bind to the proteins of this invention.

Proteins of this invention used in the screening may be any of recombinant, natural or partial peptides. Also they may be a purified protein, partial peptides thereof, or in the form of proteins expressed on the cell surface or membrane fractions. Samples to be tested are not limited, but may be cell extracts, culture supernatants, fermented products of microorganisms, extracts of marine organisms, plant extracts, purified or partially purified proteins, peptides, non-peptide compounds, synthetic low molecular compounds, or natural compounds. The protein of the invention may be exposed to the sample as a purified protein or soluble protein, in a form bound to a support, as a fusion protein with another protein, in a form expressed on the surface of cell membrane, or as membrane fractions.

A protein of the invention may be used to screen for proteins that bind to the protein (such as ligands) using a variety of methods known to one skilled in the art. These screening can be carried out, for example, by the immunoprecipitation method. Specifically, the method can be carried out as follows. The gene encoding the protein of this invention is expressed by inserting the gene into a vector for foreign gene expression like pSV2neo, pcDNA I, pCD8, and such, and expressing the gene in animal cells, etc. Any generally used promoters may be employed for the expression, including the SV40 early promoter (Rigby In Williamson (ed.), Genetic Engineering, Vol. 3. Academic Press, London, p. 83-141, 1982), EF-1α promoter (Kim et al., Gene, 91:217-223, 1990), CAG promoter (Niwa et al., Gene, 108:193-200, 1991), RSV LTR promoter (Cullen, Methods in Enzymology, 152:684-704, 1987), SR α promoter (Takebe et al., Mol. Cell. Biol., 8:466, 1988), CMV immediate early promoter (Seed et al., Proc. Natl. Acad. Sci. USA, 84:3365-3369, 1987), SV40 late promoter (Gheysen et al., J. Mol. Appl. Genet., 1:385-394, 1982), Adenovirus late promoter (Kaufman et al., Mol. Cell. Biol., 9:946, 1989), HSV TK promoter, etc. Transfer of a foreign gene into animal cells for its expression can be performed by any of the following methods, including the electroporation method (Chu et al., Nucl. Acid Res., 15:1311-1326, 1987), the calcium phosphate method (Chen et al., Mol. Cell. Biol., 7:2745-2752, 1987), the DEAE dextran method (Lopata et al., Nucl. Acids Res., 12:5707-5717, 1984; Sussman et al., Mol. Cell. Biol., 4:1642-1643, 1985), the lipofectin method (Derijard, Cell., 7:1025-1037, 1994; Lamb et al., Nature Genetics, 5:22-30, 1993; Rabindran et al., Science, 259:230-234, 1993), etc.

A protein of the present invention can be expressed as a fusion protein having the recognition site for a monoclonal antibody by introducing a recognition site (epitope) for a monoclonal antibody, the specificity of which has been established, into the N- or C-terminal of the protein of this invention. For this purpose, a commercial epitope-antibody system can be utilized (Jikken Igaku, Experimental Medicine, 13:85-90, 1995). Vectors are commercially available which are capable of expressing fusion proteins with β-galactosidase, maltose-binding protein, glutathione S-transferase, green fluorescence protein (GFP), and such, via the multi-cloning site.

To minimize the alteration of the properties of the protein of this invention due to the formation into a fusion protein, a method has been reported to prepare a fusion protein by introducing only a small epitope portion comprising several to ten amino acid residues. For example, the epitopes of polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), and such, and monoclonal antibodies to recognize these epitopes can be utilized as the epitope-antibody system for screening proteins binding to the protein of this invention (Jikken Igaku, Experimental Medicine, 13:85-90, 1995).

In the immunoprecipitation, immune complexes are formed by adding these antibodies to the cell lysate prepared using suitable surfactants. This immune complex consists of a protein of this invention, a protein capable of binding to the protein, and an antibody. The immunoprecipitation can also be performed using an antibody to a protein of this invention besides antibodies to the above-described epitopes. An antibody to a protein of this invention can be prepared by inserting a gene encoding a protein of this invention into an appropriate expression vector for E. coli to express it in the bacterium, purifying the protein thus expressed, and immunizing rabbits, mice, rats, goats, chicken, and such, with the purified protein. The antibody can also be prepared by immunizing the above-described animals with partial peptides of the protein of this invention.

Immune complexes can be precipitated using, for example, Protein A Sepharose and Protein G Sepharose in case where the antibody is a murine IgG antibody. In addition, in the case where the protein of this invention is prepared as a fusion protein with the epitope of, for example, GST, and such, the immune complex can be formed using a substance that specifically binds to these epitopes, such as glutathione-Sepharose 4B, and such, giving the same result as in the case where the antibody for the protein of this invention is used.

Immune precipitation, in general, may be carried out according to, or following the method described in the literature (Harlow, E. and Lane, D.: Antibodies, pp. 511-552, Cold Spring Harbor Laboratory publications, New York, 1988).

SDS-PAGE is generally used for the analysis of immunoprecipitated proteins, and bound proteins can be analyzed based on the molecular weights of proteins using a gel of an appropriate concentration. In this case, although proteins bound to a protein of this invention, in general, are hardly detectable by the usual protein staining method, such as Coomassie staining and silver staining, the detection sensitivity can be improved by culturing cells in a medium containing the radio isotope-labeled $^{35}$S-methionine and $^{35}$S-cysteine to label proteins inside the cells, and detecting the labeled proteins. Once the molecular weight of the protein is determined, the desired protein can be purified directly from SDS-polyacrylamide gel and sequenced.

In addition, screening of proteins binding to a protein of the present invention can be also performed using the West-western blotting method (Skolnik et al., Cell, 65:83-90, 1991). Specifically, cDNA is isolated from cells, tissues and organs (for example, tissue, cell or cultivated cell of heart, placenta, testis, thymus, peripheral leukocyte, etc.) in which protein binding to the protein of this invention is expected to be expressed, and transferred into a phage vector (for example, λgt11, ZAPII etc.), to prepare a cDNA library, which is then expressed on plates coated with a growth medium. The protein thus expressed is fixed on a filter, which is then reacted with the labeled, purified protein of this invention, and plaques expressing proteins bound to the protein of this invention can be detected by the label. Methods for labeling a protein of this invention include methods utilizing the binding activity of biotin and avidin, methods utilizing antibodies specifically binding to the protein of this invention, or peptides or polypeptides (for example, GST etc.) fused with the protein of this invention, methods utilizing the radioisotopes, methods utilizing fluorescence, etc.

Further, another embodiment of the screening method of this invention is exemplified by a method utilizing the 2-hybrid system using cells (Fields et al., Trends. Genet., 10:286-292, 1994; Dalton et al., Cell, 68:597-612, 1992; "MATCH-MARKER Two-Hybrid System", "Mammalian MATCHMARKER Two-Hybrid Assay Kit", "MATCH-MARKER One-Hybrid System" (Clonetech); "HybriZAP Two-Hybrid Vector system" (Stratagene)). In the two-hybrid system, a protein of the invention may be fused to the DNA binding domain of SRF or GAL4, and expressed in yeast. A cDNA library is constructed from cells predicted to express proteins that bind to the protein of the present invention, wherein the cDNA library is constructed in such a way that the proteins are expressed as fusion proteins with transcription activation regions of VP16 or. The cDNA library is transfected into the above yeast, and then positive clones are be detected to isolate the cDNA derived from the library (Expression of a protein that binds to the protein of the invention in yeast leads to the binding of the two proteins, and results in the activation of the reporter gene, which allows to detect positive clones). The protein encoded by the isolated cDNA may be obtained by introducing the cDNA into *E. coli* and expressing it therein. Thus, it is possible to prepare proteins that binds to a protein of the invention and genes encoding them. The reporter gene used in the two-hybrid system may be such as HIS3, Ade2, LacZ, CAT, luciferase, or PAI-I (plasminogen activator inhibitor type I), but is not limited thereto.

Screening for compounds, which bind to a protein of this invention, can be also carried out using affinity chromatography. For example, the protein of this invention is immobilized on a carrier in the affinity chromatography column, to which a test sample, which is expected to express a protein binding to the protein of this invention, is applied. Samples may be cell extracts, cell lysates, or else. After applying the test sample, the column is washed, and protein which binds to the protein of the invention can be obtained.

The obtained protein may be analyzed for its amino acid sequence to synthesize oligonucleotide probes, which may be used to screen a cDNA library to obtain a DNA encoding the protein.

A biosensor that utilizes surface plasmon resonance may be used to detect or measure the bound compound. Such sensor (as BIAcore (Pharmacia)) may enable to observe the interaction at real time using a small amount of protein without the need of labeling. Thus, it is possible to assess the interaction between the protein of the invention and samples using such biosensor as BIAcore.

Moreover, compounds that bind to a protein of the invention (including agonists and antagonists), which compounds are not always proteins, may be isolated using a variety of methods known to one skilled in the art. For instance, the protein of the invention may be fixed and exposed to synthetic compounds, a bank of natural compounds, or a random phage peptide library to screen a molecule that binds to the protein. Alternatively, high throughput screening using combinatorial chemistry may be performed (Wrighton et al., Science, 273: 458-464, 1996; Verdine, Nature, 384:11-13, 1996); Hogan Jr., Nature, 384:17-9, 1996).

Screening of a ligand that binds to a protein of the invention may be performed as follows. The extracellular domain of the protein of the invention is fused to the intracellular domain including the transmembrane domain of a hemopoietin receptor protein that has a known signal transducing ability to prepare a chimeric receptor. The chimeric receptor may be expressed on the cell surface of an appropriate cell line, favorably a cell line that is capable of growing only in the presence of an appropriate growth factor (growth factor-dependent cell line). Then, the cell line may be cultured in medium supplemented with a sample material in which a variety of growth factors, cytokines, or hematopoietic factors might be expressed. According to this method, the growth factor-dependent cell line can only survive and proliferate when the sample contains an appropriate ligand that specifically binds to the extracellular domain of the protein of the invention. The known hemopoietin receptor, such as thrombopoietin receptor, erythropoietin receptor, G-CSF receptor, and gp130 may be used. The partner for constructing a chimeric receptor for the screening system of the present invention is not limited to the above receptors as long as its intracellular domain provides a structure necessary for the signal transduction activity. The growth factor-dependent cell line may be an IL-3-dependent cell line such as BaF3 or FDC-P1.

In a rare case, the ligand that specifically binds to a protein of the invention may not be a soluble protein but a membrane-bound protein. In this case, screening can be performed using a protein comprising only the extracellular domain of the protein of the invention, or a fusion protein in which the extracellular domain is attached to a part of other soluble proteins. Such proteins are labeled before they are used for measuring the binding with the cells that are expected to express the ligand. The former protein comprising only the extracellular domain may be a soluble receptor protein artificially constructed through introducing a stop codon into the N-terminal region of the transmembrane domain, or a soluble protein such as NR10.2. The latter fusion protein may be a protein in which the Fc region of immunoglobulin G, or FLAG peptide is attached to the C-terminus of the extracellular domain. These labeled soluble proteins may be also useful for detection by the west-western method.

A chimeric protein of the extracellular domain of a protein of the invention and the Fc region of an antibody (such as human IgG) may be purified using a Protein A column. Such antibody-like chimeric protein retains the ligand binding ability. Thus, the protein may be appropriately labeled with an isotope and so on, and used for the screening of a ligand (Suda et al., Cell, 175:1169-1178, 1993). Some cytokines such as molecules of the TNF family primarily exist in a membrane bound form, so such ligands may be isolated by exposing the antibody-like chimeric protein to a variety of cells and selecting cells by the binding ability to the protein. Alternatively, ligands may be isolated according to the same method by using cells to which a cDNA library is introduced. Furthermore, the antibody-like chimeric protein may be also used as an antagonist.

The compounds obtained by the above screening may be a candidate for drugs that activate or inhibit the activity of a protein of the invention. It is possible to use such compounds for the treatment of diseases arising from abnormal expression or functional disorder of a protein of the present invention. The compound obtained by using the screening method of the invention includes compounds resulting from the modification of the compound having the activity to bind to the protein of the invention by adding, deleting, and/or replacing a part of the structure.

When using the isolated compound or a protein of the present invention (decoy type (soluble form)) as a pharmaceutical for humans and other mammals, for example, mice, rats, guinea-pigs, rabbits, chicken, cats, dogs, sheep, pigs, cattle, monkeys, sacred baboons, chimpanzees, the isolated compound can be directly administered or can be formulated into a dosage form using known pharmaceutical preparation methods. For example, according to the need, the drugs can be taken orally, as sugar-coated tablets, capsules, elixirs and microcapsules, or parenterally, in the form of injections of sterile solutions, suspensions with water, or any other pharmaceutically acceptable liquid. For example, the compounds can be mixed with pharmacologically acceptable carriers or medium, specifically, sterilized water, physiological saline, plant-oil, emulsifiers, solvents, surfactants, stabilizers, flavoring agents, excipients, vehicles, preservatives and binders, in a unit dose form required for generally accepted drug implementation. The amount of active ingredients in these preparations makes a suitable dosage acquirable within the indicated range.

Examples for additives which can be mixed to tablets and capsules are, binders such as gelatin, corn starch, tragacanth gum and gum arabic; excipients such as crystalline cellulose; swelling agents such as corn starch, gelatin and alginic acid; lubricants such as magnesium stearate; sweeteners such as sucrose, lactose or saccharin; flavoring agents such as peppermint, *Gaultheria adenothrix* oil and cherry. When the unit dosage form is a capsule, a liquid carrier, such as oil, can also be included in the above ingredients. Sterile composites for injections can be formulated following normal drug implementations using vehicles such as distilled water used for injections.

For example, physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as solubilizers; may be formulated with a buffer such as phosphate buffer and sodium acetate buffer; a pain-killer such as procaine hydrochloride; a stabilizer such as benzyl alcohol, phenol; and an anti-oxidant. The prepared injection is generally filled into a suitable ampule.

Methods well known to one skilled in the art may be used to administer the pharmaceutical compound to patients, for example as intraarterial, intravenous, percutaneous injections and also as intranasal, transbronchial, intramuscular or oral administrations. The dosage and method for administration vary according to the body-weight and age of the patient, the administration method, and such, but one skilled in the art can suitably select them. If said compound is encodable by a DNA, said DNA can be inserted into a vector for gene therapy to perform the therapy. The dosage and method for administration vary according to the body-weight, age, symptoms of a patient, and so on, but one skilled in the art can select them suitably.

For example, the dose of the protein (decoy type (soluble form)) may vary depending on the patient, target organ, disease type, and method for administration. However, it may be injected to a normal adult (body weight, 60 kg) at a dose of 100 μg to 10-20 mg per day.

For example, although there are some differences according to the symptoms, the dose of a compound that binds with the protein of the present invention, or a compound that inhibits the activity of the protein of this invention is about 0.1 mg to about 100 mg per day, preferably about 1.0 mg to about 50 mg per day, and more preferably about 1.0 mg to about 20 mg per day, when administered orally to a standard adult (weight 60 kg).

When the protein is administered parenterally in the form of an injection to a standard adult (weight 60 kg), although there are some differences according to the patient, target organ, symptoms and method of administration, it is convenient to intravenously inject a dose of about 0.01 mg to about 30 mg per day, preferably about 0.1 to about 20 mg per day, and more preferably about 0.1 to about 10 mg per day. Also, in the case of other animals, it is possible to administer an amount converted to 60 kg of body-weight or surface area.

The details of one or more embodiments of the invention are set forth in the accompanying drawings and the description below. Other features, objects, and advantages of the invention will be apparent from the description and drawings, and from the claims.

All publications and patents cited herein are incorporated by reference in their entirety.

DESCRIPTION OF DRAWINGS

FIG. 1 is a representation of the nucleotide sequence of AQ022781 (SEQ ID NO:34) identified in the gss database. The deduced amino acid sequence (SEQ ID NO:35) is shown under the predicted exon sequence. The YR motif and WS motif that were used as the target are boxed. Two "n" in the nucleotide sequence are also boxed.

FIG. 2 is a representation of partial amino acid sequences of NR10 (amino acid residues 198-238, 201-237, 196-237, 189-238, and 196-239 of SEQ ID NO:4, respectively) found in the sequence of AQ022781 (SEQ ID NO:35, which is part of SEQ ID NO:4), and those of known hemopoietin receptors having homology thereto. Identical residues are boxed with shadow, and similar residues are shadowed. Gap spaces are underlined. Known hemopoietin receptors are, from top, human gp130 (GenBank Accession No. NM002184.1; IL6ST; SEQ ID NO:36), human LIF receptor (GenBank Accession No. NM002310.1; LIFR; SEQ ID NO:37), human Oncostatin M receptor β subunit (GenBank Accession No. NM003999.1; OSMR; SEQ ID NO:38), human IL-12 receptor β2 subunit (GenBank Accession No. NM001559.1; IL12RB2; SEQ ID NO:39), and human NR6 (GenBank Accession No. AC003112; SEQ ID NO:40).

FIG. 3 is a representation of the nucleotide sequence of the full length NR10.1 cDNA (SEQ ID NO:1) that was obtained by combining the 5'- and 3'-RACE products. The deduced amino acid sequence encoded by NR10.1 is also shown (SEQ ID NO:2). The amino acid sequence predicted to be the secretion signal sequence is underlined. The predicted transmembrane domain is shadowed. Conserved cysteine residues and the WS motif are boxed.

FIG. 4 is a continuation of FIG. 3.

FIG. 5 is a continuation of FIG. 4.

FIG. 6 shows the nucleotide sequence of the full length NR10.2 cDNA (SEQ ID NO:3) that was obtained by combining the 5'- and 3'-RACE products. The deduced amino acid sequence encoded by NR10.2 is also shown (SEQ ID NO:4). The predicted secretion signal sequence is underlined. Conserved cysteine residues and the WS motif are boxed.

FIG. 7 is a continuation of FIG. 6.

FIG. 12 is a schematic illustration of the structure of the protein to be expressed from the expression vector construct.

FIG. 13 shows the nucleotide sequence of the full length NR10.3 cDNA (SEQ ID NO:16). The deduced amino acid sequence encoded by NR10.3 is also shown (SEQ ID NO:17). The predicted secretion signal sequence is underlined. The amino acid sequence predicted to be the transmembrane domain is colored. Conserved cysteine residues and the WS motif are boxed.

FIG. 14 is a continuation of FIG. 13.

DETAILED DESCRIPTION

Figure 8:
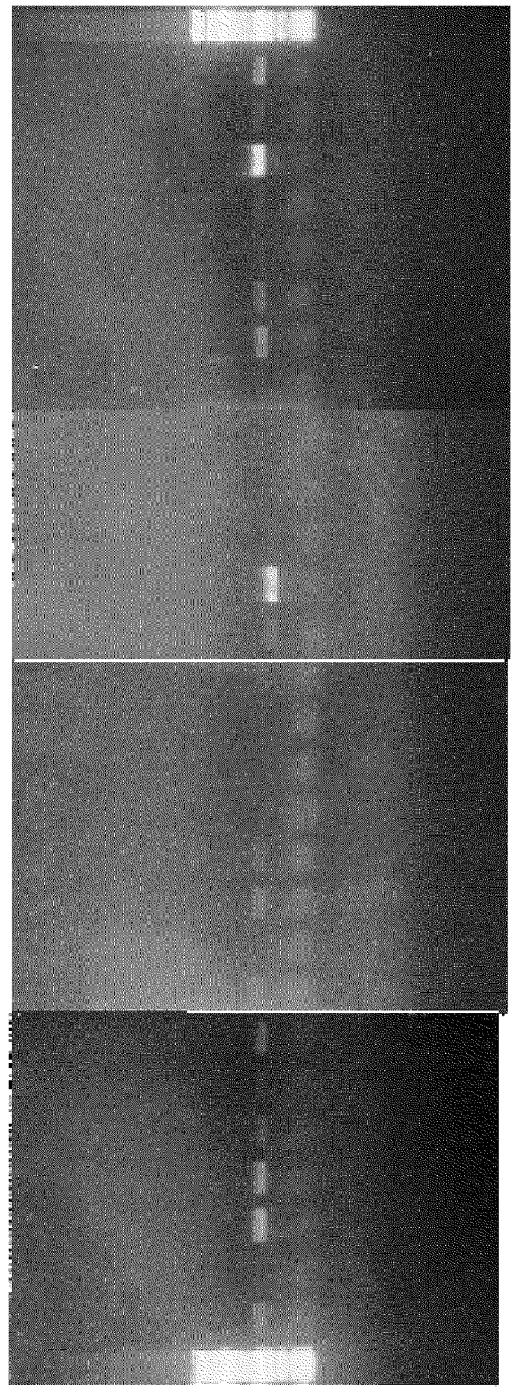
FIG. 8 shows photographs demonstrating the result of RT-PCR analysis of the expression pattern of the NR10.1 gene in human organs.

This invention will be explained in detail below with reference to examples, but it is not construed as being limited thereto.

Example 1

Isolation of NR10.1 and NR10.2 Genes (1) BLAST Search

The inventors aimed at finding another motif conserved among the hemopoietin receptor family, in addition to the Trp-Ser-Xaa-Trp-Ser (SEQ ID NO:22) motif (WS motif), in order to design an oligonucleotide probe including both motifs together. The inventors examined the sequence of other regions for another motif. As a result, they found a tyrosine or histidine residue in the extracellular domain of the family proteins, located 13 to 27 amino acids upstream of the WS motif, that is conserved at high frequency. They further examined the six amino acid residues located to the C-terminus from the Tyr/His residue for a consensus sequence that appears with a high-frequency, and found the amino acid following sequence: (Tyr/His)-Xaa-(Hydrophobic/Ala)-(Gln/Arg)-Hydrophobic-Arg (referred to as the YR motif in the following). However, the YR motif is not considered as a perfect consensus sequence, and also the combination of nucleotide sequences that can encode the motif is really complicated. Thus, it seemed very difficult to synthesize all the nucleotide sequences that encode the amino acid sequence and provide them as the probe for hybridization, a practical method of screening, or as the primer for RT-PCR.

Accordingly, the inventors examined for a specific method of screening for a novel hemopoietin receptor using the above motifs as the probe. As a result, they found it reasonable to perform a database search on computer using a query composed of a partial amino acid sequence of known hemopoietin receptors, a fragment including both motifs.

First, amino acid sequences that fulfilled the necessary condition to contain both motifs were designed to prepare a query for database search. Although the receptor family normally contains a spacer of 7 to 10 amino acids between the motifs, the spacer was fixed to 10 amino acids by taking average. It was expected that even if the length of spacer in target genes were different from that in the query, the gap would be filled by space so that it would not interfere the search. Moreover, the number of undetermined residues was minimized so as to increase the quality of the sequence and improve the sensitivity of detection. Thus, based on the sequence that appeared frequently in known hemopoietin receptors, three patterns were designed tentatively for the YR motif, two residues on both ends of the spacer, and the residues at the center and the C-terminus of the WS motif, respectively, as in Table 1.

TABLE 1

| YR motif | spacer amino acids | WS motif |
|---|---|---|
| YTVQVR (SEQ ID NO: 23) | AR XXXXXX GT (SEQ ID NO: 26) | WSEWSP (SEQ ID NO: 29) |
| YEARVR (SEQ ID NO: 24) | VQ XXXXXX GY (SEQ ID NO: 27) | WSDWSE (SEQ ID NO: 30) |
| YSLQLR (SEQ ID NO: 25) | CK XXXXXX GI (SEQ ID NO: 28) | WSPWSQ (SEQ ID NO: 31) |

Combining the YR motif, spacer and the WS motif described in Table 1 gives 27 different queries. The queries were used to search the nr database in GenBank using the TblastN program (Advanced TblastN 2.0.8). Parameters for search were set as Expect value=100, Descriptions=100, and Alignments=100. As a result, many of known hemopoietin receptors were identified positive, confirming that the method was working correctly. Then, the same queries were used to search on the EST database as well as the gss and htgs database in order to detect a sequence that could encode a novel hemopoietin receptor. However, the result did not yield any positive clones that appeared novel. It was considered that the limited variety of the above-mentioned 27 queries is the cause of the result. Accordingly, further preparation of a variety of sequences for the query was attempted, but the combination of the sequence became too complicated to continue the preparation manually. After all, the inventors decided to use partial amino acid sequences of known hemopoietin receptors that were fragmented so as to include both of the YR and WS motifs in order to prepare a query for database search.

Comparison of the genomic structure of the receptor family revealed that the YR and WS motifs are contained within a single exon in all examined known hemopoietin receptors. This suggests that the continuity and compatibility of both motifs may be also retained in the genomic sequence. Therefore, it was expected that the exon of a known hemopoietin receptor encoding both motifs are effective as the query to search for the target gene on the EST database, and the genomic database as well. Herein, human gp130 and human LIF receptor sequences were used as the known hematopoietin receptor sequence, because their structures have a relatively high similarity among the receptor family, and the similarity is expected to be shared in the target novel receptor. While the sequences of human gp130 and human LIF receptor were already known, the inventors used the amino acid sequence encoded by the cDNA that had been isolated by the inventors themselves using plaque hybridization and RT-PCR with a probe encoding the WS motif.

Based on the genomic structure, it is known that hemopoietin receptors are to contain an exon encoding the YR and WS motifs having a length of 50 to 70 amino acids. Accordingly, 29 amino acids to the N-terminus and 30 amino acids to the C-terminus from the first Tyr residue in the YR motif, a total of 60 amino acids were cut out of the sequence of human gp130 and human LIF receptor to prepare a query sequence for convenience' sake. The LIF receptor contains two WS motifs, and the second (on the C-terminal side) WS motif was selected taking into account the conservation of the YR motif. The above queries were used to search on the gss (Genomic Survey Sequence) and htgs database in GenBank using TblastN (Advanced TblastN 2.0.8). Parameters were set as Expect value=50, Descriptions=100, and Alignments=100.

The length of the selected query sequence, 60 amino acids, was not exactly the same as that of the actual exon sequence. However, taking into account that the length of this exon in known hemopoietin receptor genes differ somewhat according to each gene, and by taking the conservation of both YR and WS motifs as the index into much consideration it was decided that the difference may not interfere with the search. The gss and htgs database was used because these genomic sequences has not been fully analyzed due to its complexity, and thus, it was expected that they are suitable for identifying novel receptor genes. Since the queries were longer than the previous 27 artificial queries, parameters "Expect value=50, Descriptions=100, and Alignments=100" were set to reduce the sensitivity of detection so as to avoid increase of false positive clones that have homology to a region other than the motifs. Thus, it was expected that this enables detection of target genes by suppressing detection of such false positive clones showing homology at sequences other than the target motif sequence.

As a result, the search resulted in many hits of false positive clones, and those clones in which both YR and WS motifs were not encoded in the same reading frame, or that contained a stop codon between the motifs were discarded. Also, those clones containing only the YR motif but not the WS motif were discarded, because, as mentioned above, the YR motif is not a completely established consensus sequence. Therefore, the conservation of the WS motif was considered predominant. As a result, a single clone containing the human genomic sequence (GenBank Accession No. AQ022781) expected to encode a part of a novel hemopoietin receptor gene was selected, and the gene was named NR10.

AQ022781 (SEQ ID NO:34) is the terminal sequence of a BAC clone consisting of 459 bp, deposited in the gss database. It was the only clone that was also positive in both searches using partial amino acid sequences of human gp130 or LIF receptor as the query respectively. It was presumed that the reliability of the sequence might be low due the existence of two "n" in the middle and the nature of the deposition system of the Genomic Survey Sequence. Nevertheless, as shown in FIG. 1, a splice consensus sequence could be recognized as the "ag" sequence following the "c/t" rich sequence at 175th to the 218th bases, and it was predictable that it contains an exon starting from "atg" following the splice consensus sequence. Then, the predicted exon sequence was used to search on the nr database in GenBank using BlastX (Advanced BlastX 2.0.8). The results revealed that the exon has homology to many known hemopoietin receptor genes as shown in FIG. 2. The result was: (1) AQ022781 (SEQ ID NO:35) contains a YR motif, sequence YVIALR (SEQ ID NO:32), and that it retained a complete WS motif, sequence WSDWS (SEQ ID NO:33); (2) showing homology with several known hemopoietin receptors, and (3) both of the two Ser residues in the WS motif are encoded by AG(C/T). And thus, it was predicted that the gene could encode a novel hemopoietin receptor gene. The codon for Ser in the WS motif is generally AG(C/T) in most of the known hemopoietin receptors, but the second Ser residue in the EPO receptor, TPO receptor, and mouse IL-6 receptor is encoded by TCN. Indeed, most of the false positive clones containing by chance a WS motif-like sequence, the second Ser was mostly encoded by TCN. Thus, the Ser residue encoded by the AG(C/T) codon could be used as a marker for selection of positive clones. Accordingly, specific oligonucleotide primers were designed from the predicted exon sequence on AQ022781, and used for 5'-RACE and 3'-RACE method as below.

(2) Design of Oligonucleotide Primers

As described in (1), exon sites were predicted on AQ022781 sequences, and these sequences were used to design the following oligonucleotide primers specific for NR10. Three sense primers (NR10-S1, NR10-S2, and NR10-S3; oriented downstream) and three antisense primers (NR10-A1, NR10-A2, and NR10-A3; oriented upstream) were synthesized using the ABI 394 DNA/RNA synthesizer under a condition to attach a trityl group to the 5'-terminus. Then, the products were purified using an OPC column (ABI #400771) to obtain full-length primers.

```
NR10-S1:
                                       (SEQ ID NO: 5)
5'-ATG GAA GTC AAC TTC GCT AAG AAC CGT AAG-3'

NR10-S2:
                                       (SEQ ID NO: 6)
5'-CCA AAC GTA CAA CCT CAC GGG GCT GCA ACC-3'

NR10-S3:
                                       (SEQ ID NO: 7)
5'-GTC ATA GCT CTG CGA TGT GCG GTC AAG GAG-3'

NR10-A1:
                                       (SEQ ID NO: 8)
5'-agt agc ttg cgT TCT TCC TCA GCT ATT CCC-3'

NR10-A2:
                                       (SEQ ID NO: 9)
5'-CTT TGA CTC CTT GAC CGC ACA TCG CAG AGC-3'

NR10-A3:
                                       (SEQ ID NO: 10)
5'-GGT TGC AGC CCC GTG AGG TTG TAC GTT TGG-3'
```

The "n" at position 376 in AQ022781 sequence (FIG. 1) was assigned to be base "c" to design the primer sequences above, and thus, corresponding base at position 11 in NR10-A1 primer sequence was designed "g". According to the analysis of the consensus sequence for splicing the minimal exon on AQ022781 sequence was predicted to be starting from base "a" at position 211 to base "c" at position 399, the intron starting from the next "gt" sequence. However, the analysis of 3'-RACE products as described later revealed that the intron starts from the base "n" at position 376 or from base "g" at position 377. Therefore, as a result, the 11 bases shown in small caps of NR10-A1 primer sequence above can't bind correctly during PCR, while the corresponding sequence is not transcribed into mRNA. However, PCR reactions proceeded correctly, probably because the other 19 bases, the 3'-terminal sequences, were capable of annealing specifically.

(3) Cloning of the C-Terminus cDNA by 3'-RACE Method

In order to isolate the full-length cDNA of NR10, 3'-RACE PCR was performed using NR10-S1 and NR10-S2 primers described in (2) for primary and secondary PCR, respectively. PCR experiment was performed using Human Fetal Liver Marathon-Ready cDNA Library (Clontech #7403-1) as the template, and Advantage cDNA Polymerase Mix (Clontech #8417-1) on a thermal cycler (Perkin Elmer Gene Amp PCR System 2400). Under the following conditions, as a result, PCR products showing two different sizes by alternative splicing were obtained.

Condition of the primary PCR was as follows: a single cycle of "94° C. for 4 min.", 5 cycles of "94° C. for 20 sec, and 72° C. for 100 sec", 5 cycles of "94° C. for 20 sec, and 70° C. for 100 sec", 28 cycles of "94° C. for 20 sec, and 68° C. for 100 sec", a single cycle of 72° C. for 3 min, and termination at 4° C.

Condition of the secondary PCR was as follows: a single cycle of "94° C. for 4 min", 5 cycles of "94° C. for 20 sec, and 70° C. for 100 sec", 25 cycles of "94° C. for 20 sec, and 68° C. for 100 sec", a single cycle of 72° C. for 3 min, and termination at 4° C.

Two amplification products were obtained by the PCR and both of them were subcloned into the pGEM-T Easy vector (Promega #A1360), and the nucleotide sequences were determined. The transformation of the PCR product into the pGEM-T Easy vector was performed using T4 DNA ligase (Promega #A1360) in a reaction of 12 hrs at 4° C. Recombinants of the PCR products and pGEM-T vector were obtained by the transformation of E. coli DH5α strain (TOYOBO #DNA-903). Recombinants were selected by using Insert Check Ready Blue (TOYOBO #PIK-201). The nucleotide sequences were determined using the BigDye Terminator Cycle Sequencing SF Ready Reaction Kit (ABI/Perkin Elmer #4303150) and by analyzing with the ABI PRISM 377 DNA Sequencer. Nucleotide sequences of the whole insert fragment of six independent clones were determined. As a result, they were divided into two groups, each composed of 3 clones, based on the difference in length and sequence of the base pairs. It was confirmed that the difference of the product resulted from alternative splicing, and both of the obtained sequences are partial nucleotide sequences of NR10. The cDNA clone possibly encoding the long ORF including the transmembrane region was named as NR10.1, and the other possibly encoding a short ORF without the transmembrane region was named as NR10.2.

(4) Cloning of the N-Terminal cDNA by 5'-RACE

In order to isolate the full-length cDNA of NR10, 5'-RACE PCR was performed using NR10-A1 and NR10-A2 primers of Example 2 for primary and secondary PCR, respectively. As in 3'-RACE, PCR experiment was performed using Human Fetal Liver Marathon-Ready cDNA Library as the template, and Advantage cDNA Polymerase Mix on a thermal cycler (Perkin Elmer Gene Amp PCR System 2400). Under the same condition to those described in (3), PCR products of three different sizes were obtained. All of the three products were subcloned into the pGEM-T Easy vector as described above to determine the nucleotide sequence. The transformation of the PCR products into the pGEM-T Easy vector was performed using T4 DNA ligase in a reaction for 12 hrs at 4° C. The recombinants of the PCR products and pGEM-T vector were obtained by transformation of E. coli DH5α strain, and selection of the recombinants were done using Insert Check Ready Blue as described above. The nucleotide sequences were also determined as above using the BigDye Terminator Cycle Sequencing SF Ready Reaction Kit and the ABI PRISM 377 DNA Sequencer for analysis. The result revealed that the obtained three 5'-RACE products with different sizes were derived from the same mRNA transcript. The difference in size was due to incomplete extension reaction in the 5'-RACE and the possibility was denied that they were derivatives of alternative splicing. Yet, even the cDNA clone with the longest extension product among the three 5'-RACE products did not contain the 5'-terminus of the full-length sequence. Furthermore, another attempt using NR10-A2 and NR10-A3 primers of (2) for primary and secondary PCR, respectively, ended in a similar result. Accordingly, in order to perform another 5'-RACE elongation reaction, new oligonucleotide primers were designed proximally to the N-terminus of the obtained nucleotide sequence. Two antisense primers, NR10-A4 and NR10-A5, (upstream orientation) as below were prepared according to Example 2.

(SEQ ID NO: 11)
NR10-A4: 5'-ATC AGA TGA AAC AGG CGC CAA CTC AGG-3'

(SEQ ID NO: 12)
NR10-A5: 5'-TGG TTT CAC ACG GAA AAT CTT AGG TGG-3'

As described above, 5'-RACE PCR was performed using Human Fetal Liver Marathon-Ready cDNA Library as the template, and NR10-A4 and NR10-A5 primer for primary and secondary PCR, respectively. Conditions for PCR, method of subcloning, and method for determining the nucleotide sequence were as those described in (3). However, results of the sequence determination revealed that again only incomplete elongation products, in which the extension reaction stopped at the same site as by the 5'-RACE PCR using NR10-A1, NR10-A2, and NR10-A3 primers above, were obtained. It was possible that NR10 mRNA forms a tertiary conformation at that position so that it blocks the synthesis of primary cDNA strand. There is also the possibility that the nucleotide sequence of the upstream region from that position might have a high G/C content, which could block the PCR reaction. Anyway, it might be the case that the quality of the library used to prepare the cDNA library might have been low. Accordingly, the template for PCR was substituted with Human Placenta Marathon-Ready cDNA library (Clontech #7411-1) as described in the following. This human Placenta derived material was chosen according to the result tissue distribution of NR10 gene by RT-PCR analysis described later.

(5) Cloning of the N-Terminal cDNA Through Continuous Extension by 5'-RACE

To isolate the N-terminal sequence of a cDNA clone corresponding to the full length NR10, 5'-RACE PCR was performed using NR10-A4 and NR10-A5 primers of (4) for primary and secondary PCR, respectively. Human Placenta Marathon-Ready cDNA library was used as the template due to reasons mentioned above. Advantage cDNA Polymerase Mix was used in the PCR experiment. 5'-RACE PCR was conducted using the thermal cycler Perkin Elmer Gene Amp PCR System 2400 under the following conditions to obtain a PCR product of single size.

The condition for primary PCR was as follows: a single cycle of "94° C. for 4 min", 5 cycles of "94° C. for 20 sec, and 72° C. for 2 min", 5 cycles of "94° C. for 20 sec, and 70° C. for 2 min", 28 cycles of "94° C. for 20 sec, and 68° C. for 90 sec", a single cycle of 72° C. for 3 min, and termination at 4° C.

The condition for secondary PCR was as follows: a single cycle of "94° C. for 4 min", 5 cycles of "94° C. for 20 sec, and 70° C. for 90 sec", 25 cycles of "94° C. for 20 sec, and 68° C. for 90 sec", a single cycle of 72° C. for 3 min, and termination at 4° C.

The obtained PCR product was subcloned into pGEM-T Easy vector as described in Example 3, and the nucleotide sequence was determined. The nucleotide sequences of the whole insert fragment from 4 independent clones of transformants revealed that the clones contain the N-terminal sequence of the full length NR10 cDNA clone. Then, the nucleotide sequence determined by the 5'RACE-PCR and those determined by 3'-RACE in (3) were combined to finally obtain the full length nucleotide sequence of full length NR10.1 and NR10.2 cDNA. The nucleotide sequence determined for NR10.1 cDNA (SEQ ID NO:1) and the amino acid sequence encoded by the sequence (SEQ ID NO:2) are shown in FIGS. 3 to 5. The nucleotide sequence determined for NR10.2 cDNA (SEQ ID NO:3) and the amino acid sequence encoded by the sequence (SEQ ID NO:4) are shown in FIGS. 6 and 7.

According to the determination of the full-length nucleotide sequence of NR10 cDNA, it was revealed that the "n" at position 281 of AQ022781 (FIG. 1) was actually "t". Whereas, the "n" at position 376 was not determined because the intron starts from the base around this "n". Nevertheless, no matter which nucleotide is used to replace the "n" at position 376, the sequence did not give a consensus sequence for splicing (ag/gtaag etc.). Considering the features of the information of the gss database, it was presumed that the sequence [an/gcaag] around the "n" at position 376 was actually [ag/gtaag]. Determination of the full-length nucleotide sequence of NR10.1 and NR10.2 revealed that these two genes are connected to a different exon at the object obscure splicing site through alternative splicing, and the C-terminus thereafter encoded different amino acid sequences. Their primary structure indicates that NR10.1 may encode a transmembrane type hemopoietin receptor protein consisting of 652 amino acids, and that NR10.2 may encode a soluble secretion type receptor-like protein consisting of 252 amino acids. The structural features of these NR10 are as follows:

First, it is predicted that the sequence from the 1st Met to the 32nd Ala in the common extracellular domain of NR10.1 and NR10.2 is the typical secretion signal sequence. Herein, the 1st Met is presumed to be the translation initiation site because there exists an in frame termination codon at the (−2) position. Next, a typical ligand-binding domain exists in the region from the 43rd Cys to the 53rd Cys or the 55th Trp residue. In addition, the 81st and 94th Cys correspond to the Cys residue repeat conformation well conserved among other hemopoietin receptor family. Furthermore, a Pro-rich region (PP-W motif) beginning at the consecutive Pro residues at positions 137 and 138 to the 157th Trp residue is conserved, and residues from the 210th Tyr to 215th Arg corresponds to the YR motif above. A typical WSXWS-box (WS motif; SEQ ID NO:22) is also found at residues from the 224th Trp to 228th Ser.

The open reading frame (ORF) of NR10.2 encodes 24 amino acids from the WSXWS sequence (SEQ ID NO:22) and terminates at the stop codon thereafter. Thus, it encodes a soluble hemopoietin receptor-like protein without a transmembrane region. On the other hand, the ORF of NR10.1 contains a typical transmembrane domain of 24 amino acids from the 533rd Ile to the 556th Leu residue following the above motifs. In addition, the intracellular domain adjacent to the transmembrane domain contains Pro residues at positions 571 and 573, corresponding to the Box-1 consensus sequence (PXP motif) well conserved among other hemopoietin receptors and is considered to be implicated in signal transduction. These features above confirm that the NR10 gene encodes a novel hemopoietin receptor protein.

Example 2

Tissue Distribution Determination and Expression Pattern Analysis of NR10 Gene by RT-PCR mRNA was detected using the RT-PCR method to analyze the expression distribution and the expression patterns of NR10.1 and NR10.2 gene in different human organs. Oligonucleotide primers with the following sequences were synthesized for RT-PCR analysis. NR10-S0 primer was used as a sense primer (downstream orientation), and NR10.1-A0 and NR10.2-A0 primer were used as antisense primers (upstream orientation). The primers were synthesized and purified as described in Example 2. While NR10-S0 was designed so as to correspond to common sequences of NR10.1 and NR10.2, NR10.1-A0 and NR10.2-A0 were designed according to specific sequences of NR10.1 and NR10.2, respectively.

```
hNR10-S0:
                                   (SEQ ID NO: 13)
5'-GCA TTC AGG ACA GTC AAC AGT ACC AGC-3' hNR10.1-A0:
                                   (SEQ ID NO: 14)
5'-AGC TGG AAT CCT CAG GGT GGC CAC TGG-3' hNR10.2-A0:
                                   (SEQ ID NO: 15)
5'-GCC CAT CAC CAG AGT AGA CAG GAC GGG-3'
```

The templates used were Human Multiple Tissue cDNA (MTC) Panel I (Clontech #K1420-1), Human MTC Panel II (Clontech #K1421-1), Human Immune System MTC Panel (Clontech #K1426-1), and Human Fetal MTC Panel (Clontech #K1425-1). PCR was performed using Advantage cDNA Polymerase Mix (Clontech #8417-1) on a thermal cycler (Perkin Elmer Gene Amp PCR System 2400). NR10-S0 and NR10.1-A0 were used in pair for the detection of NR10.1. For the detection of NR10.2, [NR10-S0 and NR10.2-A0] primer set was used. PCR was performed by following condition to amplify the target gene: a single cycle of "94° C. for 4 min", 5 cycles of "94° C. for 20 sec, and 72° C. for 1 min", 5 cycles of "94° C. for 20 sec, and 70° C. for 1 min", 25 cycles of "94° C. for 20 sec, and 68° C. for 1 min", a single cycle of 72° C. for 3 min, and termination at 4° C.

Figure 9:
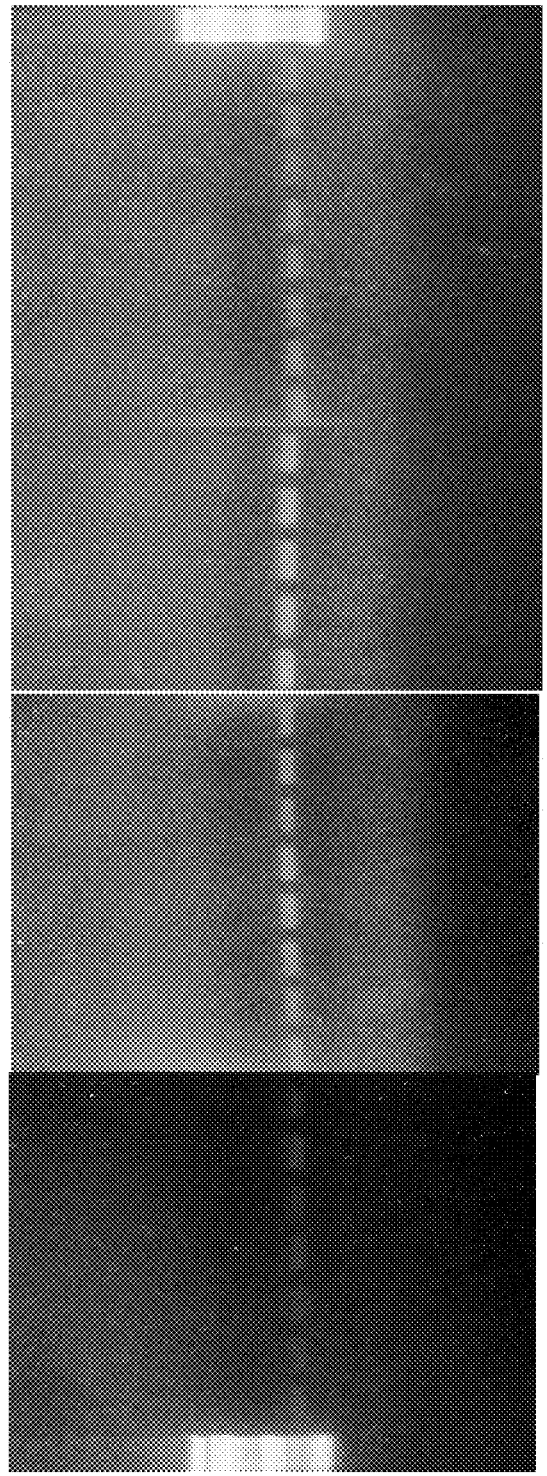
FIG. 9 shows photographs demonstrating the result of RT-PCR analysis of the expression pattern of the NR10.2 gene in human organs.

As shown in FIG. 9, the result was that constitutive gene expression of NR10.2 was detected at almost a constant level in all examined human organs and tissues derived mRNA. In contrast, as shown in FIG. 8, NR10.1 gene expression was detected in restricted tissues or organs, and its expression level varied significantly. Performing PCR using human G3PDH primers under the above condition and detecting the expression of the house-keeping gene G3PDH, it was confirmed that the number of mRNA copies among the template mRNA had been normalized. The expression of NR10.1 gene was found in organs as follows: in human adult, it was strongly expressed in heart, placenta, testis, thymus, and peripheral leukocytes, while weak expression was detected in spleen, bone marrow, prostate, ovary, pancreas, and lung; in human fetus, strong expression was detected in skeletal muscle, thymus, heart, and kidney, while weak expression was detected in lung, liver, and spleen. On the other hand, no expression could be detected in brain, skeletal muscle, kidney, small intestine, or colon in human adult, nor in fetal brain.

The size of the PCR amplification product was 480 bp and 243 bp for NR10.1 and NR10.2, respectively, which was consistent with the sizes calculated from the determined nucleotide sequences. Thus, the products were considered to be products of specific PCR amplification reaction. This was further confirmed by Southern blotting as in the following, and the possibility of that they were non-specific PCR amplification products was denied.

Due to the fact that a strong expression of NR10.1 gene was mainly detected in those organs containing immune responsible cells and hematopoietic cells and considering the gene expression distribution of NR10.1, the possibility that NR10 functions as a novel hemopoietin receptor was strongly suggested. Additionally, the fact that the expression was also distributed among cells of the genital system and the endocrine system as well as in heart suggested that NR10 could regulate not only the immune system and hematopoietic system but also diverse physiological functions in the body as well.

The fact that expression of NR10.2 was detected in all organs indicates the possibility that cells constituting the subject organs of the analysis produce active secretory type protein. It is possible that the expression of NR10 gene is strictly regulated in particular tissues or cell populations through transcriptional regulation and alternative splicing that determines the functional specificity of these tissues and cells.

Example 3

Verification of the Specificity of PCR Products by Southern Blotting

In order to verify the specificity of amplification, the RT-PCR amplified target gene product in Example 2 was subjected to Southern blotting using cDNA fragments specific for NR10.1 and NR10.2, respectively, as a probe. At the same time, the amount of RT-PCR product was quantitatively detected to assess relative gene expression levels among different human organs. The RT-PCR product was electrophoresed on an agarose gel, blotted onto a charged nylon membrane (Hybond N(+), Amersham cat#RPN303B), and subjected to hybridization. cDNA fragments of NR10.1 and NR10.2 obtained in Example 3 were used as probes specific for respective genes. Probes were prepared using the Mega Prime Kit (Amersham cat#RPN1607), and labeled with radioisotopoe, [α-$^{32}$P]-dCTP (Amersham cat#AA0005). Hybridization was performed using Express Hyb-ridization Solution (Clontech #8015-2), and after the prehybridization at 68° C. for 30 min, heat denatured labeled probe was added to conduct hybridization at 68° C. for 120 min. After subsequent wash in (1) 1×SSC/0.1% SDS at room temperature for 5 min, (2) 1×SSC/0.1% SDS at 50° C. for 30 min, and (3) 0.1×SSC/0.1% SDS at 50° C. for 30 min, the membrane was exposed to an Imaging Plate (FUJI #BAS-III), and NR10 specific signal was detected using the Image Analyzer (FUJIX, BAS-2000 II).

Figure 10:
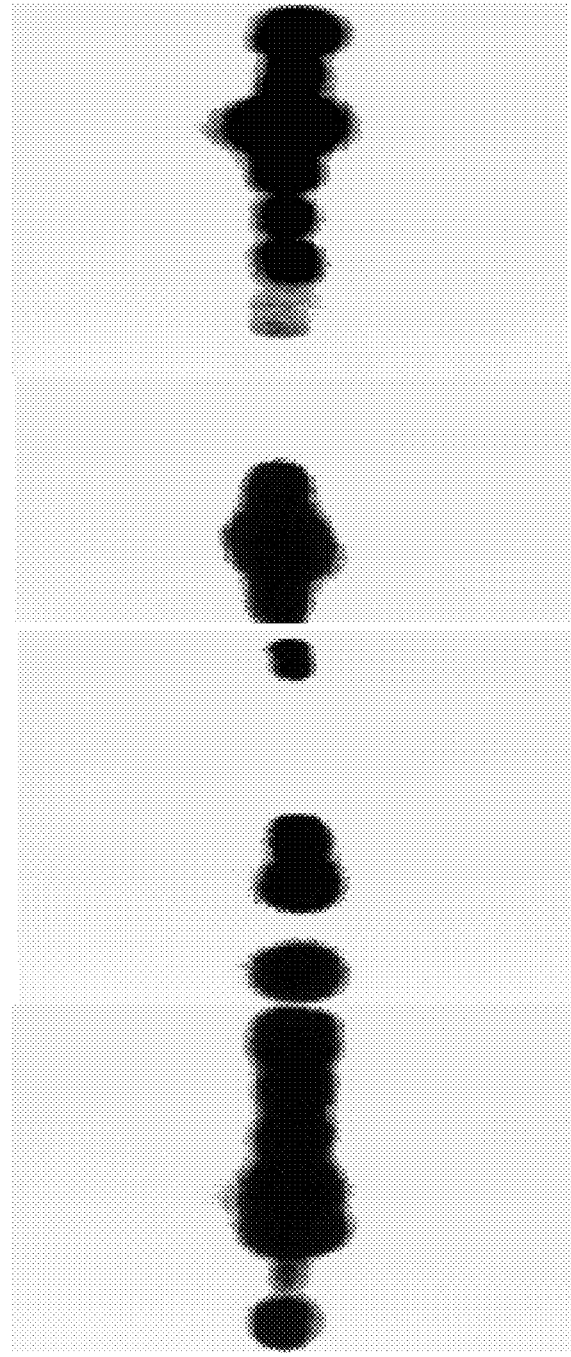
FIG. 10 shows a photograph demonstrating the result of quantification of the NR10.1 gene expression in human organs by Southern blotting.
Figure 11:
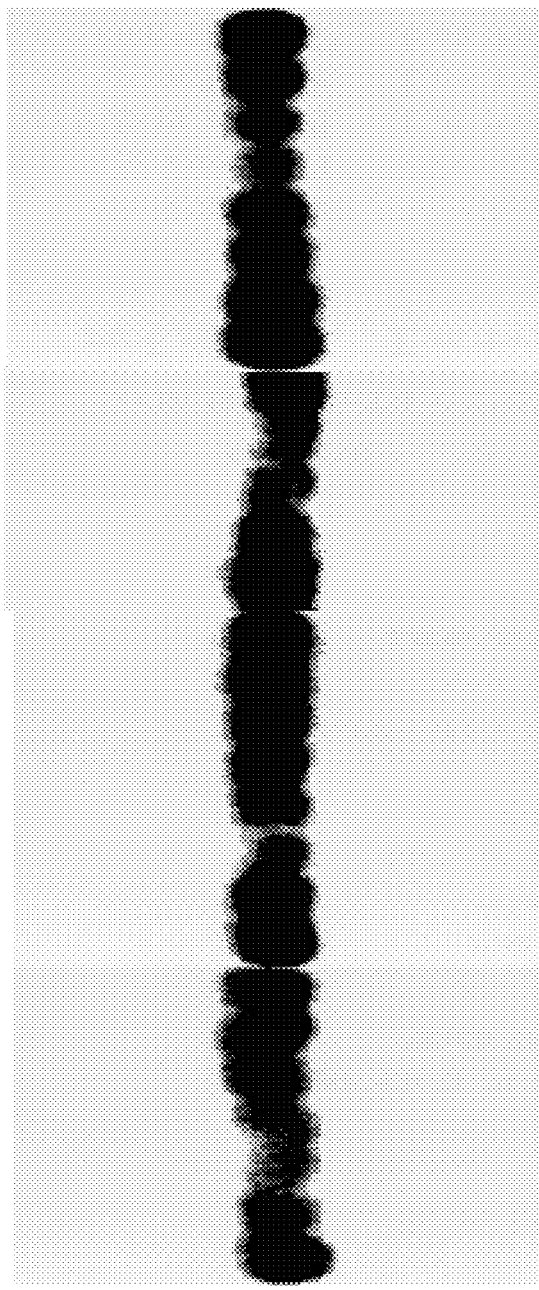
FIG. 11 shows a photograph demonstrating the result of quantification of the NR10.2 gene expression in human organs by Southern blotting.

Detected results for NR10.1 and NR10.2 are shown in FIGS. 10 and 11, respectively. The amplified product in the previous RT-PCR was verified as specific amplification products of respective genes. Furthermore, the result of quantification of relative expression level among each tissues supported above-mentioned assessment. The detection method for target gene expression using RT-PCR and Southern blotting in combination is known to have extremely high sensitivity as compared to other methods for expression analysis. Nevertheless, NR10.1 expression was not detected in the neuronal system such as adult and fetal brains, in adult digestive tissues. Moreover, no expression was detected in adult skeletal muscle or kidney, where strong expression was recognized in fetus.

Example 4

Northern Blot Analysis of NR10 Gene Expression

Northern blot analysis of NR10 gene expression was performed to examine the expression pattern of NR10 gene in human organs and human tumor cell lines, and to determine the size of NR10 transcripts. In addition, the possibility of whether splice variants other than NR10.1 or NR10.2 existed was examined. Human Multiple Tissue Northern (MTN) Blot (Clontech #7760-1), Human MTN Blot II (Clontech #7759-1), Human MTN Blot III (Clontech #7767-1), and Human Cancer Cell Line MTN Blot (Clontech #7757-1) were used.

The cDNA fragments obtained by 5'-RACE in Example 1 (5) were used as the probes. Probes were prepared as described in Example 3, using the Mega Prime Kit, and labeled with [α-$^{32}$P]dCTP. Hybridization was performed using Express Hyb-ridization Solution, and after prehybridization at 65° C. for 30 min heat denatured probes were added to conduct hybridization at 65° C. for 16 hr. After subsequent wash in (1) 1×SSC/0.1% SDS at room temperature for 5 min, (2) 1×SSC/0.1% SDS at 48° C. for 30 min, and (3) 0.5×SSC/0.1% SDS at 48° C. for 30 min, the membrane was exposed to an Imaging Plate as described above, and an attempt to detect NR10 specific signal was made using an Image Analyzer.

The method, unexpectedly, failed to detect any signal in any of the examined human organs. This could be because Northern blotting has a significantly lower sensitivity than RT-PCR and thus failed to detect mRNA with low expression level.

Example 5

Plaque Screening

The above procedure utilized PCR cloning for obtaining the full-length cDNA of NR10 gene. There is always the possibility that a point mutation in the product is introduced by PCR cloning. Thus, in order to reconfirm the nucleotide sequence of the above cDNA clone, plaque hybridization was performed using a lambda phage cDNA library to reisolate the target gene. Human Placenta cDNA library (Clontech #HL1144X), in which the expression of NR10 gene was confirmed as a result of NR10 gene expression analysis by RT-PCR, was used for the plaque screening. The cDNA fragments obtained by 5'-RACE in Example 1 (5) were used as the probe, as above. Probes were prepared and labeled as in Example 3, using the Mega Prime Kit, and labeled with [α-$^{32}$P]dCTP. Hybridization was performed using Express Hyb-ridization Solution, and after prehybridization at 65° C. for 30 min heat denatured probes were added to conduct hybridization at 65° C. for 16 hr. After subsequent wash in (1) 1×SSC/0.1% SDS at room temperature for 5 min, (2) 1×SSC/0.1% SDS at 58° C. for 30 min, and (3) 0.5×SSC/0.1% SDS at 58° C. for 30 min, the membrane was exposed to an X-ray film (Kodak, cat#165-1512) to detect NR10 positive plaques.

As a result, no positive clone was obtained. As described in Example 4, one reason why the cDNA clone couldn't be isolated might be that the expressed copy numbers of the target gene was too small. To isolate the target gene, it is favorable to perform plaque hybridization using a lambda phage cDNA library derived from human fetal skeletal muscle, which showed the highest expression level of the gene by RT-PCR analysis.

Example 6

Ligand Screening (1) Construction of NR10 Chimeric Receptor

A screening system is constructed for searching a ligand, a novel hemopoietin, that can specifically bind to NR10. First, the cDNA sequence encoding the extracellular region of NR10.1 (from the 1st Met to the 238th Glu or 1st Met to the 532nd Glu) was amplified by PCR, and this DNA fragment is bound in frame to DNA fragments encoding the transmembrane region and the intracellular region of a known hemopoietin receptor to prepare a fusion sequence encoding a chimeric receptor. As described above, there are several candidates for the partner, the known hemopoietin receptor, and among them, the human TPO receptor (Human MPL-P) is selected. Specifically, after amplifying the DNA sequence encoding the intracellular region that includes the transmembrane region of the human TPO receptor by PCR, this sequence was bound to the cDNA sequence encoding the extracellular region of NR10.1 in frame, and was inserted into a plasmid vector (pEF-BOS) expressible in mammalian cells. The constructed expression vector was named pEF-NR10/TPO-R. A schematic diagram of the structure of the constructed NR10/TPO-R chimeric receptor is shown in FIG. 12. Together with an expression vector pSV2bsr (Kaken Pharmaceutical) containing Blastcidin S resistant gene, the NR10/TPO-R chimeric receptor-expressing vector was introduced into the growth factor-dependent cell line Ba/F3, and was forced for expression. Gene-introduced cells were selected by culturing under the coexistence of 8 µg/ml of Blastcidin S hydrochloride (Kaken Pharmaceutical) and IL-3. By transferring the obtained chimeric receptor-introduced cells to an IL-3-free medium, culturing by adding materials expected to contain a target ligand, it is possible to conduct screening which makes use of the fact that survival/proliferation of the cell is possible only when a ligand that specifically binds to NR10 is present.

(2) Preparation of NR10/IgG1-Fc Soluble Fusion Protein

NR10/IgG1-Fc soluble fusion protein was prepared to utilize it for searching cell membrane-bound type ligands, or to detect soluble ligands through BIAcore (Pharmacia) and West-western blotting. A fusion sequence encoding the soluble fusion protein was prepared by binding the DNA fragment encoding the extracellular region of NR10.1 (from the 1st Met to the 238th Glu or 1st Met to the 532nd Glu) prepared in Example 6(1) with the DNA fragment encoding the Fc region of human immunoglobulin IgG1 in frame. A schematic diagram of the structure of the soluble fusion protein encoding the constructed NR10/IgG1-Fc is shown in FIG. 12. This fusion gene fragment was inserted into a plasmid vector (pEF-BOS) expressible in mammalian cells, and the constructed expression vector was named pEF-NR10/IgG1-Fc. After forcing expression of this pEF-NR10/IgG1-Fc in mammalian cells, and selection of stable gene-introduced cells, the recombinant protein secreted into the culture supernatant can be purified by immunoprecipitation using anti-human IgG1-Fc antibody, or by affinity columns, etc.

(3) Construction of an Expression System of NR10.2 and Purification of the Recombinant NR10.2 Protein The recombinant NR10.2 protein was prepared to utilize it for searching cell membrane-bound ligands, or the detection of soluble ligands using BIAcore (Pharmacia) or West-western-blotting. The stop codon of the amino acid coding sequence of NR10.2 cDNA was replaced by point mutation to a nucleotide sequence encoding an arbitrary amino acid residue, and then, was bound to the nucleotide sequence encoding the FLAG peptide in frame. This bound fragment was inserted into a plasmid vector expressible within mammalian cells, and the constructed expression vector was named pEF-BOS/NR10.2 FLAG. FIG. 12 shows a schematic diagram of the structure of the insert NR10.2 FLAG within the constructed expression vector. After forced-expression of this pEF-BOS/NR10.2 FLAG in mammalian cells and selection of stable gene-introduced cells, the recombinant protein secreted into the culture supernatant can be immunoprecipitated using anti-FLAG peptide antibody, or may be purified by affinity columns, etc.

Example 7

Isolation of NR10.3 Gene (1) Design of Oligonucleotide Primers

Isolation of NR10.1 gene was conducted again to obtain the cDNA comprising a continuous full-length coding sequence. First, 5'-UTR and 3'-UTR within the nucleotide sequence of NR10.1 cDNA was selected to design sense and antisense primers (downstream and upstream orientation, respectively) with sequences as follows. Primers were synthesized as in Example 1 (2) on an ABI 394 DNA/RNA Synthesizer under the condition where a trityl group was attached to the 5'-terminus. The product was purified using an OPC column (ABI #400771) to obtain full-length primers.

```
NR10-5UTR (SN);
                                       (SEQ ID NO: 18)
5'-CCC CTG ATA CAT GAA GCT CTC TCC CCA GCC-3'

NR10-3UTR (AS);
                                       (SEQ ID NO: 19)
5'-CCA GTC TTC GGA GAT GGT TCT CTT GGG GCC-3'
```

(2) PCR Cloning

In order to isolate the full length CDS of NR10, PCR cloning was performed using NR10-5UTR and NR10-3UTR primers as sense and antisense primers, respectively. Human Placenta Marathon-Ready cDNA Library (Clontech #7411-1) was used as the template. PCR experiment was performed using the Advantage cDNA Polymerase Mix (Clontech #8417-1) on a thermal cycler Perkin Elmer Gene Amp PCR System 2400. PCR was performed by a single cycle of "94° C. for 4 min", 5 cycles of "94° C. for 20 sec, and 72° C. for 90 sec", 5 cycles of "94° C. for 20 sec, and 70° C. for 90 sec", 28 cycles of "94° C. for 20 sec, and 68° C. for 90 sec", a single cycle of 72° C. for 3 min, and was terminated at 4° C. As a result, an amplification product of 2119 bp was obtained.

The obtained PCR product was subcloned into pGEM-T Easy vector (Promega #A1360) as in Example 1 (3), and the nucleotide sequence was determined. Recombination of the PCR product into the pGEM-T Easy vector was performed using T4 DNA Ligase (Promega #A1360) in a reaction of 12 hrs at 4° C. The recombinant of the PCR product and the pGEM-T Easy vector was obtained by transformation of DH5 alpha E. coli (Toyobo#DNA-903), and Insert Check Ready Blue (TOYOBO #PIK-201) was used for the selection. The nucleotide sequence was determined using the BigDye Terminator Cycle Sequencing SF Ready Reaction Kit (ABI/Perkin Elmer #4303150) and the ABI PRISM 377 DNA Sequencer. The nucleotide sequences of the whole insert fragments from 5 independent clones of the recombinant were determined. As a result, the nucleotide sequence of a cDNA clone that may encode the full length CDS of NR10 including the transmembrane region was determined. However, the determined sequence was not recognized as that of NR10.1, but instead it was a cDNA clone which could encode a transmembrane type of receptor protein of 662 amino acids. The clone was named NR10.3 so as to distinguish it from the NR10.1.

E. coli containing this cDNA clone was deposited in National Institute of Bioscience and Human-Technology, Agency of Industrial Science and Technology.

Depositary institution: National Institute of Bioscience and Human-Technology, Agency of Industrial Science and Technology, Ministry of International Trade and Industry.

Address: 1-1-3 Higashi, Tsukuba, Ibaraki 305-8566, Japan.

Deposition date (original date): Jul. 23, 1999 (Heisei 11).

Accession No. Seimeiken Jyouki Dai 6793 Go (FERM BP-6793).

As compared with NR10.1, the NR10.3 cDNA clone has a single nucleotide deletion in the adenine cluster at the proximity of the stop codon leading to a frame shift. Thereby, NR10.1 and NR10.3 exhibit difference in the reading frame of the amino acid sequence proximal to the stop codon. The decided nucleotide sequence of NR10.3 and the amino acid sequence encoded by it are shown in SEQ ID NOs:16 and 17, respectively, as well as in FIGS. 13 and 14.

(3) Significance of the Existence of NR10.1 and NR10.3

As described above, the difference between NR10.1 and NR10.3 is caused by the difference of a single nucleotide at a position near the stop codon, and not by different transcription products due to splicing mutants. Since NR10.1 and NR10.3 cDNA clone are identical except for the deletion of the single nucleotide, the hematopoietic factor receptor proteins encoded by them are presumed to be functionally equivalent. However, such single nucleotide deletion or point mutation could play a role in certain disease, or the sequence diversity may be caused family or race dependently.

Example 8

Chromosomal Location of the NR10

(1) Design of Oligonucleotide Primers

In order to construct a chromosome map of NR10, an oligonucleotide primer, NR10-intron, with the following sequence was synthesized. NR10-intron primer was designed as a sense primer (downstream orientation) by selecting the sequence of an intron site, not transcribed into NR10 mRNA, within the sequence of AQ022781 deposited in the gss database. The primer was synthesized as described in Example 1 (2) using an ABI 394 DNA/RNA Synthesizer under condition where a trityl group is attached to the 5'-terminus, and purified on an OPC column (ABI #400771) to obtain a full-length product.

```
NR10-intron (SN):
                                          (SEQ ID NO: 20)
5'-CTG TGT AAG TAC CAA TTG TTC CCA GGC-3'
```

(2) Chromosome Mapping of the NR10 Gene

In order to make a chromosome map of NR10, PCR analysis was performed using respective DNA obtained from human/mouse somatic cell system having 24 chromosomes (Dubois et al., Genomics, 16:315-319, 1993).

NR10-intron primer of Example 8 (1) and NA10-A1 primer produced in Example 1 (2) were used as sense and antisense primers, respectively. PCR experiment was performed using Advantage cDNA Polymerase Mix (Clonetech #8417-1) on a thermal cycler Perkin Elmer Gene Amp PCR System 2400 under the following PCR condition. As a result, a 359 bp amplification product was amplified, which suggested the existence of NR10 gene on human chromosome 5.

PCR was performed by a single cycle of "94° C. for 4 min", 5 cycles of "94° C. for 20 sec, and 70° C. for 60 sec", 28 cycles of "94° C. for 20 sec, and 68° C. for 60 sec", and a single cycle of 72° C. for 3 min, and was terminated at 4° C.

The obtained PCR product was cloned into pGEM-T Easy vector (Promega #A1360) as described in Example 1 (3), and the nucleotide sequence was determined using an ABI PRISM 337 DNA Sequencer. Analysis of the nucleotide sequence of the whole insert fragment from eight independent recombinant clones confirmed that the PCR product had the nucleotide sequence of the target genomic DNA fragment containing a partial sequence of NR10, and not a product due to non-specific amplification.

The above result also confirmed that the primer set was working in a specific manner. Subsequently, the locus of the NR10 gene was determined using the GeneBridge 4 radiation hybrid panel 93 (Walter et al., Nature Genetics, 7:22-28, 1994). PCR analysis was performed using the GeneBridge 4 radiation hybrid panel 93 as a template and N10-intron and NR10-A1 primers under the same condition as above. The amount of amplified products from respective hybrids were quantitatively assessed as plus or minus, and the result was converted to binary code. Using the program in the server at [http://www.carbon.wi.mit.edu: 8000/cgi-bin/contig/rhmapper.pl], the result was compared with similar codes of gene map marker genes used for constructing frame-work maps, and the location on the chromosome was determined. As a result, NR10 was mapped on chromosome 5 proximal to the centrosome, and was further confirmed that it exists between the markers WI-3071 (60-61 cM) and AFM183YB8 (67 cM).

Human gp130 and LIF receptor genes, which were used in the original database search by the inventors, were also mapped on regions of chromosome 5. More specifically, the human gp130 gene was mapped on chromosome 5 q11 (67.2-69.6 cM), and human LIF receptor gene was mapped on chromosome 5 p12-p13 (59.9-61.1 cM).

From the point of evolutionary genetics, it is also of great importance that the NR10 gene was mapped to the region 61-67 cM on chromosome 5, a region between the two genes. That is, the three genes, human gp130, human LIF receptor, and human NR10 genes, of the same receptor family, whose structures show relatively high similarity in the family, are located close to each other in an extremely restricted region of the same human chromosome 5. This fact supports the theory that the three different receptor genes are derived from a same ancestral gene, and that they went through genetical evolution during the long history of biological evolution to achieve diversity not only in their structure but also functions.

INDUSTRIAL APPLICABILITY

The present invention provides novel hemopoietin receptor proteins and DNA encoding same. The present invention also provides: a vector into which the DNA has been inserted, a transformant harboring the DNA, and a method for producing recombinant proteins using the transformant. It further provides a method of screening for a compound or a natural ligand that binds to the protein. The protein of the invention is thought to be associated with immunological and hematopoietic functions. Therefore, it is expected that the proteins of this invention can be applied for diagnosis and treatment of diseases related with immunity and hematopoiesis.

As described above, the NR10 gene is expected to provide a useful source for obtaining novel hematopoietic factors or agonists that are capable of functionally binding to the receptor protein encoded by the gene. It is expected that cellular immunity or hematopoietic function in vivo will be enhanced by administering such functional binding substances or specific antibodies that can activate the function of NR10 molecule to the organism. Thus, it is possible to develop a drug for clinical application that promotes proliferation or differentiation of the immune responsible cells or hematopoietic cells, or that activates the function of the immune cells by using the NR10 gene. It is also possible to use such drugs to enhance the cytotoxic immunity against particular types of tumor. It is possible that NR10.1 is expressed in a restricted population of cells in the hematopoietic tissues. Accordingly, anti-NR10 antibodies would be useful for the isolation of such cell populations, which may be used for cell transplantation treatments.

On the other hand, NR10.2, a splice variant of NR10, may be used as an inhibitor for the NR10 ligand, as a decoy type receptor. Further, it is expected that by administering antagonists that can bind functionally to the NR10 molecule, or other inhibitors, as well as specific antibodies that can inhibit the molecular function of NR10 to the organism, it is possible to suppress the cellular immunity or inhibit the proliferation of hematopoietic cells in vivo. Thus, it is possible to apply such inhibitors to the development of a drug for clinical application that inhibits the proliferation or differentiation of the immune responsible cells or hematopoietic cells, or suppresses the immune function or inflammation. Specifically, it is possible to use such inhibitors to suppress the onset of autoimmune diseases arising from autoimmunity, or tissue rejection by the immune system of the living body, the primary problem in transplantation. Furthermore, the inhibitors may be effectively used to treat such diseases caused by the abnormally upregulated immune response. Thus, it is possible to use the inhibitors to treat a variety of allergies that are specific to particular antigens, such as metal and pollen.

What is claimed is:

1. A purified antibody, or antigen-binding fragment thereof, that binds specifically to a polypeptide consisting of the amino acid sequence of SEQ ID NO:2.

2. A purified antibody, or antigen-binding fragment thereof, that binds specifically to a polypeptide consisting of the amino acid sequence of SEQ ID NO:4.

3. A purified antibody, or antigen-binding fragment thereof, that binds specifically to a polypeptide consisting of the amino acid sequence of SEQ ID NO:17.

4. The antibody of claim 1, wherein the antibody is monoclonal.

5. The antibody of claim 2, wherein the antibody is monoclonal.

6. The antibody of claim 3, wherein the antibody is monoclonal.

7. The antibody of claim 1, wherein the antibody is humanized.

8. The antibody of claim 2, wherein the antibody is humanized.

9. The antibody of claim 3, wherein the antibody is humanized.

10. The antibody of claim 1, wherein the antibody is bound to a molecule using chemical modification.

11. The antibody of claim 2, wherein the antibody is bound to a molecule using chemical modification.

12. The antibody of claim 3, wherein the antibody is bound to a molecule using chemical modification.

13. The antibody of claim 1, wherein the antibody is chimeric.

14. The antibody of claim 2, wherein the antibody is chimeric.

15. The antibody of claim 3, wherein the antibody is chimeric.

16. The antibody of claim 1, wherein the antibody is a single chain Fv.

17. The antibody of claim 2, wherein the antibody is a single chain Fv.

18. The antibody of claim 3, wherein the antibody is a single chain Fv.

19. A method of detecting a NR10 hemopoietin receptor protein in a test sample, the method comprising: contacting a test sample with the antibody of claim 1; and detecting the presence of an immune complex between the antibody and a NR10 hemopoietin receptor protein in the test sample.

20. A method of detecting a NR10 hemopoietin receptor protein in a test sample, the method comprising: contacting a test sample with the antibody of claim 2; and detecting the presence of an immune complex between the antibody and a NR10 hemopoietin receptor protein in the test sample.

21. A method of detecting a NR10 hemopoietin receptor protein in a test sample, the method comprising: contacting a test sample with the antibody of claim 3; and detecting the presence of an immune complex between the antibody and a NR10 hemopoietin receptor protein in the test sample.

* * * * *

UNITED STATES PATENT AND TRADEMARK OFFICE
CERTIFICATE OF CORRECTION

PATENT NO. : 8,017,738 B2
APPLICATION NO. : 11/980135
DATED : September 13, 2011
INVENTOR(S) : Masatsugu Maeda and Noriko Yaguchi It is certified that error appears in the above-identified patent and that said Letters Patent is hereby corrected as shown below:

First Page, right column (Other Publications), lines 10-12, Delete "Fish & Richardson P.C Amendment in Reply to Action dated Jun. 4, 2009 in U.S. Appl. 11/595,320, filed Dec. 3, 2009, 13 pages." and insert the same as a New Entry on the First Page, right column, line 11, below "535-539 (1998)."

Signed and Sealed this
Twenty-fourth Day of April, 2012

David J. Kappos
*Director of the United States Patent and Trademark Office*

SEQUENCE LISTING

```
<160> NUMBER OF SEQ ID NOS: 40

<210> SEQ ID NO 1
<211> LENGTH: 2969
<212> TYPE: DNA
<213> ORGANISM: Homo sapiens
<220> FEATURE:
<221> NAME/KEY: CDS
<222> LOCATION: (523)...(2478)

<400> SEQUENCE: 1
cgcttataaa tgaatgtgtg cttaggaaca ccagacagca ctccagcact ctgcttgggg      60
ggcattcgaa acagcaaaat cactcataaa aggcaaaaaa ttgcaaaaaa aatagtaata     120
accagcatgg tactaaatag accatgaaaa gacatgtgtg tgcagtatga aaattgagac     180
aggaaggcag agtgtcagct tgttccacct cagctgggaa tgtgcatcag gcaactcaag     240
tttttcacca cggcatgtgt ctgtgaatgt ccgcaaaaca ttttaacaat aatgcaatcc     300
atttcccagc ataagtgggt aagtgccact ttgacttggg ctgggcttaa aagcacaaga     360
aaagctcgca gacaatcaga gtggaaacac tcccacatct tagtgtggat aaattaaagt     420
ccagattgtt cttcctgtcc tgacttgtgc tgtgggaggt ggagttgcct tgatgcaaa      480 tcctttgagc cagcagaaca tctgtggaac atcccctgat ac atg aag ctc tct       534
                                                Met Lys Leu Ser
                                                  1 ccc cag cct tca tgt gtt aac ctg ggg atg atg tgg acc tgg gca ctg       582
Pro Gln Pro Ser Cys Val Asn Leu Gly Met Met Trp Thr Trp Ala Leu
  5                  10                  15                  20 tgg atg ctc ccc tca ctc tgc aaa ttc agc ctg gca gct ctg cca gct       630
Trp Met Leu Pro Ser Leu Cys Lys Phe Ser Leu Ala Ala Leu Pro Ala
                 25                  30                  35 aag cct gag aac att tcc tgt gtc tac tac tat agg aaa aat tta acc       678
Lys Pro Glu Asn Ile Ser Cys Val Tyr Tyr Tyr Arg Lys Asn Leu Thr
```

```
            40                  45                   50
tgc act tgg agt cca gga aag gaa acc agt tat acc cag tac aca gtt      726
Cys Thr Trp Ser Pro Gly Lys Glu Thr Ser Tyr Thr Gln Tyr Thr Val
         55                  60                  65 aag aga act tac gct ttc gga gaa aaa cat gat aat tgt aca acc aat      774
Lys Arg Thr Tyr Ala Phe Gly Glu Lys His Asp Asn Cys Thr Thr Asn
 70                  75                  80 agt tct aca agt gaa aat cgt gct tcg tgc tct ttt ttc ctt cca aga      822
Ser Ser Thr Ser Glu Asn Arg Ala Ser Cys Ser Phe Phe Leu Pro Arg
 85                  90                  95                 100 ata acg atc cca gat aat tat acc att gag gtg gaa gct gaa aat gga      870
Ile Thr Ile Pro Asp Asn Tyr Thr Ile Glu Val Glu Ala Glu Asn Gly
                105                 110                 115 gat ggt gta att aaa tct cat atg aca tac tgg aga tta gag aac ata      918
Asp Gly Val Ile Lys Ser His Met Thr Tyr Trp Arg Leu Glu Asn Ile
                120                 125                 130 gcg aaa act gaa cca cct aag att ttc cgt gtg aaa cca gtt ttg ggc      966
Ala Lys Thr Glu Pro Pro Lys Ile Phe Arg Val Lys Pro Val Leu Gly
                135                 140                 145 atc aaa cga atg att caa att gaa tgg ata aag cct gag ttg gcg cct     1014
Ile Lys Arg Met Ile Gln Ile Glu Trp Ile Lys Pro Glu Leu Ala Pro
150                 155                 160 gtt tca tct gat tta aaa tac aca ctt cga ttc agg aca gtc aac agt     1062
Val Ser Ser Asp Leu Lys Tyr Thr Leu Arg Phe Arg Thr Val Asn Ser
165                 170                 175                 180 acc agc tgg atg gaa gtc aac ttc gct aag aac cgt aag gat aaa aac     1110
Thr Ser Trp Met Glu Val Asn Phe Ala Lys Asn Arg Lys Asp Lys Asn
                185                 190                 195 caa acg tac aac ctc acg ggg ctg cag cct ttt aca gaa tat gtc ata     1158
Gln Thr Tyr Asn Leu Thr Gly Leu Gln Pro Phe Thr Glu Tyr Val Ile
                200                 205                 210 gct ctg cga tgt gcg gtc aag gag tca aag ttc tgg agt gac tgg agc     1206
Ala Leu Arg Cys Ala Val Lys Glu Ser Lys Phe Trp Ser Asp Trp Ser
                215                 220                 225 caa gaa aaa atg gga atg act gag gaa gaa gct cca tgt ggc ctg gaa     1254
Gln Glu Lys Met Gly Met Thr Glu Glu Glu Ala Pro Cys Gly Leu Glu
                230                 235                 240 ctg tgg aga gtc ctg aaa cca gct gag gcg gat gga aga agg cca gtg     1302
Leu Trp Arg Val Leu Lys Pro Ala Glu Ala Asp Gly Arg Arg Pro Val
245                 250                 255                 260 cgg ttg tta tgg aag aag gca aga gga gcc cca gtc cta gag aaa aca     1350
Arg Leu Leu Trp Lys Lys Ala Arg Gly Ala Pro Val Leu Glu Lys Thr
                265                 270                 275 ctt ggc tac aac ata tgg tac tat cca gaa agc aac act aac ctc aca     1398
Leu Gly Tyr Asn Ile Trp Tyr Tyr Pro Glu Ser Asn Thr Asn Leu Thr
                280                 285                 290 gaa aca atg aac act act aac cag cag ctt gaa ctg cat ctg gga ggc     1446
Glu Thr Met Asn Thr Thr Asn Gln Gln Leu Glu Leu His Leu Gly Gly
                295                 300                 305 gag agc ttt tgg gtg tct atg att tct tat aat tct ctt ggg aag tct     1494
Glu Ser Phe Trp Val Ser Met Ile Ser Tyr Asn Ser Leu Gly Lys Ser
                310                 315                 320 cca gtg gcc acc ctg agg att cca gct att caa gaa aaa tca ttt cag     1542
Pro Val Ala Thr Leu Arg Ile Pro Ala Ile Gln Glu Lys Ser Phe Gln
325                 330                 335                 340 tgc att gag gtc atg cag gcc tgc gtt gct gag gac cag cta gtg gtg     1590
Cys Ile Glu Val Met Gln Ala Cys Val Ala Glu Asp Gln Leu Val Val
                345                 350                 355 aag tgg caa agc tct gct cta gac gtg aac act tgg atg att gaa tgg     1638
Lys Trp Gln Ser Ser Ala Leu Asp Val Asn Thr Trp Met Ile Glu Trp
```

```
                       360                  365                  370
ttt ccg gat gtg gac tca gag ccc acc acc ctt tcc tgg gaa tct gtg        1686
Phe Pro Asp Val Asp Ser Glu Pro Thr Thr Leu Ser Trp Glu Ser Val
        375                  380                  385 tct cag gcc acg aac tgg acg atc cag caa gat aaa tta aaa cct ttc        1734
Ser Gln Ala Thr Asn Trp Thr Ile Gln Gln Asp Lys Leu Lys Pro Phe
        390                  395                  400 tgg tgc tat aac atc tct gtg tat cca atg ttg cat gac aaa gtt ggc        1782
Trp Cys Tyr Asn Ile Ser Val Tyr Pro Met Leu His Asp Lys Val Gly
405                  410                  415                  420 gag cca tat tcc atc cag gct tat gcc aaa gaa ggc gtt cca tca gaa        1830
Glu Pro Tyr Ser Ile Gln Ala Tyr Ala Lys Glu Gly Val Pro Ser Glu
                425                  430                  435 ggt cct gag acc aag gtg gag aac att ggc gtg aag acg gtc acg atc        1878
Gly Pro Glu Thr Lys Val Glu Asn Ile Gly Val Lys Thr Val Thr Ile
        440                  445                  450 aca tgg aaa gag att ccc aag agt gag aga aag ggt atc atc tgc aac        1926
Thr Trp Lys Glu Ile Pro Lys Ser Glu Arg Lys Gly Ile Ile Cys Asn
        455                  460                  465 tac acc atc ttt tac caa gct gaa ggt gga aaa gga ttc tcc aag aca        1974
Tyr Thr Ile Phe Tyr Gln Ala Glu Gly Gly Lys Gly Phe Ser Lys Thr
470                  475                  480 gtc aat tcc agc atc ttg cag tac ggc ctg gag tcc ctg aaa cga aag        2022
Val Asn Ser Ser Ile Leu Gln Tyr Gly Leu Glu Ser Leu Lys Arg Lys
485                  490                  495                  500 acc tct tac att gtt cag gtc atg gcc aac acc agt gct ggg gga acc        2070
Thr Ser Tyr Ile Val Gln Val Met Ala Asn Thr Ser Ala Gly Gly Thr
                505                  510                  515 aac ggg acc agc ata aat ttc aag aca ttg tca ttc agt gtc ttt gag        2118
Asn Gly Thr Ser Ile Asn Phe Lys Thr Leu Ser Phe Ser Val Phe Glu
        520                  525                  530 att atc ctc ata act tct ctg att ggt gga ggc ctt ctt att ctc att        2166
Ile Ile Leu Ile Thr Ser Leu Ile Gly Gly Gly Leu Leu Ile Leu Ile
        535                  540                  545 atc ctg aca gtg gca tat ggt ctc aaa aaa ccc aac aaa ttg act cat        2214
Ile Leu Thr Val Ala Tyr Gly Leu Lys Lys Pro Asn Lys Leu Thr His
        550                  555                  560 ctg tgt tgg ccc acc gtt ccc aac cct gct gaa agt agt ata gcc aca        2262
Leu Cys Trp Pro Thr Val Pro Asn Pro Ala Glu Ser Ser Ile Ala Thr
565                  570                  575                  580 tgg cat gga gat gat ttc aag gat aag cta aac ctg aag gag tct gat        2310
Trp His Gly Asp Asp Phe Lys Asp Lys Leu Asn Leu Lys Glu Ser Asp
                585                  590                  595 gac tct gtg aac aca gaa gac agg atc tta aaa cca tgt tcc acc ccc        2358
Asp Ser Val Asn Thr Glu Asp Arg Ile Leu Lys Pro Cys Ser Thr Pro
        600                  605                  610 agt gac aag ttg gtg att gac aag ttg gtg gtg aac ttt ggg aat gtt        2406
Ser Asp Lys Leu Val Ile Asp Lys Leu Val Val Asn Phe Gly Asn Val
        615                  620                  625 ctg caa gaa att ttc aca gat gaa gcc aga acg ggt cag gaa aaa caa        2454
Leu Gln Glu Ile Phe Thr Asp Glu Ala Arg Thr Gly Gln Glu Lys Gln
        630                  635                  640 ttt agg agg gga aaa gaa tgg gac tagaattctg tcttcctgcc caacttcaat      2508
Phe Arg Arg Gly Lys Glu Trp Asp
645                  650 ataagtgtgg actaaaatgc gagaaaggtg tcctgtggtc tatgcaaatt agaaggaca       2568 tgcagagttt tccaactagg aagactgaat ctgtggcccc aagagaacca tctccgaaga     2628
ctgggtatgt ggtcttttcc acacatggac cacctacgga tgcaatctgt aatgcatgtg    2688
```

-continued

```
catgagaagt ctgttattaa gtagagtgtg aaaacatggt tatggtaata ggaacagctt  2748
ttaaaatgct tttgtatttg ggcctttcac acaaaaaagc cataatacca ttttcatgta  2808
atgctatact tctatactat tttcatgtaa tactatactt ctatactatt ttcatgtaat  2868
actatacttc tatactattt tcatgtaata ctatacttct atattaaagt tttacccact  2928
ccaaaaaaag aaaaaaaaaa aaaaaaaaaa aaaaaaaaaa a  2969
```

<210> SEQ ID NO 2
<211> LENGTH: 652
<212> TYPE: PRT
<213> ORGANISM: Homo sapiens

<400> SEQUENCE: 2

```
Met Lys Leu Ser Pro Gln Pro Ser Cys Val Asn Leu Gly Met Met Trp
 1               5                   10                  15

Thr Trp Ala Leu Trp Met Leu Pro Ser Leu Cys Lys Phe Ser Leu Ala
             20                  25                  30

Ala Leu Pro Ala Lys Pro Glu Asn Ile Ser Cys Val Tyr Tyr Tyr Arg
         35                  40                  45

Lys Asn Leu Thr Cys Thr Trp Ser Pro Gly Lys Glu Thr Ser Tyr Thr
 50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                 85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335
```

| | | | | | | | | | | | |
|---|---|---|---|---|---|---|---|---|---|---|---|
|Lys|Ser|Phe|Gln|Cys|Ile|Glu|Val|Met|Gln|Ala|Cys|Val|Ala|Glu|Asp|
| | |340| | | |345| | | |350| |

Lys Ser Phe Gln Cys Ile Glu Val Met Gln Ala Cys Val Ala Glu Asp
            340                345                350

Gln Leu Val Val Lys Trp Gln Ser Ser Ala Leu Asp Val Asn Thr Trp
            355                360                365

Met Ile Glu Trp Phe Pro Asp Val Asp Ser Glu Pro Thr Thr Leu Ser
            370                375                380

Trp Glu Ser Val Ser Gln Ala Thr Asn Trp Thr Ile Gln Gln Asp Lys
385                390                395              400

Leu Lys Pro Phe Trp Cys Tyr Asn Ile Ser Val Tyr Pro Met Leu His
            405                410                415

Asp Lys Val Gly Glu Pro Tyr Ser Ile Gln Ala Tyr Ala Lys Glu Gly
            420                425                430

Val Pro Ser Glu Gly Pro Glu Thr Lys Val Glu Asn Ile Gly Val Lys
            435                440                445

Thr Val Thr Ile Thr Trp Lys Glu Ile Pro Lys Ser Glu Arg Lys Gly
450                455                460

Ile Ile Cys Asn Tyr Thr Ile Phe Tyr Gln Ala Glu Gly Gly Lys Gly
465                470                475              480

Phe Ser Lys Thr Val Asn Ser Ser Ile Leu Gln Tyr Gly Leu Glu Ser
            485                490                495

Leu Lys Arg Lys Thr Ser Tyr Ile Val Gln Val Met Ala Asn Thr Ser
            500                505                510

Ala Gly Gly Thr Asn Gly Thr Ser Ile Asn Phe Lys Thr Leu Ser Phe
            515                520                525

Ser Val Phe Glu Ile Ile Leu Ile Thr Ser Leu Ile Gly Gly Gly Leu
            530                535                540

Leu Ile Leu Ile Ile Leu Thr Val Ala Tyr Gly Leu Lys Lys Pro Asn
545                550                555              560

Lys Leu Thr His Leu Cys Trp Pro Thr Val Pro Asn Pro Ala Glu Ser
            565                570                575

Ser Ile Ala Thr Trp His Gly Asp Asp Phe Lys Asp Lys Leu Asn Leu
            580                585                590

Lys Glu Ser Asp Asp Ser Val Asn Thr Glu Asp Arg Ile Leu Lys Pro
            595                600                605

Cys Ser Thr Pro Ser Asp Lys Leu Val Ile Asp Lys Leu Val Val Asn
            610                615                620

Phe Gly Asn Val Leu Gln Glu Ile Phe Thr Asp Glu Ala Arg Thr Gly
625                630                635              640

Gln Glu Lys Gln Phe Arg Arg Gly Lys Glu Trp Asp
            645                650

<210> SEQ ID NO 3
<211> LENGTH: 2440
<212> TYPE: DNA
<213> ORGANISM: Homo sapiens
<220> FEATURE:
<221> NAME/KEY: CDS
<222> LOCATION: (523)...(1278)

<400> SEQUENCE: 3

```
cgcttataaa tgaatgtgtg cttaggaaca ccagacagca ctccagcact ctgcttgggg      60
ggcattcgaa acagcaaaat cactcataaa aggcaaaaaa ttgcaaaaaa aatagtaata     120
accagcatgg tactaaatag accatgaaaa gacatgtgtg tgcagtatga aaattgagac     180
aggaaggcag agtgtcagct tgttccacct cagctgggaa tgtgcatcag gcaactcaag     240
```

-continued

```
tttttcacca cggcatgtgt ctgtgaatgt ccgcaaaaca ttttaacaat aatgcaatcc      300
atttcccagc ataagtgggt aagtgccact ttgacttggg ctgggcttaa aagcacaaga      360
aaagctcgca gacaatcaga gtggaaacac tcccacatct tagtgtggat aaattaaagt      420
ccagattgtt cttcctgtcc tgacttgtgc tgtgggaggt ggagttgcct ttgatgcaaa      480
tcctttgagc cagcagaaca tctgtggaac atcccctgat ac atg aag ctc tct        534
                                             Met Lys Leu Ser
                                              1
```

| | | | | | | | | | | | | | | | | |
|---|---|---|---|---|---|---|---|---|---|---|---|---|---|---|---|---|
| ccc cag cct tca tgt gtt aac ctg ggg atg atg tgg acc tgg gca ctg | | | | | | | | | | | | | | | | 582 |
| Pro Gln Pro Ser Cys Val Asn Leu Gly Met Met Trp Thr Trp Ala Leu | | | | | | | | | | | | | | | | |
|  5         10                 15                 20 | | | | | | | | | | | | | | | | |

```
ccc cag cct tca tgt gtt aac ctg ggg atg atg tgg acc tgg gca ctg      582
Pro Gln Pro Ser Cys Val Asn Leu Gly Met Met Trp Thr Trp Ala Leu
 5              10                  15                  20 tgg atg ctc ccc tca ctc tgc aaa ttc agc ctg gca gct ctg cca gct      630
Trp Met Leu Pro Ser Leu Cys Lys Phe Ser Leu Ala Ala Leu Pro Ala
             25                  30                  35 aag cct gag aac att tcc tgt gtc tac tac tat agg aaa aat tta acc      678
Lys Pro Glu Asn Ile Ser Cys Val Tyr Tyr Tyr Arg Lys Asn Leu Thr
                 40                  45                  50 tgc act tgg agt cca gga aag gaa acc agt tat acc cag tac aca gtt      726
Cys Thr Trp Ser Pro Gly Lys Glu Thr Ser Tyr Thr Gln Tyr Thr Val
         55                  60                  65 aag aga act tac gct ttc gga gaa aaa cat gat aat tgt aca acc aat      774
Lys Arg Thr Tyr Ala Phe Gly Glu Lys His Asp Asn Cys Thr Thr Asn
     70                  75                  80 agt tct aca agt gaa aat cgt gct tcg tgc tct ttt ttc ctt cca aga      822
Ser Ser Thr Ser Glu Asn Arg Ala Ser Cys Ser Phe Phe Leu Pro Arg
 85                  90                  95                 100 ata acg atc cca gat aat tat acc att gag gtg gaa gct gaa aat gga      870
Ile Thr Ile Pro Asp Asn Tyr Thr Ile Glu Val Glu Ala Glu Asn Gly
                105                 110                 115 gat ggt gta att aaa tct cat atg aca tac tgg aga tta gag aac ata      918
Asp Gly Val Ile Lys Ser His Met Thr Tyr Trp Arg Leu Glu Asn Ile
            120                 125                 130 gcg aaa act gaa cca cct aag att ttc cgt gtg aaa cca gtt ttg ggc      966
Ala Lys Thr Glu Pro Pro Lys Ile Phe Arg Val Lys Pro Val Leu Gly
        135                 140                 145 atc aaa cga atg att caa att gaa tgg ata aag cct gag ttg gcg cct     1014
Ile Lys Arg Met Ile Gln Ile Glu Trp Ile Lys Pro Glu Leu Ala Pro
    150                 155                 160 gtt tca tct gat tta aaa tac aca ctt cga ttc agg aca gtc aac agt     1062
Val Ser Ser Asp Leu Lys Tyr Thr Leu Arg Phe Arg Thr Val Asn Ser
165                 170                 175                 180 acc agc tgg atg gaa gtc aac ttc gct aag aac cgt aag gat aaa aac     1110
Thr Ser Trp Met Glu Val Asn Phe Ala Lys Asn Arg Lys Asp Lys Asn
                185                 190                 195 caa acg tac aac ctc acg ggg ctg cag cct ttt aca gaa tat gtc ata     1158
Gln Thr Tyr Asn Leu Thr Gly Leu Gln Pro Phe Thr Glu Tyr Val Ile
            200                 205                 210 gct ctg cga tgt gcg gtc aag gag tca aag ttc tgg agt gac tgg agc     1206
Ala Leu Arg Cys Ala Val Lys Glu Ser Lys Phe Trp Ser Asp Trp Ser
        215                 220                 225 caa gaa aaa atg gga atg act gag gaa gaa ggc aag cta ctc cct gcg     1254
Gln Glu Lys Met Gly Met Thr Glu Glu Glu Gly Lys Leu Leu Pro Ala
    230                 235                 240 att ccc gtc ctg tct act ctg gtg tagggctgct tgggctaga cttggtgggg     1308
Ile Pro Val Leu Ser Thr Leu Val
245                 250 tttgtcacca cctggttggg aatcatggaa tctcatgacc ccaggggccc cctgtaccat     1368
cgagagtgag cctgcacaac tttgtgcccc aaaggcaaag gatcacattt taatactcat     1428
```

```
gaggttctta tactatacat gaaagggtat catatcattt gttttgtttt gttttgtttt   1488
tgagatggag tcttactctg tcacccagga tggagtgcag tgatgtgatc tcggctcact   1548
gccaccacca cctcccgagt tcaagcaatt cttgtgcctc agcctcccaa gtagctggga   1608
ttacaggggc ccacgaccat gcccggttga ttttttgtatt tttagtagag aagggatatc   1668
accatgttgg ctaggctagt cttgaactcc tgacctcagg taatctgccc accttgacct   1728
cccaaagtgt tgggattaca ggcgtgagcc actgtgcccc gccagtatca tatcatctga   1788
aggtatcctg tgataaatta aagatacata ttgtgaatcc tggagctact actcaaaaaa   1848
taaataaagg tgtaactaat acaatttaaa aaatcacatt tttaatgaca gtgaggaaag   1908
gaaagaggca tggattgcag gttgatggag tgcttactaa gtgtcagtat ggtcattaag   1968
agcaacgctt ccagtcagtg gccttggctt aaatcccaag ccaggtgtct ttgggcaaga   2028
tacctaaact ctcagttcat tctcagcagt ttcctcgcat ttattcccct tttctatatt   2088
gaaatagaat atgtaagttg agtttatagt agtacctatt ttttagtatt attttaaaga   2148
ttaaatgaaa taatgtgttt agcccatagt agatattcac taactgctag acttcctatt   2208
cttattattt atcctcctac tattattttt aatcctcctt aaagcactat aaaatatgta   2268
gagtcactcc cattttggaa atgaggaaac tgagtttcag agatgctaat aaacagctca   2328
gggtcactca gcatgtgtta cttttctcaa gagccttgcc cagagtctga ccctcagtgg   2388
acgatcaata aatgtgtgat gaatggaaaa aaaaaaaaaa aaaaaaaaaa aa           2440
```

<210> SEQ ID NO 4
<211> LENGTH: 252
<212> TYPE: PRT
<213> ORGANISM: Homo sapiens

<400> SEQUENCE: 4

```
Met Lys Leu Ser Pro Gln Pro Ser Cys Val Asn Leu Gly Met Met Trp
  1               5                  10                  15

Thr Trp Ala Leu Trp Met Leu Pro Ser Leu Cys Lys Phe Ser Leu Ala
             20                  25                  30

Ala Leu Pro Ala Lys Pro Glu Asn Ile Ser Cys Val Tyr Tyr Tyr Arg
         35                  40                  45

Lys Asn Leu Thr Cys Thr Trp Ser Pro Gly Lys Glu Thr Ser Tyr Thr
     50                  55                  60

Gln Tyr Thr Val Lys Arg Thr Tyr Ala Phe Gly Glu Lys His Asp Asn
 65                  70                  75                  80

Cys Thr Thr Asn Ser Ser Thr Ser Glu Asn Arg Ala Ser Cys Ser Phe
                 85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205
```

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Gly Lys
225                 230                 235                 240

Leu Leu Pro Ala Ile Pro Val Leu Ser Thr Leu Val
                245                 250

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
atggaagtca acttcgctaa gaaccgtaag                              30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ccaaacgtac aacctcacgg ggctgcaacc                              30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gtcatagctc tgcgatgtgc ggtcaaggag                              30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
agtagcttgc gttcttcctc agctattccc                              30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ctttgactcc ttgaccgcac atcgcagagc                              30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10

```
ggttgcagcc ccgtgaggtt gtacgtttgg                                          30
```

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11

```
atcagatgaa acaggcgcca actcagg                                             27
```

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12

```
tggtttcaca cggaaaatct taggtgg                                             27
```

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13

```
gcattcagga cagtcaacag taccagc                                             27
```

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14

```
agctggaatc ctcagggtgg ccactgg                                             27
```

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15

```
gcccatcacc agagtagaca ggacggg                                             27
```

<210> SEQ ID NO 16
<211> LENGTH: 2119
<212> TYPE: DNA
<213> ORGANISM: Homo sapiens
<220> FEATURE:
<221> NAME/KEY: CDS
<222> LOCATION: (11)...(1996)

<400> SEQUENCE: 16

```
cccctgatac atg aag ctc tct ccc cag cct tca tgt gtt aac ctg ggg            49
            Met Lys Leu Ser Pro Gln Pro Ser Cys Val Asn Leu Gly
              1               5                  10 atg atg tgg acc tgg gca ctg tgg atg ctc ccc tca ctc tgc aaa ttc           97
Met Met Trp Thr Trp Ala Leu Trp Met Leu Pro Ser Leu Cys Lys Phe
 15                  20                  25
```

```
agc ctg gca gct ctg cca gct aag cct gag aac att tcc tgt gtc tac       145
Ser Leu Ala Ala Leu Pro Ala Lys Pro Glu Asn Ile Ser Cys Val Tyr
 30              35                  40                  45 tac tat agg aaa aat tta acc tgc act tgg agt cca gga aag gaa acc       193
Tyr Tyr Arg Lys Asn Leu Thr Cys Thr Trp Ser Pro Gly Lys Glu Thr
             50                  55                  60 agt tat acc cag tac aca gtt aag aga act tac gct ttt gga gaa aaa       241
Ser Tyr Thr Gln Tyr Thr Val Lys Arg Thr Tyr Ala Phe Gly Glu Lys
         65                  70                  75 cat gat aat tgt aca acc aat agt tct aca agt gaa aat cgt gct tcg       289
His Asp Asn Cys Thr Thr Asn Ser Ser Thr Ser Glu Asn Arg Ala Ser
     80                  85                  90 tgc tct ttt ttc ctt cca aga ata acg atc cca gat aat tat acc att       337
Cys Ser Phe Phe Leu Pro Arg Ile Thr Ile Pro Asp Asn Tyr Thr Ile
 95                 100                 105 gag gtg gaa gct gaa aat gga gat ggt gta att aaa tct cat atg aca       385
Glu Val Glu Ala Glu Asn Gly Asp Gly Val Ile Lys Ser His Met Thr
110             115                 120                 125 tac tgg aga tta gag aac ata gcg aaa act gaa cca cct aag att ttc       433
Tyr Trp Arg Leu Glu Asn Ile Ala Lys Thr Glu Pro Pro Lys Ile Phe
            130                 135                 140 cgt gtg aaa cca gtt ttg ggc atc aaa cga atg att caa att gaa tgg       481
Arg Val Lys Pro Val Leu Gly Ile Lys Arg Met Ile Gln Ile Glu Trp
        145                 150                 155 ata aag cct gag ttg gcg cct gtt tca tct gat tta aaa tac aca ctt       529
Ile Lys Pro Glu Leu Ala Pro Val Ser Ser Asp Leu Lys Tyr Thr Leu
    160                 165                 170 cga ttc agg aca gtc aac agt acc agc tgg atg gaa gtc aac ttc gct       577
Arg Phe Arg Thr Val Asn Ser Thr Ser Trp Met Glu Val Asn Phe Ala
175                 180                 185 aag aac cgt aag gat aaa aac caa acg tac aac ctc acg ggg ctg cag       625
Lys Asn Arg Lys Asp Lys Asn Gln Thr Tyr Asn Leu Thr Gly Leu Gln
190                 195                 200                 205 cct ttt aca gaa tat gtc ata gct ctg cga tgt gcg gtc aag gag tca       673
Pro Phe Thr Glu Tyr Val Ile Ala Leu Arg Cys Ala Val Lys Glu Ser
            210                 215                 220 aag ttc tgg agt gac tgg agc caa gaa aaa atg gga atg act gag gaa       721
Lys Phe Trp Ser Asp Trp Ser Gln Glu Lys Met Gly Met Thr Glu Glu
        225                 230                 235 gaa gct cca tgt ggc ctg gaa ctg tgg aga gtc ctg aaa cca gct gag       769
Glu Ala Pro Cys Gly Leu Glu Leu Trp Arg Val Leu Lys Pro Ala Glu
    240                 245                 250 gcg gat gga aga agg cca gtg cgg ttg tta tgg aag aag gca aga gga       817
Ala Asp Gly Arg Arg Pro Val Arg Leu Leu Trp Lys Lys Ala Arg Gly
255                 260                 265 gcc cca gtc cta gag aaa aca ctt ggc tac aac ata tgg tac tat cca       865
Ala Pro Val Leu Glu Lys Thr Leu Gly Tyr Asn Ile Trp Tyr Tyr Pro
270             275                 280                 285 gaa agc aac act aac ctc aca gaa aca atg aac act act aac cag cag       913
Glu Ser Asn Thr Asn Leu Thr Glu Thr Met Asn Thr Thr Asn Gln Gln
            290                 295                 300 ctt gaa ctg cat ctg gga ggc gag agc ttt tgg gtg tct atg att tct       961
Leu Glu Leu His Leu Gly Gly Glu Ser Phe Trp Val Ser Met Ile Ser
        305                 310                 315 tat aat tct ctt ggg aag tct cca gtg gcc acc ctg agg att cca gct      1009
Tyr Asn Ser Leu Gly Lys Ser Pro Val Ala Thr Leu Arg Ile Pro Ala
    320                 325                 330 att caa gaa aaa tca ttt cag tgc att gag gtc atg cag gcc tgc gtt      1057
Ile Gln Glu Lys Ser Phe Gln Cys Ile Glu Val Met Gln Ala Cys Val
335                 340                 345
```

```
gct gag gac cag cta gtg gtg aag tgg caa agc tct gct cta gac gtg      1105
Ala Glu Asp Gln Leu Val Val Lys Trp Gln Ser Ser Ala Leu Asp Val
350                 355                 360                 365 aac act tgg atg att gaa tgg ttt ccg gat gtg gac tca gag ccc acc      1153
Asn Thr Trp Met Ile Glu Trp Phe Pro Asp Val Asp Ser Glu Pro Thr
                370                 375                 380 acc ctt tcc tgg gaa tct gtg tct cag gcc acg aac tgg acg atc cag      1201
Thr Leu Ser Trp Glu Ser Val Ser Gln Ala Thr Asn Trp Thr Ile Gln
            385                 390                 395 caa gat aaa tta aaa cct ttc tgg tgc tat aac atc tct gtg tat cca      1249
Gln Asp Lys Leu Lys Pro Phe Trp Cys Tyr Asn Ile Ser Val Tyr Pro
        400                 405                 410 atg ttg cat gac aaa gtt ggc gag cca tat tcc atc cag gct tat gcc      1297
Met Leu His Asp Lys Val Gly Glu Pro Tyr Ser Ile Gln Ala Tyr Ala
    415                 420                 425 aaa gaa ggc gtt cca tca gaa ggt cct gag acc aag gtg gag aac att      1345
Lys Glu Gly Val Pro Ser Glu Gly Pro Glu Thr Lys Val Glu Asn Ile
430                 435                 440                 445 ggc gtg aag acg gtc acg atc aca tgg aaa gag att ccc aag agt gag      1393
Gly Val Lys Thr Val Thr Ile Thr Trp Lys Glu Ile Pro Lys Ser Glu
                450                 455                 460 aga aag ggt atc atc tgc aac tac acc atc ttt tac caa gct gaa ggt      1441
Arg Lys Gly Ile Ile Cys Asn Tyr Thr Ile Phe Tyr Gln Ala Glu Gly
            465                 470                 475 gga aaa gga ttc tcc aag aca gtc aat tcc agc atc ttg cag tac ggc      1489
Gly Lys Gly Phe Ser Lys Thr Val Asn Ser Ser Ile Leu Gln Tyr Gly
        480                 485                 490 ctg gag tcc ctg aaa cga aag acc tct tac att gtt cag gtc atg gcc      1537
Leu Glu Ser Leu Lys Arg Lys Thr Ser Tyr Ile Val Gln Val Met Ala
    495                 500                 505 agc acc agt gct ggg gga acc aac ggg acc agc ata aat ttc aag aca      1585
Ser Thr Ser Ala Gly Gly Thr Asn Gly Thr Ser Ile Asn Phe Lys Thr
510                 515                 520                 525 ttg tca ttc agt gtc ttt gag att atc ctc ata act tct ctg att ggt      1633
Leu Ser Phe Ser Val Phe Glu Ile Ile Leu Ile Thr Ser Leu Ile Gly
                530                 535                 540 gga ggc ctt ctt att ctc att atc ctg aca gtg gca tat ggt ctc aaa      1681
Gly Gly Leu Leu Ile Leu Ile Ile Leu Thr Val Ala Tyr Gly Leu Lys
            545                 550                 555 aaa ccc aac aaa ttg act cat ctg tgt tgg ccc acc gtt ccc aac cct      1729
Lys Pro Asn Lys Leu Thr His Leu Cys Trp Pro Thr Val Pro Asn Pro
        560                 565                 570 gct gaa agt agt ata gcc aca tgg cat gga gat gat ttc aag gat aag      1777
Ala Glu Ser Ser Ile Ala Thr Trp His Gly Asp Asp Phe Lys Asp Lys
    575                 580                 585 cta aac ctg aag gag tct gat gac tct gtg aac aca gaa gac agg atc      1825
Leu Asn Leu Lys Glu Ser Asp Asp Ser Val Asn Thr Glu Asp Arg Ile
590                 595                 600                 605 tta aaa cca tgt tcc acc ccc agt gac aag ttg gtg att gac aag ttg      1873
Leu Lys Pro Cys Ser Thr Pro Ser Asp Lys Leu Val Ile Asp Lys Leu
                610                 615                 620 gtg gtg aac ttt ggg aat gtt ctg caa gaa att ttc aca gat gaa gcc      1921
Val Val Asn Phe Gly Asn Val Leu Gln Glu Ile Phe Thr Asp Glu Ala
            625                 630                 635 aga acg ggt cag gaa aac aat tta gga ggg gaa aag aat ggg act aga      1969
Arg Thr Gly Gln Glu Asn Asn Leu Gly Gly Glu Lys Asn Gly Thr Arg
        640                 645                 650 att ctg tct tcc tgc cca act tca ata taagtgtgga ctaaaatgcg            2016
Ile Leu Ser Ser Cys Pro Thr Ser Ile
    655                 660
```

```
agaaaggtgt cctgtggtct atgcaaatta gaaaggacat gcagagtttt ccaactagga    2076
agactgaatc tgtggcccca agagaaccat ctccgaagac tgg                      2119
```

<210> SEQ ID NO 17
<211> LENGTH: 662
<212> TYPE: PRT
<213> ORGANISM: Homo sapiens

<400> SEQUENCE: 17

```
Met Lys Leu Ser Pro Gln Pro Ser Cys Val Asn Leu Gly Met Met Trp
 1               5                  10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
```

```
            355                 360                 365
Met Ile Glu Trp Phe Pro Asp Val Asp Ser Glu Pro Thr Thr Leu Ser
370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
    610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
cccctgatac atgaagctct ctccccagcc                                      30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
```

```
ccagtcttcg gagatggttc tcttggggcc                                30
```

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20

```
ctgtgtaagt accaattgtt cccaggc                                   27
```

<210> SEQ ID NO 21
<211> LENGTH: 15
<212> TYPE: DNA
<213> ORGANISM: Artificial Sequence
<220> FEATURE:
<223> OTHER INFORMATION: exemplary motif
<220> FEATURE:
<221> NAME/KEY: misc_feature
<222> LOCATION: 7-9
<223> OTHER INFORMATION: n = a, t, g, or c

<400> SEQUENCE: 21

```
tggagynnnt ggagy                                                15
```

<210> SEQ ID NO 22
<211> LENGTH: 5
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 3
<223> OTHER INFORMATION: Xaa = any amino acid

<400> SEQUENCE: 22

Trp Ser Xaa Trp Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: exemplary motif

<400> SEQUENCE: 23

Tyr Thr Val Gln Val Arg
 1               5

<210> SEQ ID NO 24
<211> LENGTH: 6
<212> TYPE: PRT
<213> ORGANISM: Artificial Sequence
<220> FEATURE:
<223> OTHER INFORMATION: exemplary motif

<400> SEQUENCE: 24

Tyr Glu Ala Arg Val Arg
 1               5

<210> SEQ ID NO 25
<211> LENGTH: 6
<212> TYPE: PRT
<213> ORGANISM: Artificial Sequence
<220> FEATURE:

```
<223> OTHER INFORMATION: exemplary motif

<400> SEQUENCE: 25

Tyr Ser Leu Gln Leu Arg
1               5

<210> SEQ ID NO 26
<211> LENGTH: 10
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 3-8
<223> OTHER INFORMATION: Xaa = any amino acid

<400> SEQUENCE: 26

Ala Arg Xaa Xaa Xaa Xaa Xaa Xaa Gly Thr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 3-8
<223> OTHER INFORMATION: Xaa = any amino acid

<400> SEQUENCE: 27

Val Gln Xaa Xaa Xaa Xaa Xaa Xaa Gly Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 3-8
<223> OTHER INFORMATION: Xaa = any amino acid

<400> SEQUENCE: 28

Cys Lys Xaa Xaa Xaa Xaa Xaa Xaa Gly Ile
1               5                   10

<210> SEQ ID NO 29
<211> LENGTH: 6
<212> TYPE: PRT
<213> ORGANISM: Artificial Sequence
<220> FEATURE:
<223> OTHER INFORMATION: exemplary motif

<400> SEQUENCE: 29

Trp Ser Glu Trp Ser Pro
1               5

<210> SEQ ID NO 30
<211> LENGTH: 6
<212> TYPE: PRT
<213> ORGANISM: Artificial Sequence
<220> FEATURE:
<223> OTHER INFORMATION: exemplary motif

<400> SEQUENCE: 30
```

```
<210> SEQ ID NO 31
<211> LENGTH: 6
<212> TYPE: PRT
<213> ORGANISM: Artificial Sequence
<220> FEATURE:
<223> OTHER INFORMATION: exemplary motif

<400> SEQUENCE: 31

Trp Ser Pro Trp Ser Gln
 1               5

<210> SEQ ID NO 32
<211> LENGTH: 6
<212> TYPE: PRT
<213> ORGANISM: Artificial Sequence
<220> FEATURE:
<223> OTHER INFORMATION: exemplary motif

<400> SEQUENCE: 32

Tyr Val Ile Ala Leu Arg
 1               5

<210> SEQ ID NO 33
<211> LENGTH: 5
<212> TYPE: PRT
<213> ORGANISM: Artificial Sequence
<220> FEATURE:
<223> OTHER INFORMATION: exemplary motif

<400> SEQUENCE: 33

Trp Ser Asp Trp Ser
 1               5

<210> SEQ ID NO 34
<211> LENGTH: 459
<212> TYPE: DNA
<213> ORGANISM: Homo sapiens
<220> FEATURE:
<221> NAME/KEY: CDS
<222> LOCATION: (211)...(399)
<220> FEATURE:
<221> NAME/KEY: misc_feature
<222> LOCATION: 281, 376, 420
<223> OTHER INFORMATION: n = A,T,C or G

<400> SEQUENCE: 34
ttggtggttc atggtgatgt tctatatctg tgtaagtacc aattgttccc aggcacatat      60
ggaagtctgt taataaaaat gatatatttt aaaatttgat ttagagtgtt actagttcta     120
aaaatgtaaa agtcacactag gtagtgaaga ggaaaatggg aggataacgt gtggtctcca    180 tttcagtttta cgattgtctc tgtcttgtag atg gaa gtc aac ttc gct aag aac     234
                                    Met Glu Val Asn Phe Ala Lys Asn
                                     1               5 cgt aag gat aaa aac caa acg tac aac ctc acg ggg ctg caa cct tnt       282
Arg Lys Asp Lys Asn Gln Thr Tyr Asn Leu Thr Gly Leu Gln Pro Xaa
         10                  15                  20 aca gaa tat gtc ata gct ctg cga tgt gcg gtc aag gag tca aag ttc       330
Thr Glu Tyr Val Ile Ala Leu Arg Cys Ala Val Lys Glu Ser Lys Phe
 25                  30                  35                  40 tgg agt gac tgg agc caa gaa aaa atg gga atg act gag gaa gaa ngc       378
Trp Ser Asp Trp Ser Gln Glu Lys Met Gly Met Thr Glu Glu Glu Xaa
                 45                  50                  55
```

```
aag cta ctt cct gcg att ccc gtcctgtctg ctctggtgta nggctgctct      429
Lys Leu Leu Pro Ala Ile Pro
            60 gcgctaaact tggtggtgtc tgcaccaccg                                   459
```

<210> SEQ ID NO 35
<211> LENGTH: 63
<212> TYPE: PRT
<213> ORGANISM: Homo sapiens
<220> FEATURE:
<221> NAME/KEY: VARIANT
<222> LOCATION: 24, 54
<223> OTHER INFORMATION: Xaa = any amino acid

<400> SEQUENCE: 35

```
Met Glu Val Asn Phe Ala Lys Asn Arg Lys Asp Lys Asn Gln Thr Tyr
1               5                   10                  15

Asn Leu Thr Gly Leu Gln Pro Xaa Thr Glu Tyr Val Ile Ala Leu Arg
            20                  25                  30

Cys Ala Val Lys Glu Ser Lys Phe Trp Ser Asp Trp Ser Gln Glu Lys
        35                  40                  45

Met Gly Met Thr Glu Glu Xaa Lys Leu Leu Pro Ala Ile Pro
    50                  55                  60
```

<210> SEQ ID NO 36
<211> LENGTH: 42
<212> TYPE: PRT
<213> ORGANISM: Homo sapiens

<400> SEQUENCE: 36

```
Ser Phe Thr Val Gln Asp Leu Lys Pro Phe Thr Glu Tyr Val Phe Arg
1               5                   10                  15

Ile Arg Cys Met Lys Glu Asp Gly Lys Gly Tyr Trp Ser Asp Trp Ser
            20                  25                  30

Glu Glu Ala Ser Gly Ile Thr Tyr Glu Asp
        35                  40
```

<210> SEQ ID NO 37
<211> LENGTH: 37
<212> TYPE: PRT
<213> ORGANISM: Homo sapiens

<400> SEQUENCE: 37

```
Leu Asp Lys Leu Asn Pro Tyr Thr Leu Tyr Thr Phe Arg Ile Arg Cys
1               5                   10                  15

Ser Thr Glu Thr Phe Trp Lys Trp Ser Lys Trp Ser Asn Lys Lys Gln
            20                  25                  30

His Leu Thr Thr Glu
        35
```

<210> SEQ ID NO 38
<211> LENGTH: 42
<212> TYPE: PRT
<213> ORGANISM: Homo sapiens

<400> SEQUENCE: 38

```
Asn Gly Glu Tyr Phe Leu Ser Glu Leu Glu Pro Ala Thr Glu Tyr Met
1               5                   10                  15

Ala Arg Val Arg Cys Ala Asp Ala Ser His Phe Trp Lys Trp Ser Glu
            20                  25                  30

Trp Ser Gly Gln Asn Phe Thr Thr Leu Glu
        35                  40
```

```
<210> SEQ ID NO 39
<211> LENGTH: 45
<212> TYPE: PRT
<213> ORGANISM: Homo sapiens

<400> SEQUENCE: 39

Ala Lys Gly Arg His Asp Leu Leu Asp Leu Lys Pro Phe Thr Glu Tyr
 1               5                  10                  15

Glu Phe Gln Ile Ser Ser Lys Leu His Leu Tyr Lys Gly Ser Trp Ser
            20                  25                  30

Asp Trp Ser Glu Ser Leu Arg Ala Gln Thr Pro Glu Glu
        35                  40                  45

<210> SEQ ID NO 40
<211> LENGTH: 51
<212> TYPE: PRT
<213> ORGANISM: Homo sapiens

<400> SEQUENCE: 40

Asn Gln Thr Ser Cys Arg Leu Ala Gly Leu Lys Pro Gly Thr Val Tyr
 1               5                  10                  15

Phe Val Gln Val Arg Cys Asn Pro Phe Gly Ile Tyr Gly Ser Lys Lys
            20                  25                  30

Ala Gly Ile Trp Ser Glu Trp Ser His Pro Thr Ala Ala Ser Thr Pro
        35                  40                  45

Arg Ser Gly
    50
```